(12) United States Patent
Baker, Jr. et al.

(10) Patent No.: US 8,236,335 B2
(45) Date of Patent: *Aug. 7, 2012

(54) ANTIMICROBIAL NANOEMULSION COMPOSITIONS AND METHODS

(75) Inventors: James R. Baker, Jr., Ann Arbor, MI (US); Tarek Hamouda, Milan, MI (US); Amy Shih, Ann Arbor, MI (US); Andrzej Myc, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 1204 days.

This patent is subject to a terminal disclaimer.

(21) Appl. No.: 11/928,447

(22) Filed: Oct. 30, 2007

(65) Prior Publication Data
US 2009/0143477 A1    Jun. 4, 2009

Related U.S. Application Data

(63) Continuation of application No. 10/179,547, filed on Jun. 25, 2002, now Pat. No. 7,655,252, which is a continuation-in-part of application No. 09/965,447, filed on Sep. 27, 2001, now Pat. No. 6,635,676, which is a continuation-in-part of application No. 09/891,086, filed on Jun. 25, 2001, now Pat. No. 6,559,189, which is a continuation-in-part of application No. 09/751,059, filed on Dec. 29, 2000, now Pat. No. 7,767,216, which is a continuation-in-part of application No. 09/561,111, filed on Apr. 28, 2000, now Pat. No. 6,506,803, which is a continuation-in-part of application No. 09/474,866, filed on Dec. 30, 1999, now abandoned.

(60) Provisional application No. 60/131,638, filed on Apr. 28, 1999.

(51) Int. Cl.
*A01N 25/00* (2006.01)
*A01N 33/12* (2006.01)
*A61K 9/00* (2006.01)

(52) U.S. Cl. .................. 424/405; 424/400; 514/642
(58) Field of Classification Search .................. 514/642; 424/405, 400
See application file for complete search history.

(56) References Cited

U.S. PATENT DOCUMENTS
3,864,472 A    2/1975   Pensak et al.
(Continued)

FOREIGN PATENT DOCUMENTS
CN    1159158    9/1997
(Continued)

OTHER PUBLICATIONS

Tarbox et al., "Benzalkonium chloride" 1998 Clinical Orthopaedics and Related Research, 346:255-261.
Wadhams et al., "Efficacy of a Surfactant Allantoin and Benzalkonium Chloride Solution for Onychomycosis" Journal of the American Podiatric Medical Association 89(3): 124-130, 1999.

(Continued)

*Primary Examiner* — Blessing Fubara
(74) *Attorney, Agent, or Firm* — Casimir Jones, S.C.

(57) ABSTRACT

The present invention relates to compositions and methods for decreasing the infectivity, morbidity, and rate of mortality associated with a variety of pathogenic organisms and viruses. The present invention also relates to methods and compositions for decontaminating areas colonized or otherwise infected by pathogenic organisms and viruses. Moreover, the present invention relates to methods and compositions for decreasing the infectivity of pathogenic organisms in foodstuffs.

17 Claims, 43 Drawing Sheets

U.S. PATENT DOCUMENTS

| | | | |
|---|---|---|---|
| 3,912,666 A | | 10/1975 | Spitzer et al. |
| 3,968,250 A | | 7/1976 | Boucher |
| 4,020,183 A | | 4/1977 | Asculai et al. |
| 4,262,007 A | | 4/1981 | Sherrill |
| 4,350,707 A | | 9/1982 | Keith et al. |
| 4,451,267 A | | 5/1984 | Schwab et al. |
| 4,599,088 A | | 7/1986 | Davis et al. |
| 4,886,670 A | | 12/1989 | Horrobin |
| 4,895,452 A | | 1/1990 | Yiournas et al. |
| 4,935,439 A | | 6/1990 | Kashman et al. |
| 5,073,372 A | | 12/1991 | Turner et al. |
| 5,103,497 A | | 4/1992 | Hicks |
| 5,108,660 A | | 4/1992 | Michael |
| 5,112,844 A | * | 5/1992 | Paradies .................. 514/398 |
| 5,118,808 A | | 6/1992 | Paradies |
| 5,188,822 A | | 2/1993 | Viccaro et al. |
| 5,366,983 A | * | 11/1994 | Lattin et al. .................. 514/358 |
| 5,368,837 A | | 11/1994 | Baker et al. |
| 5,380,530 A | | 1/1995 | Hill |
| 5,405,602 A | | 4/1995 | Simmons et al. |
| 5,405,604 A | | 4/1995 | Hall |
| 5,510,104 A | | 4/1996 | Allen |
| 5,536,502 A | | 7/1996 | Mulder |
| 5,547,677 A | | 8/1996 | Wright |
| 5,549,901 A | | 8/1996 | Wright |
| 5,576,016 A | | 11/1996 | Amselem et al. |
| 5,618,840 A | | 4/1997 | Wright |
| 5,651,959 A | | 7/1997 | Hill et al. |
| 5,656,280 A | | 8/1997 | Herb et al. |
| 5,662,932 A | | 9/1997 | Amselem et al. |
| 5,662,957 A | | 9/1997 | Wright |
| 5,698,219 A | | 12/1997 | Valdivia et al. |
| 5,700,679 A | | 12/1997 | Wright |
| 5,709,879 A | | 1/1998 | Barchfield et al. |
| 5,716,637 A | | 2/1998 | Anselem et al. |
| 5,855,872 A | * | 1/1999 | Libin .................................. 424/49 |
| 5,985,319 A | * | 11/1999 | Embil et al. .................. 424/450 |
| 6,165,500 A | * | 12/2000 | Cevc .............................. 424/450 |
| 6,506,803 B1 | * | 1/2003 | Baker et al. .................. 424/678 |
| 6,559,189 B2 | * | 5/2003 | Baker et al. .................. 514/642 |
| 6,635,676 B2 | * | 10/2003 | Baker et al. .................. 514/642 |
| 7,314,624 B2 | * | 1/2008 | Baker et al. ................ 424/192.1 |
| 7,655,252 B2 | * | 2/2010 | Baker et al. .................. 424/405 |
| 7,767,216 B2 | * | 8/2010 | Baker et al. .................. 424/405 |

FOREIGN PATENT DOCUMENTS

| | | |
|---|---|---|
| EP | 0832649 | 4/1998 |
| EP | 0278996 | 8/1998 |
| EP | 1655021 | 5/2006 |
| GB | 1321579 | 6/1973 |
| JP | H10-87428 | 4/1997 |
| WO | 9426252 | 11/1994 |
| WO | 9531966 | 10/1995 |
| WO | 9531956 | 11/1995 |
| WO | 9623409 | 8/1996 |
| WO | 9633725 | 10/1996 |

OTHER PUBLICATIONS

Wainberg et al., "Effect of Benzokonium Chloride on HIV and Related Infection on other Infectious Agents" 1987 Arch. AIDS Res., 1:57-68.

Mascola, Herpes Simplex Virus Vaccines—Why Don't Antibodies Protect?, JAMA, vol. 282, No. 4, pp. 379-380, 1999.

Sadovski, Varicella-zoster and herpes simplex virus infections—Tips from other Journals, in American Family Physician, Sep. 15, 1997.

Dobson et al. "Herpes simplex virus type 1 and Alzheimer,s disease," in Neurobiology of Aging 20 (1999) 457-465.

Barrett and Inglis "Growth purification and titration of influenza viruses." In: Mahy WJ. ed. Virology. a Practical approach. IRL. Press, 1985; 119•151. This reference is a book and is not being submitted at this time but if the Examiner requests the reference it will be submitted.

Chatlyyne et al., "A lipid emulsion with effective virucidal activity against H IV-I and other common viruses." Foundation for Retrovirology and Human Health, 3rd Conference on Retroviruses and Opportunistic Infections, Washington D.C., U.S.A., 1996; Abstract#351. This reference is a book and is not being submitted at this time but if the Examiner requests the reference it will be submitted.

Florence "Non-ionic surfactant vesicles: preparation and characterization." In: Gregoriadis G. ed. Liposome Technology. Liposome Preparations and Related Techniques. 2nd cd. vol. I. CRC Press, 1993. This reference is a book and is not being submitted at this time but if the Examiner requests the reference it will be submitted.

Goodman's & Gilman's '"The Pharmacological Basis of Therapeutics" Eds. Hardman et 01., 9th Edition, Pubi. McGraw Hill, 1996; chapters 43 through 50. This reference is a book and is not being submitted at this time but if the Examiner requests the reference it will be submitted.

Hamouda et al., "Microbiocidal effects of liposome-like microemulsions on pathogenic Gram negative bacteria." In: American Society for Microbiology, 98th General Meeting, Atlanta, Georgia, U.S.A., 1998; Abstract A-52.

Maha and Igarashi "The effect of nonionic detergent on dengue and Japanese encephalitis virus antigens in antigen detection ELISA and IgM-capture ELISA." Southeast Asian J Trop Med Pub Health 1997; 28: 718-722. This reference is a book and is not being submitted at this time but if the Examiner requests the referenc it will be submitted.

Eriksson et al., "Virus validation of plasma-derived products produced by Pharmacia, with particular reference to immuno Globulins." Blood Coagulation and Fibtinolysis 1994; 5 (Suppl. 3): S37-S44. This reference is a book and is not being submitted at this time but if the Examiner requests the reference it will be submitted.

Henrickson "Viral Pneumonia in Children" 1998 Seminars in Pediatric Infectious Disease vol. 9 No. 3 pp. 217-233.

Hamouda et al., "Microbicidal Effects of Lipsome-Like Nanoemulsion on Pathogenic Gram Negative Bacteria" 98th ASM General Meeting, Atlanta, Abstract # A-52 p. 47, American Society for Microbiology, 1998.

Alasri et al., "Sporicidal properties of peracetic acid and hydrogen peroxide, alone and in combination, in comparison with chlorine and formaldehyde for ultrafiltration membrane disinfection." 1993 Can. J. Microbiol 39: 52-60.

Baragi et al., "Transplantation of transdiced Chondrocytes protects articular cartilage from intedeukin 1-induced extracellular matrix degradation." 1995 J Clin Invest 96: 2454-2460.

Beauchamp et al., "A Critical review of the toxicology of glutaraldphyde." 1992 Crit. Rev. ToxicoL 22:143-174.

Berkelman et al., "Emerging infectious diseases in the United States, 1993." 1994 J Infect Dis. 170(2):272-7.

Burdon et al., "Experimental infection of mice with *Bacillus cereus*: studies of pathogenesis and pathologic changes." 1967 J. Infect. Dis. 117:307-316.

Burdon and Wende "On the differentiation of anthrax bacilli from *Bacillus cereus*." 1960 J. Infect. Dis. 107: 224-234.

Dragon and Rennie "The ecology and anthrax spores: Tough but not invincible." 1995 Can. Vet. J. 36: 295-301.

Drobniewski "*Bacillus cereus* and related species." 1993 Clin. Microbiol. Rev. 6: 324-338.

Foster and Johnstone "Pulling the trigger: the mechanism of bacterial spore germination." 1990 MolecularMicrobiology 4:137-141.

Franz et al., "Clinical recognition and management of patients exposed to biological warfare agents." JAMA 1997; 278: 399-411.

Fritz et al., "Pathology of experimental anthrax in'the rhesus monkey." 1995 Lab. Invest. 73: 691-702.

Graham et al., "Characteristics of a human cell line transformed by DNA from human adenovirus type 5." 1977 J Gen Virol 36: 59-74.

Halvorson and Church, Biochemistry of Spores of Aerobic Bacilli with Special Reference to Germination, Bacteriol Rev 1957, 21:112.

Hamouda et al., "A novel surfactant nanoemulsion with broad-spectrum sporicidal activity against *Bacillus* species" 1999 Journal Infectious Disease 180:1939-1949.

Hayden et al., "Plaque inhibition assay for drug susceptibility testing of influenza viruses." Antimicrob Agents Chemother. 1980 17: 865-870.

Herlocher et al., "Sequence comparison of AIAA/6/60 influenza viruses: mutations, which may contribute to attenuation." Virus Res. 1996; 42:11-25.

Hermonat et al., "The spermicide nonoxynol-9 does not inactivate papillomavirus." Sexually Trans Dis 1992; 19: 203-205.

Hess et al., "Epidermal toxicity of disinfectants." Amer. J. Dent. 1991; 4: 51-56.

Hills, Chemical Factors in the Germination of Spore-bearing Aerobes: Observations on the Influence of Species, Strain and Conditions of Growth, 1950, J Gen Microbiol 4:38.

Horowitz et al., "Solvent/detergent-treated plasma: a vi rus-in activated substitute for fresh frozen plasma" 1992 Blood 79: 826-831.

Huang et al., "Antiviral activity of some natural and synthetic sugar analogues." 1991 FEBS Letters. 291: 199-202.

Ivins et al., "Experimental anthrax vaccines: efficacy of adjuvants combined with protective antigen against an aerosol *Bacillus anthracis* spore challenge in guinea pigs." 1995 Vaccine 13: 1779-1784.

Jackson et al., "PCR analysis of tissue samples from the 1979 Sverdlovsk anthrax victims: The presence of multiple *Bacillus anthracis* strains in 10 different victims." PNAS 1998; 95:1224-1229.

Karalvanova and Spiro "Sulphation of N-linked oligosacchaddes of vesicular stomatitis and influenza virus envelope glycoproteins: host cell specificity, subcellular localization and identification of substituted saccharides." Bioch J 1998; 329: 511-518.

Lamanna and Jones "Lethality for mice of vegetative and spore forms of *Bacillus cereus* and *Bacillus cereus*-like insect pathogens injected intraperitoneally and subcutaneously." J. Bact. 1963; 85: 532-535.

Lamb and Krug "Orthomyxoviride: The viruses and their replication." In: Fields BN. Knipe DM. Howley PM. eds. Fields Virology, 3rd ed., Philadelphia Pennsylvania, U.S.A., Lippincoft-Raven Publishers, 1996; 1353-1395.

Lee "Review: in vitro spermicidal tests." Contraception 1996; 54: 131-147.

Lim and Chae "A simple assay for DNA transfection by incubation of the cells in culture dishes with substrates for beta-galactosidase." 1989 Biotechniques 7: 576-579.

Lineaweaver et al., "Topical antimicrobial toxicity." Arch. Surg. 1985; 120: 267-270.

Mammen et al., "Effective inhibitors of hemagglutination by influenza virus synthesized from polymers having active ester groups. Insight into mechanism of inhibition." 1995 J Med Chem 38: 4179-4190.

Mendel et al., "Oral administration of a prodrug of the influenza virus neuraminidase inhibitor GS 4071 protects mice and ferrets against influenza infection" 1998 Antimicrob Agents Chemother 42: 640-646.

Meselson et al., "The Sverdlovsk anthrax outbreak of 1979." Science 1994; 266:1202-1208.

Mobley "Biological warfare in the twentieth century: lessons from the past, challenges for the future." Military Med. 1995; 160: 547-553.

Morgan "A brief review of formaldehyde carcinogenesis in relation to rat nasal pathology and human health risk assessment." ToxicoL PathoL 1997; 25: 291-307.

Mosmann J. Immun. Methods 1983, 65, 55-63 Mulder and Hers "Influenza." Wolter-Noordhoff Publishing, 1972.

O'Hagan "Recent advances in vaccine adjuvants for systemic and mucosal administration." J Pharmacy Pharmacol 1998; 50: 1-10.

Pile et al., "Anthrax as a potential biological weapon." Arch. Intern. Med. 1998; 158: 429-434.

Portocala et al., "Immunoelectrophoretic characterization of Sendai virus antigens." Virologie 1976; 27: 261-264.

Russell "Bacterial spores and chemical sporicidal agents." Clin. Micro 1990; 3: 99-119.

Schulze "Effects of glycolysation on the properties and functions of influenza virus hemagglutinin." J Infect Dis 1997; 176 (Suppl. 1): S24-28.

Shibata "Germination of inactivated spores of *Bacillus cereus* T. Effect of preincubation with L-alanine or inosine on the subsequent germination." Japan. J. Microbiol. 1976; 20: 529-535.

Smith et al., "Dihydropyrancarboxamides related to Zanamivir: a new series of inhibitors of influenza virus sialidases. 1. Discovery, synthesis biological activity, and structure-activity relationships of 4-guanidino and 4-amino-4H-pyran-6-carboxamides." J Med Chem 1998; 41: 787-797.

Titball and Manchee "Factors affecting the germination of spores of *Bacillus anthracis*." J. Appi. Bact. 1987; 62: 269-273.

Waghorn and Goa, "Zanamivir." Drugs 1998; 55: 721-725.

Welkos and Friedlander "Pathogenesis and genetic control of resistance to the Sterne strain of *Bacillus anthracis*." Microb. Path. 1988; 4: 53-69.

Welkos et al., "Differences in susceptibility of inbred mice to *Bacillus anthracis*" Infect. Immun. 1986; 51: 795-800.

Yanagita, Biochemical Aspects on the Germination of Conidiospores of *Aspergillus niger*, 1957, Arch Mikrobiol 26:329-344.

Zeitlin et al., "Tests of vaginal microbicides in the mouse genital herpes model." Contraception 1997; 56: 329-335.

http://www.answers.com/topic/emulsion.

\* cited by examiner

Time Zero

Control Spores
1 hour | 2 hours | 4 hours

BCTP-Treated Spores
1 hour | 2 hours | 4 hours | 6 hours

% Sporicidal activity in 4 hours at room temp.

FIGURE 16

FIGURE 18
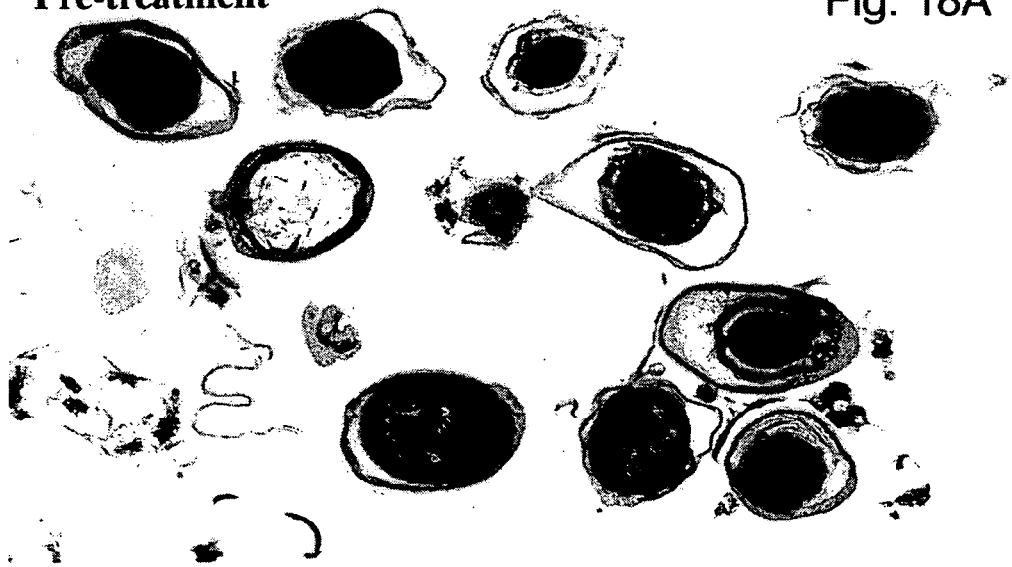
Pre-treatment  Fig. 18A
Post-treatment  Fig. 18B
1μm FIGURE 20
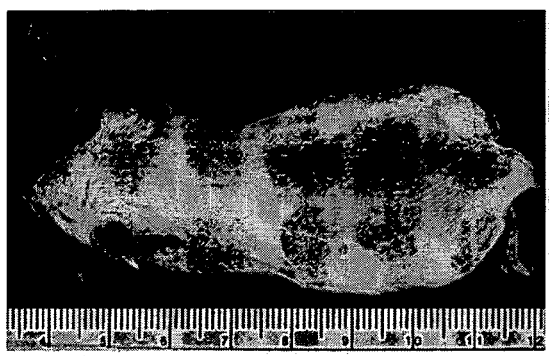
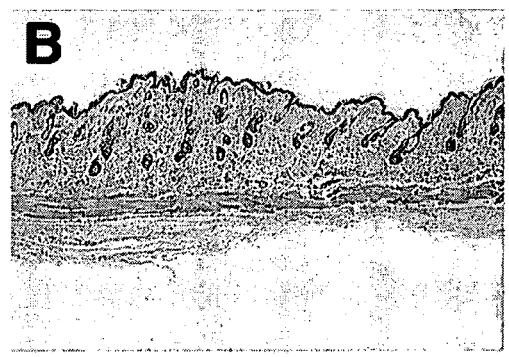
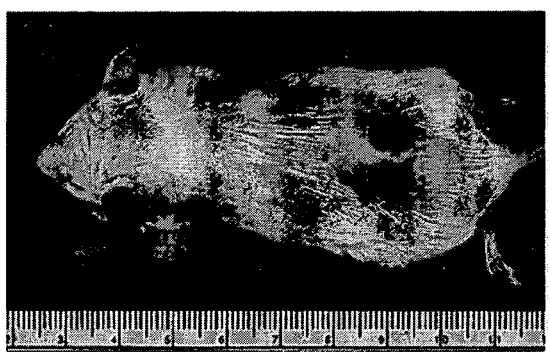
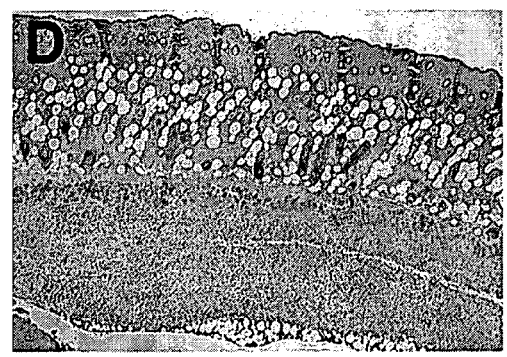
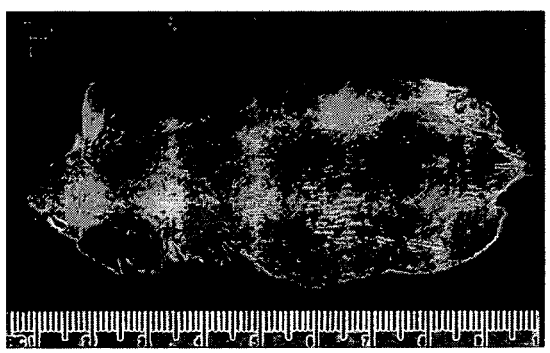
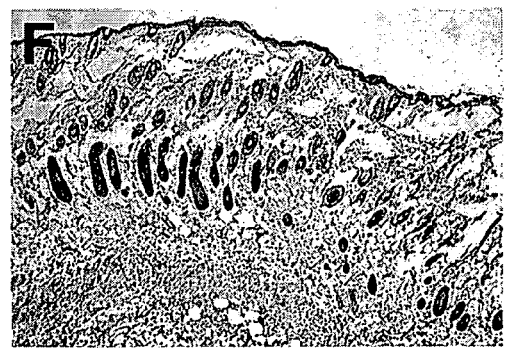

FIGURE 21
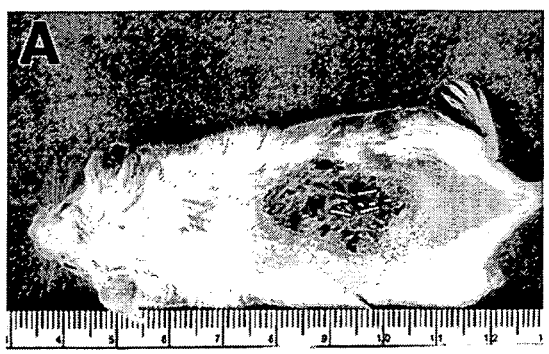
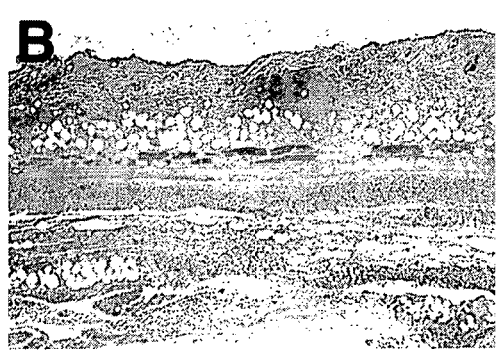
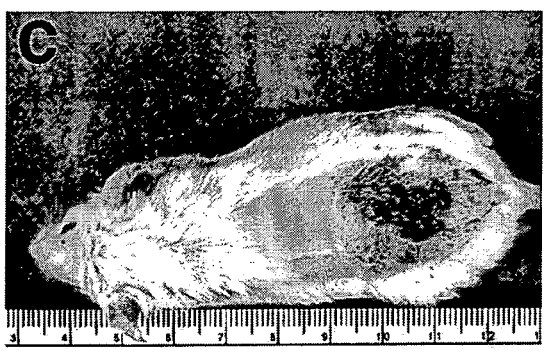
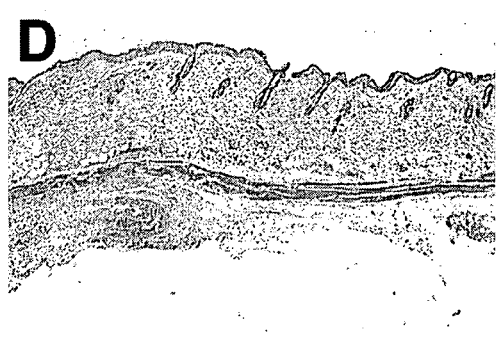
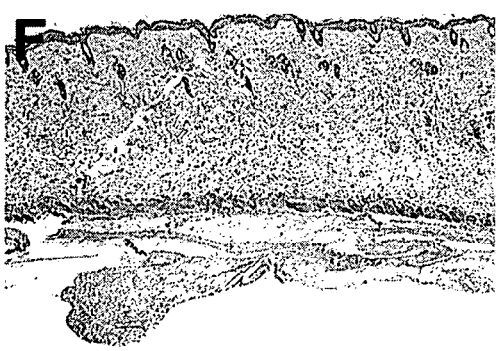

| MICROBE | |
|---|---|
| Bacteria | *Bacillus* (including *B. cereus, B. anthracis, B. circulans B. subtilis,* and *B. megaterium*); *Clostridium* (including *C. botulinum, C. tetani,* and *C. perfringens*); *E. coli*; *Haemophilus* (including *H. influenzae*); *Listeria monocytogenes*; *Neisseria* (including *N. gonorrhoeae*); *Proteus* (including *P. mirabilis*); *Psuedomonas* (including *P. aeruginosa*); *Shigella* (including *S. dysenteriae*); *Salmonella* (including *S. typhimurium*); *Staphlococcus* (including *S. aureus*) *Streptococcus* (including *S. agalactiae, S. pneumonia, S. pyogenes*); *Vibrio* (including *V. cholerae* classical and Eltor); and *Yersinea* (including *Y. enterocolitica* and *Y. pseudotuberculosis*); and |
| Enveloped virus | Influenza (including A, B and C); Herpes (including H. simplex); Sendai; Sindbis; and Pox virus (including vaccinia) |
| Fungi | *Candida* (including *C. albicans* and *C. tropicalis*); <u>*Trichophyton* (including *T. rubrum* and *T. mentagrophytes*);</u> <u>*Microsporum gypseum*;</u> <u>*Byssochlymus fulva*</u> |

FIG. 28

| Emulsion Formulas | | Result |
|---|---|---|
| ATB-X100 | | Effective against enveloped viruses, all Gram positive bacteria, all Gram negative bacteria and fungi |
| 8% | Triton X-100 | |
| 8% | Tributyl Phosphate | |
| 64% | Soybean Oil | |
| 1% | CPC | |
| 19% | DiH2O | |
| ATB-T60 | | Slightly less effective than ATB-X100; Effective against enveloped viruses, all Gram positive bacteria, all Gram negative bacteria and fungi |
| 5% | Tween 60 | |
| 8% | Tributyl Phosphate | |
| 64% | Soybean Oil | |
| 1% | CPC | |
| 22% | DiH2O | |
| ATB-XT160 | | Effective against enveloped viruses, all Gram positive bacteria, all Gram negative bacteria and fungi |
| 0.71% | Tween 60 | |
| 8% | Triton X-100 | |
| 8% | Tributyl Phosphate | |
| 64% | Soybean Oil | |
| 1% | CPC | |
| 18.29% | DiH2O | |
| ATB-X | | Effective against enveloped viruses, all Gram positive bacteria, all Gram negative bacteria and fungi; |
| 5% | Triton X-100 | |
| 5% | Tributyl Phosphate | |
| 40% | Soybean Oil | |
| 1% | CPC | |
| 49% | DiH2O | |

FIG. 29

| | | |
|---|---|---|
| 90% ATB-T22E/GE | | Effective against enveloped viruses, all Gram positive bacteria, all Gram negative bacteria and fungi; Increased safety for oral uptake |
| 1.8% | Triton X-100 | |
| 1.8% | Tyloxapol | |
| 7.2% | Ethanol (200 Proof) | |
| 57.6% | Soybean Oil | |
| 0.9% | CPC | |
| 0.09% | Peppermint Oil | |
| 5 mM | Inosine | |
| 5 mM | L-Alanine | |
| 10 mM | Ammonium Chloride | |
| 1 mM | Sodium Phosphate | |
| 13 mM | Sodium Chloride | |
| 30.61% | DiH2O | |
| | | |
| ATB-T3E | | Effective against all Gram positive bacteria, all Gram negative bacteria; Increased safety for oral uptake |
| 3% | Tyloxapol | |
| 8% | Ethanol | |
| 64% | Soybean Oil | |
| 1% | CPC | |
| 0.1% | Peppermint Oil | |
| 23.9% | DiH2O | |
| | | |
| ATB-X100E | | |
| 8% | Triton X-100 | |
| 8% | Ethanol | |
| 64% | Soybean Oil | |
| 1% | CPC | |
| 19% | DiH2O | |
| | | |
| ATB_Tween 20 E | | Effective against all Gram negative bacteria. |
| 5% | Tween 20 | |
| 1% | CPC | |
| 64% | Soybean Oil | |
| 8% | Ethanol | |
| 22% | DiH2O | |

FIG. 29 (CONTINUED)

| ATB-T22/GE | | Effective against enveloped viruses, all Gram positive bacteria, Gram negative bacteria, and bacterial spores |
|---|---|---|
| 2% | Triton X-100 | |
| 2% | Tyloxapol | |
| 8% | Tributyl Phosphate | |
| 64% | Soybean Oil | |
| 1% | CPC | |
| 0.1% | Peppermint Oil | |
| 5 mM | Inosine | |
| 5 mM | L-Alanine | |
| 10 mM | Ammonium Chloride | |
| 1 mM | Sodium Phosphate | |
| 13 mM | Sodium Chloride | |
| 22.9% | DiH2O | |
| 90% ATB-T22/GE | | Effective against enveloped viruses, Gram negative bacteria, all Gram positive bacteria, and bacterial spores; liquid enough to spray |
| 1.8% | Triton X-100 | |
| 1.8% | Tyloxapol | |
| 7.2% | Tributyl Phosphate | |
| 57.6% | Soybean Oil | |
| 0.9% | CPC | |
| 0.09% | Peppermint Oil | |
| 5 mM | Inosine | |
| 5 mM | L-Alanine | |
| 10 mM | Ammonium Chloride | |
| 1 mM | Sodium Phosphate | |
| 13 mM | Sodium Chloride | |
| 30.61% | DiH2O | |
| ATB-T22E | | Effective against enveloped viruses, all Gram positive bacteria, all Gram negative bacteria and fungi; Increased safety for oral uptake |
| 2% | Triton X-100 | |
| 2% | Tyloxapol | |
| 8% | Ethanol (200 Proof) | |
| 64% | Soybean Oil | |
| 1% | CPC | |
| 0.1% | Peppermint Oil | |
| 22.9% | DiH2O | |

FIG. 29 (CONTINUED)

| | | |
|---|---|---|
| ATB-T3 | | Effective against enveloped viruses, all Gram positive bacteria, all Gram negative bacteria and fungi |
| 3% | Tyloxapol | |
| 8% | Tributyl Phosphate | |
| 64% | Soybean Oil | |
| 1% | CPC | |
| 0.1% | Peppermint Oil | |
| 23.9% | DiH2O | |
| ATB-T3E pH7.1 | | Effective against, all Gram positive bacteria, all Gram negative bacteria and spores |
| 3% | Tyloxapol | |
| 8% | Ethanol | |
| 64% | Soybean Oil | |
| 1% | CPC | |
| 0.1% | Peppermint Oil | |
| 23.8% | DiH2O | |
| 0.1% | 10N NaOH | |
| ATB-T22 | | Effective against enveloped viruses, all Gram positive bacteria, all Gram negative bacteria and fungi; stable despite lower amount of detergent |
| 2% | Triton X-100 | |
| 2% | Tyloxapol | |
| 8% | Tributyl Phosphate | |
| 64% | Soybean Oil | |
| 1% | CPC | |
| 0.1% | Peppermint Oil | |
| 22.9% | DiH2O | |
| ATB-1X | | Effective against enveloped viruses, all Gram positive bacteria, all Gram negative bacteria, and bacterial spores |
| 8% | Triton X-100 | |
| 8% | Tributyl Phosphate | |
| 64% | Soybean Oil | |
| 1% | CPC | |
| 0.1% | Peppermint Oil | |
| 5 mM | Inosine | |
| 5 mM | L-Alanine | |
| 10 mM | Ammonium Chloride | |
| 1 mM | Sodium Phosphate | |
| 13 mM | Sodium Chloride | |
| 18.9% | DiH2O | |

FIG. 29 (CONTINUED)

| | | |
|---|---|---|
| ATB-X1001 | | Effective against enveloped viruses, all Gram positive bacteria, all Gram negative bacteria and fungi |
| 8% | Triton X-100 | |
| 8% | Tributyl Phosphate | |
| 50% | Soybean Oil | |
| 1% | CPC | |
| 33% | DiH2O | |
| ATB-X1002 | | Effective against enveloped viruses, all Gram positive bacteria, all Gram negative bacteria and fungi; more irritating than ATB-X100. |
| 8% | Triton X-100 | |
| 8% | Tributyl Phosphate | |
| 50% | Soybean Oil | |
| 2% | CPC | |
| 32% | DiH2O | |
| ATB-2 | | Effective against enveloped viruses, all Gram positive bacteria, all Gram negative bacteria and fungi |
| 0.1% | Peppermint Oil | |
| 8% | Triton X-100 | |
| 8% | Tributyl Phosphate | |
| 64% | Soybean Oil | |
| 2% | CPC | |
| 17.9% | DiH2O | |
| ATB-CPB | | Effective against enveloped viruses, all Gram positive bacteria, all Gram negative bacteria |
| 0.1% | Peppermint Oil | |
| 8% | Triton X-100 | |
| 8% | Tributyl Phosphate | |
| 64% | Soybean Oil | |
| 1% | CPB | |
| 18.9% | DiH2O | |
| ATB-1/2 | | Effective against enveloped viruses, all Gram positive bacteria, all Gram negative bacteria and fungi, demonstrates that dilution doesn't effective efficacy of ATB-X100 |
| 0.05% | Peppermint Oil | |
| 4% | Triton X-100 | |
| 4% | Tributyl Phosphate | |
| 32% | Soybean Oil | |
| 0.5% | CPC | |
| 59.45% | DiH2O | |

Log reduction of E. coli by various emulsions
(Rotator, 15min in media)

| Emulsion | 10% | 1% | 0.10% |
|---|---|---|---|
| 50% X8PC | 5.67 | 2.09 | 0 |
| D2P | 0.17 | 0 | 0 |
| EC | 5.81 | 5.81 | 4.42 |
| GC10 | 6.02 | 6.02 | 6.02 |
| $P_5C^*$ | 5.49 | 5.49 | 2.39 |
| $S_{60}8GL5$ | 0 | 0 | 0 |
| S8GL1B1 | 0 | 0 | 0 |
| S8P | 0.2 | 0.18 | 0.067 |
| $W_{20}10EA5^*$ | 0 | 0 | 0 |
| $W_{20}10ECH_3^*$ | 0 | 0 | 0 |
| $W_{20}10EQ_{100x}$ | 0 | 0 | 0 |
| $W_{20}10EQ_{10x}$ | 0 | 0 | 0 |
| $W_{20}5EC$ | 6.22 | 6.22 | 5.48 |
| $W_{60}PC$ | 5.81 | 5.81 | 2.62 |
| $W_{80}5EC$ | 6.13 | 6.13 | 3.97 |
| $X2Y2C^*$ | 5.64 | 5.64 | 2.37 |
| X2Y2EC | 5.61 | 5.61 | 5.61 |
| $X2Y2P_4C$ | 5.93 | 5.93 | 4 |
| X2Y2PC | 5.67 | 5.67 | 5.67 |
| X4Y4E | 0 | 0 | 0 |
| X8E | 0 | 0 | 0 |
| X8P BC | 5.93 | 4.41 | 0 |
| X8P CPB | 5.59 | 5.59 | 2.8 |
| X8P CPB | 4.26 | 0.35 | 0 |
| X8P CTAB | 4.04 | 0.16 | 0 |
| X8P Tannic acid | 3.84 | 0 | 0 |
| X8PC | 5.59 | 5.59 | 1.79 |
| X8PC2 | 5.59 | 5.59 | 4.42 |
| $X8W_{60}PC$ | 5.58 | 5.58 | 1.05 |
| Y3C | 5.48 | 5.48 | 3.54 |
| Y3E | 0.25 | 0.19 | 0.05 |
| Y3EC | 6.13 | 6.13 | 6.13 |
| Y3EVc5 | 0 | 0 | 0 |
| Y3PC | 5.31 | 5.31 | 5.31 |
| Y8EC | 5.81 | 5.81 | 4.62 |
| Y8EC S | 0.08 | 0.08 | 0.04 |

FIGURE 31B
Log reduction of B. globigii spores by various emulsions
(Rotator, 4 hours in germination enhnacers)

| Emulsion | 10% | 1% | 0.10% |
|---|---|---|---|
| 50% X8PC | 2.21 | 2.6 | 2.46 |
| D2P | 0.94 | 1.28 | 1.75 |
| S8P | 0.53 | 0.94 | 1.27 |
| $W_{80}4Y4E$ | 1.01 | 1.09 | 1.5 |
| $W_{80}4Y4EC$ | 1.84 | 2.46 | 2.62 |
| $W_{80}5E$ | 0.73 | 1.12 | 1.94 |
| $W_{80}5EC$ | 1.8 | 2.31 | 2.6 |
| X2E | 2.4 | 2.27 | 0.5 |
| X2E | 2.44 | 1.15 | 0.86 |
| X2Y2C | 2.63 | 2.37 | 4.22 |
| X2Y2E | 1.88 | 1.24 | 1.08 |
| X2Y2EC | 2.55 | 2.83 | 3.13 |
| X2Y2EC | 1.94 | 2.19 | 2.6 |
| $X2Y2P_4C$ | 2.78 | 2.71 | 3.44 |
| X2Y2PC | 2.93 | 2.72 | 4.11 |
| X2Y2PC | 2.67 | 2.57 | 3.73 |
| X2Y2PC | 2.8 | 2.71 | 3.95 |
| X2Y6E | 2.2 | 1.73 | 0.97 |
| X3E | 2.49 | 2.23 | 1.14 |
| X4E | 2.43 | 2.38 | 2.44 |
| X4E | 2.49 | 2.25 | 0.95 |
| X4Y4E | 2.61 | 1.89 | 1.31 |
| X5E | 2.44 | 2.51 | 0.41 |
| $X5P_5C$ | 2.39 | 2.42 | 2.62 |
| X6E | 2.44 | 2.64 | 0.92 |
| X6Y2E | 2.7 | 2.62 | 1.72 |
| X8E | 2.19 | 2.28 | 0.47 |
| X8E | 2.42 | 2.55 | 0.92 |
| X8E O | 1.26 | 1.32 | 0.96 |
| X8PC | 2.6 | 2.73 | 2.79 |
| X8PC2 | 2.41 | 2.47 | 2.72 |
| Y2PC* | 1.37 | 1.57 | 3.2 |
| Y3PC | 2.32 | 2.57 | 3.8 |
| Y3PC | 2.33 | 2.44 | 3.31 |
| Y8E | 0.17 | 0.3 | 0.59 |
| Y8E | 0.49 | 0.59 | 0.6 |
| Y8E O | 1.02 | 0.56 | 0.7 |
| Y8EC | 2.01 | 2.39 | 2.56 |
| Y8P | 0.89 | 0.57 | 0.64 |

FIGURE 31C

Log reduction of INF A pfu/ml treated with nanoemulsion series
as measured by plaque reduction assay (30 min incubation)

Logs of Reduction

| Compound | 1:10 | 1:100 | 1:1000 | |
|---|---|---|---|---|
| X2Y2E | 0 | 0 | 0 | |
| X4Y4E | 0 | 0 | 0 | |
| X6Y2E | 0 | 0 | 0 | |
| X2Y6E | 1 93 | 0 | 0 | |
| S608GL5 | 0 | 0 | 0 | |
| Y8E | 0 | 0 | 0 | |
| Y3E | 0 | 0 | 0 | |
| Y8ES | 0 | 0 | 0 | S= sorbic acid |
| Y8 | 0 | 0 | 0 | |
| X2E | 2.08 | 1 38 | 0 | |
| X3E | 2.6 | 0 | 0 | |
| X4E | 3.16 | 1.61 | 0 | |
| X5E | 3.16 | 1.61 | 0 | |
| X6E | 3.42 | 3.42 | 3.42 | |
| X8E | 3.86 | 3.86 | 0 | |
| X8E (unpurified oil) | 3.86 | 3 21 | 0 | |
| X8G | 2.74 | 2 74 | 0 | |
| X8B | 3.82 | 2 36 | 0 | B= Benzyl Benzoate |
| X8EO | 3.86 | 3 42 | 0 | O= Olive oil |
| D2P | 3.97 | 3.97 | 0.97 | |
| D2G | 3.82 | 3 82 | 0.00 | |
| S3Y3G STS5 | 2.26 | 0 | 0.00 | S= SDS |
| S8GL1B1 | 3.82 | 3.82 | 0.74 | S= SDS |
| S8G | 4.1 | 4.1 | 0.00 | S= SDS |
| S8P | 3.97 | 3.97 | 2.71 | S= SDS |
| $W_{80}$5E | 0 | 0 | 0 | |
| $W_{80}$4Y4E | 0 | 0 | 0 | |
| $W_{80}$8 | 0 | 0 | 0 | |
| $W_{20}$5E | 0 | 0 | 0 | |
| $W_{80}$4Y4EC | 3 | 3 | 2 | |
| $W_{80}$5EC | 3 | 3 | 3 | |
| $W_{20}$5EC | 3 | 3 | 3.3 | |
| X2Y2EC | 3 | 3 | 2 | |
| X2Y2PC | 3 | 3 | 3 | |
| X8PC | 4.98 | 4 98 | 4.98 | |
| X8GC | 4 68 | 4 68 | 4.68 | |
| X8EC | 4 1 | 4 1 | 1.97 | |
| Y8EC | 3 | 3 | 2 | |
| Y3EC | 3 | 3 | 2 | |
| Y3EC | 3 | 3 | 2.12 | |
| Y3PC | 3 | 3 | 2.63 | |
| EC | 3 | 3 | 3 | |
| GC | 4.14 | 4 14 | 4.14 | |
| ATB-EDTA | 3 | 3 | 1.98 | |
| Y2X2SPC | 1.10 | 1.10 | 0 | |

FIGURE 36 diH$_2$O

| Treatment type | Pre Treatment Count per sq ft | Post Treatment Count per sq ft | Runoff (5 minutes) |
|---|---|---|---|
| W$_{20}$5EC 50°C | 5.63 X 10$^7$ | 0 | 0 |
| W$_{20}$5EC RT | 8.05 X 10$^7$ | 0 | 6 X 10$^5$ |
| H$_2$O 50°C | 7.96 X 10$^7$ | 0 | too numerous to count |
| H$_2$O RT | 1.15 X 10$^8$ | 0 | too numerous to count |

Distilled Water

| Treatment type | Pre Treatment Count per sq ft | Post Treatment Count per sq ft | Runoff (5 minutes) |
|---|---|---|---|
| W$_{20}$5EC 50°C | 2.9 X 10$^8$ | 0 | 0 |
| W$_{20}$5EC 40°C | 1.7 X 10$^8$ | 3.46 X 10$^5$ | 1.8 X 10$^5$ |
| H$_2$O 50°C | 2.13 X 10$^7$ | 0 | 1.5 X 10$^8$ |
| H$_2$O 40°C | 1.3 X 10$^8$ | 2.3 X 10$^5$ | 6.7 X 10$^7$ |

Tap Water

| Treatment type | Pre Treatment Count per sq ft | Post Treatment Count per sq ft | Runoff (5 minutes) |
|---|---|---|---|
| W$_{20}$5EC 50°C | 1.4 X 10$^9$ | 0 | 3 X 10$^5$ |
| W$_{20}$5EC 40°C | 5.65 X 10$^7$ | 0 | 6 X 10$^5$ |
| W$_{20}$5EC RT | 1.9 X 10$^8$ | 5.76 X 10$^4$ | 1.26 X 10$^6$ |
| H$_2$O 50°C | 1.75 X 10$^8$ | 0 | 4.68 X 10$^7$ |
| H$_2$O 40°C | 6.35 X 10$^7$ | 0 | 2.2 X 10$^8$ |
| H2O RT | 2.74 X 10$^6$ | 4 X 10$^5$ | 1.5 X 10$^8$ |

ANTIMICROBIAL NANOEMULSION COMPOSITIONS AND METHODS

The following application is a Continuation of U.S. application No. 10/179,547, filed Jun. 25, 2002, issued as U.S. Pat. No. 7,655,252 Feb. 2, 2010, which is a Continuation-in-Part of U.S. application Ser. No. 09/965,447, filed Sep. 27, 2001, issued as U.S. Pat. No. 6,635,676 Oct. 21, 2003, which is a Continuation-in-Part of U.S. application Ser. No. 09/891,086, filed Jun. 25, 2001, issued as U.S. Pat. No. 6,559,189 May 6, 2003, which is a Continuation-in-Part of U.S. application Ser. No. 09/751,059, filed Dec. 29, 2000, issued as U.S. Pat. No. 7,767,216 Aug. 3, 2010, which is a Continuation-in-part of U.S. application Ser. No. 09/561,111, filed Apr. 28, 2000, issued as U.S. Pat. No. 6,506,803 Jan. 14, 2003, which is both 1) a Continuation-in-part of U.S. application Ser. No. 09/474,866, filed Dec. 30, 1999, and 2) which claims priority to U.S. provisional application No. 60/131,638, filed Apr. 28, 1999. Each of these applications is incorporated herein by reference in their entireties.

This invention was made with government support under MDA972-97-1-0007 awarded by the United States Defense Advanced Research Projects Agency (DARPA). The government has certain rights in the invention.

FIELD OF THE INVENTION

The present invention relates to compositions and methods for decreasing the infectivity, morbidity, and rate of mortality associated with a variety of pathogens. The present invention also relates to methods and compositions for decontaminating areas, samples, solutions, and foodstuffs colonized or otherwise infected by pathogens and microorganisms.

BACKGROUND OF THE INVENTION

Pathogens such as bacteria, fungi, viruses, and bacterial spores are responsible for a plethora of human and animal ills, as well as contamination of food and biological and environmental samples. The first step in microbial infections of animals is generally attachment or colonization of skin or mucus membranes, followed by subsequent invasion and dissemination of the infectious microbe. The portals of entry of pathogenic bacteria are predominantly the skin and mucus membranes.

In particular, bacteria of the *Bacillus* genus form stable spores that resist harsh conditions and extreme temperatures. Contamination of farmlands with *B. anthracis* leads to a fatal disease in domestic, agricultural, and wild animals (See e.g., Dragon and Rennie, Can. Vet. J. 36:295 [1995]). Human infection with this organism usually results from contact with infected animals or infected animal products (See e.g., Welkos et al., Infect. Immun. 51:795 [1986]). Human clinical syndromes include a pulmonary form that has a rapid onset and is frequently fatal. The gastrointestinal and cutaneous forms of anthrax, although less rapid, can result in fatalities unless treated aggressively (See e.g., Franz et al., JAMA 278:399 [1997]; and Pile et al., Arch. Intern. Med. 158:429 [1998]). *Bacillus anthracis* infection in humans is no longer common due to effective animal controls that include vaccines, antibiotics and appropriate disposal of infected livestock. However, animal anthrax infection still represents a significant problem due to the difficulty in decontamination of land and farms. In addition, there is concern about human infection brought about by warfare and/or terrorist activities.

While an anthrax vaccine is available (See e.g., Ivins et al., Vaccine 13:1779 [1995]) and can be used for the prevention of classic anthrax, genetic mixing of different strains of the organism can render the vaccine ineffective (See e.g., Mobley, Military Med. 160:547 [1995]). The potential consequences of the use of Anthrax spores as a biological weapon was demonstrated by the accidental release of *Bacillus anthracis* from a military microbiology laboratory in the former Soviet Union. Seventy-seven cases of human anthrax, including 66 deaths, were attributed to the accident. Some anthrax infections occurred as far as 4 kilometers from the laboratory (See e.g., Meselson et al., Science 266:1202 [1994]). Genetic analysis of infected victims revealed the presence of either multiple strains or a genetically altered *B. anthracis* (See e.g., Jackson et al., Proc. Nat. Acad. of Sci. U.S.A. 95:1224 [1998]).

Additionally, other members of the *Bacillus* genus are also reported to be etiological agents for many human diseases. *Bacillus cereus* is a common pathogen. It is involved in food borne diseases due to the ability of the spores to survive cooking procedures. It is also associated with local sepsis and wound and systemic infection (See e.g., Drobniewski, Clin. Micro. Rev. 6:324 [1993]). Many bacteria readily develop resistance to antibiotics. An organism infected with an antibiotic-resistant strain of bacteria faces serious and potentially life-threatening consequences.

Examples of bacteria that develop resistance include *Staphylococcus* that often cause fatal infections, *Pneumococci* that cause pneumonia and meningitis; *Salmonella* and *E. coli* that cause diarrhea; and *Enterococci* that cause blood-stream, surgical wound and urinary tract infections (See e.g., Berkelman et. al., J. Infcet. Dis. 170(2):272 [1994]).

Although an invaluable advance, antibiotic and antimicrobial therapy suffers from several problems, particularly when strains of various bacteria appear that are resistant to antibiotics. In addition, disinfectants/biocides (e.g., sodium hypochlorite, formaldehyde and phenols) that are highly effective against *Bacillus* spores, are not well suited for decontamination of the environment, equipment, or casualties. This is due to toxicity that leads to tissue necrosis and severe pulmonary injury following inhalation of volatile fumes. The corrosive nature of these compounds also renders them unsuitable for decontamination of sensitive equipment (See e.g., Alasri et al., Can. J. Micro. 39:52 [1993]; Beauchamp et al., Crit. Rev. Tox. 22:143 [1992]; Hess et al., Amer. J. dent. 4:51 [1991]; Lineaweaver et al., Arch. Surg. 120:267 [1985]; Morgan, Tox. Path. 25:291 [1997]; and Russell, Clin. Micro. 3; 99 [1990]).

Influenza A virus is a common respirator pathogen that is widely used as a model system to test anti-viral agents in vitro (See e.g., Karaivanova and Spiro, Biochem. J. 329:511 [1998]; Mammen et al., J. Med. Chem. 38:4179 [1995]; and Huang et al., FEBS Letters 291:199 [1991]), and in vivo (See e.g., Waghorn and Goa, Drugs 55:721 [1998]; Mendel et al., Antimicrob. Agents Chemother. 42:640 [1998]; and Smith et al., J. med. Chem. 41:787 [1998]). The envelope glycoproteins, hemagglutinin (HA) and neuraminidase (NA), which determine the antigenic specificity of viral subtypes, are able to readily mutate, allowing the virus to evade neutralizing antibodies. Current anti-viral compounds and neuraminidase inhibitors are minimally effective and viral resistance is common.

Clearly, antipathogenic compositions and methods that decrease the infectivity, morbidity, and mortality associated with pathogenic exposure are needed. Such compositions and methods should preferably not have the undesirable properties of promoting microbial resistance, or of being toxic to the recipient.

SUMMARY OF THE INVENTION

The present invention relates to compositions and methods for decreasing the infectivity, morbidity, and rate of mortality associated with a variety of pathogens. The present invention also relates to methods and compositions for decontaminating areas, samples, solutions, and foodstuffs colonized or otherwise infected by pathogens and microorganisms. Certain embodiments of the present compositions are nontoxic and may be safely ingested by humans and other animals. Additionally, certain embodiments of the present invention are chemically stable and non-staining.

In some embodiments, the present invention provides compositions and methods suitable for treating animals, including humans, exposed to pathogens or the threat of pathogens. In some embodiments, the animal is contacted with effective amounts of the compositions prior to exposure to pathogenic organisms. In other embodiments, the animal is contacted with effective amounts of the compositions after exposure to pathogenic organisms. Thus, the present invention contemplates both the prevention and treatment of microbiological infections.

In other embodiments, the present invention provides compositions and methods suitable for decontaminating solutions and surfaces, including organic and inorganic samples that are exposed to pathogens or suspected of containing pathogens. In still other embodiments of the present invention, the compositions are used as additives to prevent the growth of harmful or undesired microorganisms in biological and environmental samples.

In preferred embodiments, decreased pathogenic organism infectivity, morbidity, and mortality is accomplished by contacting the pathogenic organism with an oil-in-water nanoemulsion comprising an oil phase, an aqueous phase, and at least one other component. In some preferred embodiments, the emulsion further comprises a solvent. In some preferred embodiments, the solvent comprises an organic phosphate solvent. In still other embodiments, the organic phosphate-based solvent comprises dialkyl phosphates or trialkyl phosphates (e.g., tributyl phosphate). In still other preferred embodiments, the emulsion further comprises an alcohol. In preferred embodiments that employ solvents, the solvent is provided in the oil phase of the composition.

In some embodiments, the compositions of the present invention further comprise one or more surfactants or detergents. In some embodiments, it is contemplated that the surfactant is a non-anionic detergent. In preferred embodiments, the non-anionic detergent is a polysorbate surfactant. In other embodiments, the non-anionic detergent is a polyoxyethylene ether. Surfactants that find use in the present invention include, but are not limited to surfactants such as the TWEEN, TRITON, and TYLOXAPOL families of compounds.

In certain other embodiments, the compositions of the present invention further comprise one or more cationic halogen containing compounds, including but not limited to, cetylpyridinium chloride. In yet other embodiments, the compositions of the present invention further comprise one or more compounds that promote or enhance the germination ("germination enhancers") of certain microorganism, and in particular the spore form of certain bacteria. Germination enhancers contemplated for formulation with the inventive compositions include, but are not limited to, L-alanine, Inosine, $CaCl_2$, and $NH_4Cl$, and the like. In still further embodiments, the compositions of the present invention further comprise one or more compounds that increase the interaction ("interaction enhancers") of the composition with microorganisms (e.g., chelating agents like ethylenediaminetetraacetic acid, or ethylenebis(oxyethylenenitrilo)tetraacetic acid in a buffer). Additionally, in still other embodiments of the present invention, the formulations further comprise coloring or flavoring agents (e.g., dyes and peppermint oil).

In some embodiments, the composition further comprises an emulsifying agent to aid in the formation of emulsions. Emulsifying agents include compounds that aggregate at the oil/water interface to form a kind of continuous membrane that prevents direct contact between two adjacent droplets. Certain embodiments of the present invention feature oil-in-water emulsion compositions that may readily be diluted with water to a desired concentration without impairing their anti-pathogenic properties.

In addition to discrete oil droplets dispersed in an aqueous phase, oil-in-water emulsions can also contain other lipid structures, such as small lipid vesicles (e.g., lipid spheres that often consist of several substantially concentric lipid bilayers separated from each other by layers of aqueous phase), micelles (e.g., amphiphilic molecules in small clusters of 50-200 molecules arranged so that the polar head groups face outward toward the aqueous phase and the apolar tails are sequestered inward away from the aqueous phase), or lamellar phases (lipid dispersions in which each particle consists of parallel amphiphilic bilayers separated by thin films of water).

These lipid structures are formed as a result of hydrophobic forces that drive apolar residues (e.g., long hydrocarbon chains) away from water. The above lipid preparations can generally be described as surfactant lipid preparations (SLPs). SLPs are minimally toxic to mucous membranes and are believed to be metabolized within the small intestine (See e.g., Hamouda et al., J. Infect. Disease 180:1939 [1998]). SLPs are non-corrosive to plastics and metals in contrast to disinfectants such as bleach. As such, formulations of the present invention based on SLPs are contemplated to be particularly useful against bacteria, fungi, viruses and other pathogenic entities.

Certain embodiments of the present invention contemplate methods for decreasing the infectivity of microorganisms (e.g., pathogenic agents) comprising contacting the pathogen with a composition comprising an oil-in-water emulsion. In some preferred embodiments, the emulsion is in the form of an oil phase distributed in an aqueous phase with a surfactant, the oil phase includes an organic phosphate based solvent and a carrier oil. In some embodiments, two or more distinct emulsions are exposed to the pathogen. In preferred embodiments, the emulsions are fusigenic and/or lysogenic. In preferred embodiments, the oil phase used in the method comprises a non-phosphate based solvent (e.g., an alcohol).

In specific embodiments, the contacting is performed for a time sufficient to kill the pathogenic agent or to inhibit the growth of the agent. In other embodiments, the present invention provides a method of decontaminating an environmental surface harboring harmful or undesired pathogens. In one such embodiment, the pathogenic agent is associated with an environmental surface and the method comprises contacting the environmental surface with an amount of the composition sufficient for decontaminating the surface. While it may be so desired, decontamination need not result in total elimination of the pathogen. In some embodiments, the compositions and methods further comprise dyes, paints, and other marking and identification compounds to as to ensure that a treated surface has been sufficiently treated with the compositions of the present invention.

In certain embodiments, an animal is treated internally with a composition of the present invention. In some preferred embodiments, the contacting is via intradermal, subcutaneous, intramuscular or intraperitoneal injection. In other embodiments, the contacting is via oral, nasal, buccal, rectal, vaginal or topical administration. When the present compositions are administered as pharmaceuticals, it is contemplated that the compositions further comprise pharmaceutically acceptable adjutants, excipients, stabilizers, diluents, and the like. In still further embodiments, the present invention contemplates compositions further comprising additional pharmaceutically acceptable bioactive molecules (e.g., antibodies, antibiotics, means for nucleic acid transfection, vitamins, minerals, co-factors, etc.).

In some preferred embodiments, the present invention provides a composition comprising an oil-in-water emulsion, said oil-in-water emulsion comprising a discontinuous oil phase distributed in an aqueous phase, a first component comprising an alcohol or glycerol, and a second component comprising a surfactant or a halogen-containing compound. The aqueous phase can comprise any type of aqueous phase including, but not limited to, water (e.g., diH$_2$O, distilled water, tap water) and solutions (e.g., phosphate buffered saline solution). The oil phase can comprise any type of oil including, but not limited to, plant oils (e.g., soybean oil, avocado oil, flaxseed oil, coconut oil, cottonseed oil, squalene oil, olive oil, canola oil, corn oil, rapeseed oil, safflower oil, and sunflower oil), animal oils (e.g., fish oil), flavor oil, water insoluble vitamins, mineral oil, and motor oil. In some preferred embodiments, the oil phase comprises 30-90 vol % of the oil-in-water emulsion (i.e., constitutes 30-90% of the total volume of the final emulsion), more preferably 50-80%. While the present invention in not limited by the nature of the alcohol component, in some preferred embodiments, the alcohol is ethanol or methanol. Furthermore, while the present invention is not limited by the nature of the surfactant, in some preferred embodiments, the surfactant is a polysorbate surfactant (e.g., TWEEN 20, TWEEN 40, TWEEN 60, and TWEEN 80), a pheoxypolyethoxyethanol (e.g., TRITON X-100, X-301, X-165, X-102, and X-200, and TYLOXAPOL) or sodium dodecyl sulfate. Likewise, while the present invention is not limited by the nature of the halogen-containing compound, in some preferred embodiments, the halogen-containing compound comprises a cetylpyridinium halides, cetyltrimethylammonium halides, cetyldimethylethylammonium halides, cetyldimethylbenzylammonium halides, cetyltributylphosphonium halides, dodecyltrimethylammonium halides, tetradecyltrimethylammonium halides, cetylpyridinium chloride, cetyltrimethylammonium chloride, cetylbenzyldimethylammonium chloride, cetylpyridinium bromide, cetyltrimethylammonium bromide, cetyldimethylethylammonium bromide, cetyltributylphosphonium bromide, dodecyltrimethylammonium bromide, or tetradecyltrimethylammonium bromide.

The emulsions may further comprise third, fourth, fifth, etc. components. In some preferred embodiments, an additional component is a surfactant (e.g., a second surfactant), a germination enhancer, a phosphate based solvent (e.g., tributyl phosphate), a neutramingen, L-alanine, ammonium chloride, trypticase soy broth, yeast extract, L-ascorbic acid, lecithin, p-hyroxybenzoic acid methyl ester, sodium thiosulate, sodium citrate, inosine, sodium hyroxide, dextrose, and polyethylene glycol (e.g., PEG 200, PEG 2000, etc.).

The present invention also provides non-toxic, non-irritant, a composition comprising an oil-in-water emulsion, said oil-in-water emulsion comprising a quaternary ammonium compound, wherein said oil-in-water emulsion is antimicrobial against bacteria, virus, fungi, and spores. In some preferred embodiments, the oil-in-water emulsion has no detectable toxicity to plants or animals (e.g., to humans). In other preferred embodiments, the oil-in-water emulsion causes no detectable irritation to plants or animals (e.g., to humans). In some embodiments, the oil-in-water emulsion further comprises any of the components described above. Quaternary ammonium compounds include, but are not limited to, N-alkyldimethyl benzyl ammonium saccharinate, 1,3,5-Triazine-1,3,5(2H,4H,6H)-triethanol; 1-Decanaminium, N-decyl-N,N-dimethyl-, chloride (or) Didecyl dimethyl ammonium chloride; 2-(2-(p-(Diisobuyl)cresosxy)ethoxy)ethyl dimethyl benzyl ammonium chloride; 2-(2-(p-(Diisobutyl)phenoxy)ethoxy)ethyl dimethyl benzyl ammonium chloride; alkyl 1 or 3 benzyl-1-(2-hydroxethyl)-2-imidazolinium chloride; alkyl bis(2-hydroxyethyl)benzyl ammonium chloride; alkyl demethyl benzyl ammonium chloride; alkyl dimethyl 3,4-dichlorobenzyl ammonium chloride (100% C12); alkyl dimethyl 3,4-dichlorobenzyl ammonium chloride (50% C14, 40% C12, 10% C16); alkyl dimethyl 3,4-dichlorobenzyl ammonium chloride (55% C14, 23% C12, 20% C16); alkyl dimethyl benzyl ammonium chloride; alkyl dimethyl benzyl ammonium chloride (100% C14); alkyl dimethyl benzyl ammonium chloride (100% C16); alkyl dimethyl benzyl ammonium chloride (41% C14, 28% C12); alkyl dimethyl benzyl ammonium chloride (47% C12, 18% C14); alkyl dimethyl benzyl ammonium chloride (55% C16, 20% C14); alkyl dimethyl benzyl ammonium chloride (58% C14, 28% C16); alkyl dimethyl benzyl ammonium chloride (60% C14, 25% C12); alkyl dimethyl benzyl ammonium chloride (61% C11, 23% C14); alkyl dimethyl benzyl ammonium chloride (61% C12, 23% C14); alkyl dimethyl benzyl ammonium chloride (65% C12, 25% C14); alkyl dimethyl benzyl ammonium chloride (67% C12, 24% C14); alkyl dimethyl benzyl ammonium chloride (67% C12, 25% C14); alkyl dimethyl benzyl ammonium chloride (90% C14, 5% C12); alkyl dimethyl benzyl ammonium chloride (93% C14, 4% C12); alkyl dimethyl benzyl ammonium chloride (95% C16, 5% C18); alkyl dimethyl benzyl ammonium chloride (and) didecyl dimethyl ammonium chloride; alkyl dimethyl benzyl ammonium chloride (as in fatty acids); alkyl dimethyl benzyl ammonium chloride (C12-C16); alkyl dimethyl benzyl ammonium chloride (C12-C18); alkyl dimethyl benzyl and dialkyl dimethyl ammonium chloride; alkyl dimethyl dimethybenzyl ammonium chloride; alkyl dimethyl ethyl ammonium bromide (90% C14, 5% C16, 5% C12); alkyl dimethyl ethyl ammonium bromide (mixed alkyl and alkenyl groups as in the fatty acids of soybean oil); alkyl dimethyl ethylbenzyl ammonium chloride; alkyl dimethyl ethylbenzyl ammonium chloride (60% C14); alkyl dimethyl isoproylbenzyl ammonium chloride (50% C12, 30% C14, 17% C16, 3% C18); alkyl trimethyl ammonium chloride (58% C18, 40% C16, 1% C14, 1% C12); alkyl trimethyl ammonium chloride (90% C18, 10% C16); alkyldimethyl(ethylbenzyl) ammonium chloride (C12-18); Di-(C8-10)-alkyl dimethyl ammonium chlorides; dialkyl dimethyl ammonium chloride; dialkyl dimethyl ammonium chloride; dialkyl dimethyl ammonium chloride; dialkyl methyl benzyl ammonium chloride; didecyl dimethyl ammonium chloride; diisodecyl dimethyl ammonium chloride; dioctyl dimethyl ammonium chloride; dodecyl bis(2-hydroxyethyl) octyl hydrogen ammonium chloride; dodecyl dimethyl benzyl ammonium chloride; dodecylcarbamoyl methyl dimethyl benzyl ammonium chloride; heptadecyl hydroxyethylimidazolinium chloride; hexahydro-1,3,5-thris(2-hydroxyethyl)-s-triazine; myristalkonium chloride (and) Quat RNIUM 14; N,N-Dimethyl-2-hydroxypropylammonium chloride polymer; n-alkyl dimethyl benzyl ammonium chloride; n-alkyl dimethyl ethylbenzyl ammonium chloride; n-tetradecyl dimethyl benzyl ammonium chloride monohydrate; octyl decyl dimethyl ammonium chloride; octyl dodecyl dimethyl ammonium chloride; octyphenoxyethoxyethyl dimethyl benzyl ammonium chloride; oxydiethylenebis (alkyl dimethyl ammonium chloride); quaternary ammonium compounds, dicoco alkyldimethyl, chloride; trimethoxysily propyl dimethyl octadecyl ammonium chloride; trimethoxysilyl quats, trimethyl dodecylbenzyl ammonium chloride; n-dodecyl dimethyl ethylbenzyl ammonium chloride; n-hexadecyl dimethyl benzyl ammonium chloride; n-tetradecyl dimethyl benzyl ammonium chloride; n-tetradecyl dimethyl ethylbenzyl ammonium chloride; and n-octadecyl dimethyl benzyl ammonium chloride.

The present invention also provides methods of making each of the emulsions disclosed herein. For example, the present invention provides a method of making a oil-in-water emulsion comprising emulsifying a mixture, said mixture comprising an oil, an aqueous solution, a first component comprising an alcohol or glycerol, and a second component comprising a surfactant or a halogen-containing compound.

The present invention further provides methods for protecting (e.g., protecting from contamination of a microorganism) or decontaminating an area (e.g., decontaminating an area by removing or reducing the number of microorganisms in the area) comprising exposing the area to a composition comprising an oil-in-water emulsion (e.g., any of the oil-in-water emulsions described herein). The method may be applied to any type of area. For example, in some embodiments, the area comprises a solid surface (e.g., a medical device), a solution, the surface of an organism (e.g., an external or internal portion of a human), or a food product.

The present invention also provides methods for modifying any of the emulsions described herein, comprising: providing the emulsion and adding or removing a component from the emulsion to produce a modified emulsion. In some embodiments, the method further comprises the step of testing the modified emulsion in a biological assay (e.g., an antimicrobial assay to determine the effectiveness of the emulsion at reducing the amount of microorganisms associated with a treated area). The present invention also contemplates methods of using such modified emulsion in commerce. For example, in some embodiments, the method further comprises the step of advertising the sale of the modified emulsion and/or selling the modified emulsion.

The present invention also provides systems comprising a delivery system (e.g., a container, dispenser, packaging etc.) containing any of the oil-in-water emulsions described herein. The present invention further comprises a system comprising a material in contact with any of the oil-in-water emulsions described herein. The present invention is not limited by the nature of the material in contact with the emulsion. For example, materials include, but are not limited to, medical devices, solutions, food products, cleaning products, motor oils, creams, and biological materials (e.g., human tissues).

DESCRIPTION OF THE FIGURES

The following figures form part of the present specification and are included to further demonstrate certain aspects and embodiments of the present invention. The invention may be better understood by reference to one or more of these figures in combination with the description of specific embodiments presented herein.

FIG. 16 illustrates the sporicidal activity of BCTP against 4 different *Bacillus* species compared to that of $X_8W_{60}PC$ against 2 *Bacillus* species. BCTP showed a significant sporicidal activity after 4 hours of treatment against *Bacillus cereus, Bacillus circulans*, and *Bacillus megaterium* spores, but not against *Bacillus subtilis* spores. $X_8W_{60}PC$, in 4 hours, showed more effective killing against *B. cereus* and also had a sporicidal activity against *B. subtilis* which was resistant to BCTP.

FIG. 18 depicts electron micrographs of *Bacillus cereus* spores pre- and post-treatment with BCTP. Note, the uniform density in the cortex and the well-defined spore coat before treatment with BCTP. Spores after 4 hours of BCTP treatment show disruption in both the spore coat and the cortex with loss of core components.

FIG. 20A-FIG. 20F depict gross and histologic photographs of animals injected subcutaneously with different combinations of BCTP and *B. cereus* spores. FIG. 20A and FIG. 20B illustrate animals that were injected with BCTP alone at a dilution of 1:10. There was no gross tissue damage and histology showed no inflammation. FIG. 20C and FIG. 20D illustrate animals that were injected with $4 \times 10^7$ *Bacillus cereus* spores alone subcutaneously. A large necrotic area resulted with an average area of 1.68 cm². Histology of this area showed essentially complete tissue necrosis of the epidermis and dermis including subcutaneous fat and muscle. FIG. 20E and FIG. 20F depict mice that were injected with $4 \times 10^7$ *Bacillus* spores which had been immediately premixed with the BCTP nanoemulsion at final dilution 1:10. These animals showed minimal skin lesions with average area 0.02 cm$^2$ (an approximate 98% reduction from those lesions resulting from an untreated infection with spores). Histology in FIG. 20F indicates some inflammation, however most of the cellular structures in the epidermis and dermis were intact. All histopathology is shown at 4× magnification.

FIG. 21A-FIG. 21F depict gross and histological photographs of animals with experimental wounds infected with *Bacillus cereus* spores. FIG. 21A and FIG. 21B depict mice with experimental wounds that were infected with $2.5\times10^7$ *Bacillus cereus* spores but not treated. Histological examination of these wounds indicated extensive necrosis and a marked inflammatory response. FIG. 21C and FIG. 21D depict mice with wounds that were infected with $2.5\times10^7$ *Bacillus cereus* spores and irrigated 1 hour later with saline. By 48 hours, there were large necrotic areas surrounding the wounds with an average area of 4.86 $cm^2$. In addition, 80% of the animals in this group died as a result of the infection. Histology of these lesions indicated total necrosis of the dermis and subdermis and large numbers of vegetative *Bacillus* organisms. FIG. 21E and FIG. 21F depict mice with wounds that were infected with $2.5\times10^7$ *Bacillus cereus* spores and irrigated 1 hour later with a 1:10 dilution of BCTP. There were small areas of necrosis adjacent to the wounds (0.06 $cm^2$) which was reduced 98% compared to animals receiving spores and saline irrigation. In addition, only 20% of animals died from these wounds. Histology of these lesions showed no evidence of vegetative *Bacillus* illustrates several particular embodiments the various emulsions of the present invention.

FIG. 22 illustrates the inhibition of influenza A infection by surfactant lipid preparations. FIG. 22A represents BCTP, $W_{80}$8P, SS, and NN; FIG. 22B: BCTP and SS. Virus was incubated with SLPs for 30 min. and subsequently diluted and overlaid on cells. Inhibition of influenza A infection was measured using cellular ELISA. Each data point represents the mean of three replicates +/−one standard error.

FIG. 23 illustrates the efficacy of BCTP as an anti-influenza agent as compared to TRITON X-100. Influenza A virus was treated with BCTP, tri(n-butyl)phosphate/TRITON X-100/soybean oil (TTO), TRITON X-100/soybean oil (TO), and TRITON X-100 (T) alone for 30 min. The concentration of TRITON X-100 was the same in all preparations used for treatment. Inhibition of influenza A infection was measured using cellular ELISA. Each data point represents the mean of three replicates +/−one standard error.

FIG. 24 shows that BCTP does not affect adenovirus infectivity. Adenoviral vector (AD.RSV ntlacZ) was treated with three dilutions of BCTP for 30 min. and subsequently used for transfection of 293 cells. Five days later the 6-galactosidase assay was performed. Each data point represents the mean of eight replicates +/−one standard error.

FIG. 25 illustrates the structures of influenza A and adenovirus viewed with electron microscopy. Viruses were either untreated or incubated with BCTP at 1:100 dilution for 15 and 60 min at room temperature and were subjected to electron microscopy fixation procedure as described in the Examples. FIG. 25A illustrates the influenza A virus untreated; FIG. 25B illustrates influenza A virus incubated with BCTP for 15 min; FIG. 25C illustrates the adenovirus untreated; and FIG. 25D illustrates the adenovirus incubated with BCTP for 60 min. For all images magnification=200,000×. The bar represents 200 nm.

FIG. 26 illustrates the antibacterial properties of 1% and 10% BCTP. The bactericidal effect (% killing) was calculated as:

$$\frac{cfu(\text{initial}) - cfu(\text{post-treatment})}{cfu(\text{initial})} \times 100$$

FIG. 27 illustrates the antiviral properties of 10% and 1% BCTP as assessed by plaque reduction assays.

FIG. 28 illustrates exemplary organisms that are target for the emulsions of the present invention.

FIG. 29 illustrates several particular embodiments of the various emulsion compositions invention and certain uses for the emulsions.

FIG. 30 illustrates several particular embodiments of the various emulsion compositions invention and certain uses for the emulsions.

FIG. 31 schematically depicts various generalized formulations and uses of certain embodiments of the present invention. FIG. 31A shows the log reduction of *E. coli* by various nanoemulsions of the present invention for 10%, 1% and 0.10% dilutions of the nanoemulsion. FIG. 31B shows log reduction of *B. globigii* spores by various nanoemulsions of the present invention for 10%, 1% and 0.10% dilutions of the nanoemulsion. FIG. 31C shows log reduction of influenza A (pfu/ml) by various nanoemulsions of the present invention for 10%, 1% and 0.10% dilutions of the nanoemulsion.

FIG. 32 shows a graph of the log reduction of *S. typhimurium* treated with an emulsion of the present invention in the presence of EDTA at 40° C.

FIG. 33 shows a graph of the log reduction of *S. typhimurium* treated with an emulsion of the present invention in the presence of EDTA at 50° C.

FIG. 34 shows the lytic effect of an emulsion of the present invention compared to the lytic effect of its non-emulsified ingredients.

FIG. 35 shows the log reduction of *Mycobacteria fortuitum* by an emulsion of the present invention at room temperature and 37° C.

FIG. 36 shows data for the decontamination of a surface using an emulsion of the present invention.

DEFINITIONS

To facilitate an understanding of the present invention, a number of terms and phrases are defined below:

As used herein the term "microorganism" refers to microscopic organisms and taxonomically related macroscopic organisms within the categories of algae, bacteria, fungi (including lichens), protozoa, viruses, and subviral agents. The term microorganism encompasses both those organisms that are in and of themselves pathogenic to another organism (e.g., animals, including humans, and plants) and those organisms that produce agents that are pathogenic to another organism, while the organism itself is not directly pathogenic or infective to the other organism. As used herein the term "pathogen," and grammatical equivalents, refers to an organism, including microorganisms, that causes disease in another organism (e.g., animals and plants) by directly infecting the other organism, or by producing agents that causes disease in another organism (e.g., bacteria that produce pathogenic toxins and the like).

As used herein the term "disease" refers to a deviation from the condition regarded as normal or average for members of a species, and which is detrimental to an affected individual under conditions that are not inimical to the majority of individuals of that species (e.g., diarrhea, nausea, fever, pain, and inflammation etc). A disease may be caused or result from contact by microorganisms and/or pathogens.

Figure 1:
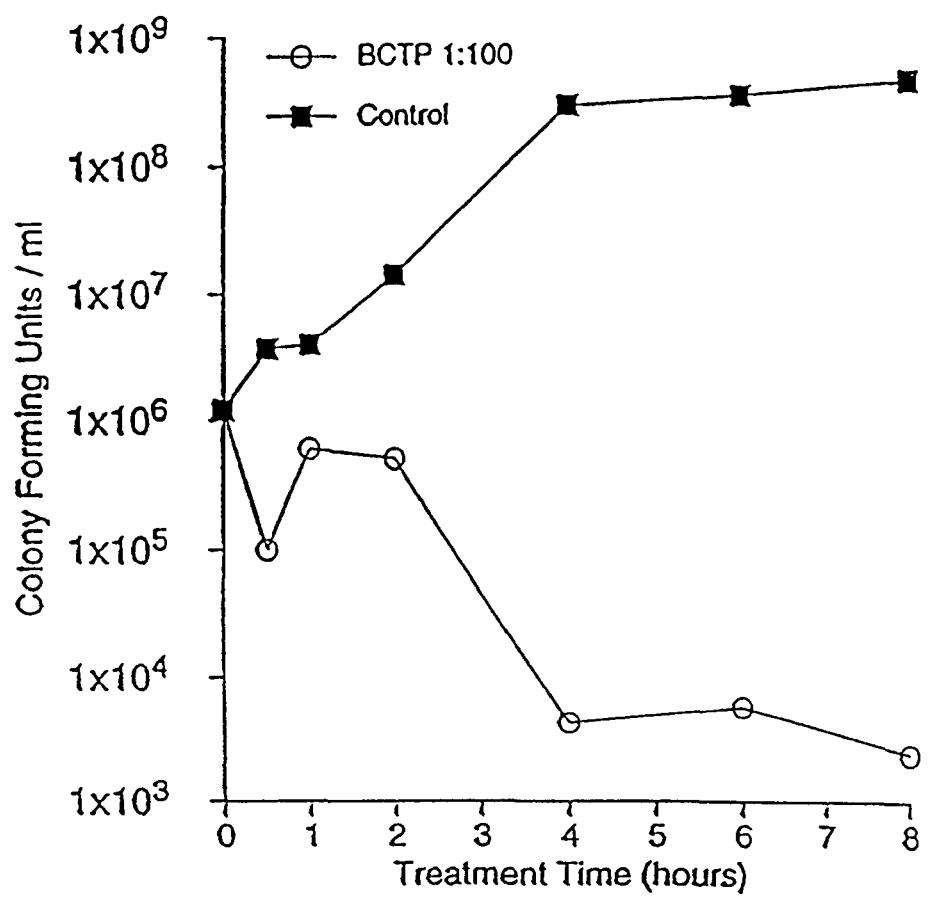
FIG. 1 illustrates the bactericidal efficacy of an emulsion of the present invention on *B. cereus* spores.

The terms "host" or "subject," as used herein, refer to organisms to be treated by the compositions of the present invention. Such organisms include organisms that are exposed to, or suspected of being exposed to, one or more pathogens. Such organisms also include organisms to be treated so as to prevent undesired exposure to pathogens. Organisms include, but are not limited to animals (e.g., humans, domesticated animal species, wild animals) and plants.

As used herein, the term "inactivating," and grammatical equivalents, means having the ability to kill, eliminate or reduce the capacity of a pathogen to infect and/or cause a pathological responses in a host.

As used herein, the term "fusigenic" is intended to refer to an emulsion that is capable of fusing with the membrane of a microbial agent (e.g., a bacterium or bacterial spore). Specific examples of fusigenic emulsions include, but are not limited to, $W_{80}8P$ described in U.S. Pat. Nos. 5,618,840; 5,547,677; and 5,549,901 and NP9 described in U.S. Pat. No. 5,700,679, each of which is herein incorporated by reference in their entireties. NP9 is a branched poly(oxy-1,2 ethaneolyl), alpha-(4-nonylphenal)-omega-hydroxy-surfactant. While not being limited to the following, NP9 and other surfactants that may be useful in the present invention are described in Table 1 of U.S. Pat. No. 5,662,957, herein incorporated by reference in its entirety.

As used herein, the term "lysogenic" refers to an emulsion that is capable of disrupting the membrane of a microbial agent (e.g., a bacterium or bacterial spore). An exemplary lysogenic composition is BCTP. In preferred embodiments of the present invention, the presence of both a lysogenic and a fusigenic agent in the same composition produces an enhanced inactivating effect than either agent alone. Methods and compositions using this improved antimicrobial composition are described in detail herein.

The term "emulsion," as used herein, includes classic oil-in-water dispersions or droplets, as well as other lipid structures that can form as a result of hydrophobic forces that drive apolar residues (i.e., long hydrocarbon chains) away from water and drive polar head groups toward water, when a water immiscible oily phase is mixed with an aqueous phase. These other lipid structures include, but are not limited to, unilamellar, paucilamellar, and multilamellar lipid vesicles, micelles, and lamellar phases. Similarly, the term "nanoemulsion," as used herein, refers to oil-in-water dispersions comprising small lipid structures. For example, in preferred embodiments, the nanoemulsion comprise an oil phase having droplets with a mean particle size of approximately 0.1 or less to 5 microns (e.g., 0.1 to 1.0). The terms "emulsion" and "nanoemulsion" are often used herein, interchangeably, to refer to the nanoemulsions of the present invention.

As used herein, the terms "contacted" and "exposed," refers to bringing one or more of the compositions of the present invention into contact with a pathogen or a sample to be protected against pathogens such that the compositions of the present invention may inactivate the microorganism or pathogenic agents, if present. The present invention contemplates that the disclosed compositions are contacted to the pathogens or microbial agents in sufficient volumes and/or concentrations to inactivate the pathogens or microbial agents.

The term "surfactant" refers to any molecule having both a polar head group, which energetically prefers salvation by water, and a hydrophobic tail which is not well solvated by water. The term "cationic surfactant" refers to a surfactant with a cationic head group. The term "anionic surfactant" refers to a surfactant with an anionic head group.

The terms "Hydrophile-Lipophile Balance Index Number" and "HLB Index Number" refer to an index for correlating the chemical structure of surfactant molecules with their surface activity. The HLB Index Number may be calculated by a variety of empirical formulas as described by Meyers, (Meyers, *Surfactant Science and Technology*, VCH Publishers Inc., New York, pp. 231-245 [1992]), incorporated herein by reference. As used herein, the HLB Index Number of a surfactant is the HLB Index Number assigned to that surfactant in McCutcheon's Volume 1: Emulsifiers and Detergents North American Edition, 1996 (incorporated herein by reference). The HLB Index Number ranges from 0 to about 70 or more for commercial surfactants. Hydrophilic surfactants with high solubility in water and solubilizing properties are at the high end of the scale, while surfactants with low solubility in water which are good solubilizers of water in oils are at the low end of the scale.

As used herein, the term "germination enhancers" describe compounds that act to enhance the germination of certain strains of bacteria (e.g., L-amino acids [L-alanine], $CaCl_2$, Inosine, etc).

As used herein the term "interaction enhancers" describes compounds that act to enhance the interaction of an emulsion with the cell wall of a bacteria (e.g., a Gram negative bacteria). Contemplated interaction enhancers include but are not limited to chelating agents (e.g., ethylenediaminetetraacetic acid [EDTA], ethylenebis(oxyethylenenitrilo)tetraacetic acid [EGTA], and the like) and certain biological agents (e.g., bovine serum albumin [BSA] and the like).

The terms "buffer" or "buffering agents" refer to materials which when added to a solution, cause the solution to resist changes in pH.

The terms "reducing agent" and "electron donor" refer to a material that donates electrons to a second material to reduce the oxidation state of one or more of the second material's atoms.

The term "monovalent salt" refers to any salt in which the metal (e.g., Na, K, or Li) has a net 1+ charge in solution (i.e., one more proton than electron).

The term "divalent salt" refers to any salt in which a metal (e.g., Mg, Ca, or Sr) has a net 2+ charge in solution.

The terms "chelator" or "chelating agent" refer to any materials having more than one atom with a lone pair of electrons that are available to bond to a metal ion.

The term "solution" refers to an aqueous or non-aqueous mixture.

As used herein, the term "therapeutic agent," refers to compositions that decrease the infectivity, morbidity, or onset of mortality in a host contacted by a pathogenic microorganism or that prevent infectivity, morbidity, or onset of mortality in a host contacted by a pathogenic microorganism. Such agents may additionally comprise pharmaceutically acceptable compounds (e.g., adjutants, excipients, stabilizers, diluents, and the like). In some embodiments, the therapeutic agents of the present invention are administered in the form of topical emulsions, injectable compositions, ingestable solutions, and the like. When the route is topical, the form may be, for example, a cream, ointment, salve or spray.

The terms "pharmaceutically acceptable" or "pharmacologically acceptable," as used herein, refer to compositions that do not substantially produce adverse allergic or immunological reactions when administered to a host (e.g., an animal or a human). Moreover, in certain embodiments, the compositions of the present invention may be formulated for horticultural or agricultural use. Such formulations include dips, sprays, seed dressings, stem injections, sprays, and mists. As used herein, "pharmaceutically acceptable carrier"

includes any and all solvents, dispersion media, coatings, wetting agents (e.g., sodium lauryl sulfate), isotonic and absorption delaying agents, disintrigrants (e.g., potato starch or sodium starch glycolate), and the like.

As used herein, the term "topically" refers to application of the compositions of the present invention to the surface of the skin and mucosal cells and tissues (e.g., alveolar, buccal, lingual, masticatory, or nasal mucosa, and other tissues and cells which line hollow organs or body cavities).

As used herein, the term "topically active agents" refers to compositions of the present invention that elicit pharmacological responses at the site of application (contact) to a host.

As used herein, the term "systemically active drugs" is used broadly to indicate a substance or composition which will produce a pharmacological response at a site remote from the point of application or entry into a subject.

As used herein, the term "medical devices" includes any material or device that is used on, in, or through a patient's body in the course of medical treatment (e.g., for a disease or injury). Medical devices include, but are not limited to, such items as medical implants, wound care devices, drug delivery devices, and body cavity and personal protection devices. The medical implants include, but are not limited to, urinary catheters, intravascular catheters, dialysis shunts, wound drain tubes, skin sutures, vascular grafts, implantable meshes, intraocular devices, heart valves, and the like. Wound care devices include, but are not limited to, general wound dressings, biologic graft materials, tape closures and dressings, and surgical incise drapes. Drug delivery devices include, but are not limited to, needles, drug delivery skin patches, drug delivery mucosal patches and medical sponges. Body cavity and personal protection devices, include, but are not limited to, tampons, sponges, surgical and examination gloves, and toothbrushes. Birth control devices include, but are not limited to, inter uterin devices (IUDs), diaphragms, and condoms.

As used herein, the term "purified" or "to purify" refers to the removal of contaminants or undesired compounds from a sample or composition. As used herein, the term "substantially purified" refers to the removal of from about 70 to 90%, up to 100%, of the contaminants or undesired compounds from a sample or composition.

As used herein, the term "surface" is used in its broadest sense. In one sense, the term refers to the outermost boundaries of an organism or inanimate object (e.g., vehicles, buildings, and food processing equipment, etc.) that are capable of being contacted by the compositions of the present invention (e.g., for animals: the skin, hair, and fur, etc., and for plants: the leaves, stems, flowering parts, and fruiting bodies, etc.). In another sense, the term also refers to the inner membranes and surfaces of animals and plants (e.g., for animals: the digestive tract, vascular tissues, and the like, and for plants: the vascular tissues, etc.) capable of being contacted by compositions by any of a number of transdermal delivery routes (e.g., injection, ingestion, transdermal delivery, inhalation, and the like).

As used herein, the term "sample" is used in its broadest sense. In one sense it can refer to animal cells or tissues. In another sense, it is meant to include a specimen or culture obtained from any source, such as biological and environmental samples. Biological samples may be obtained from plants or animals (including humans) and encompass fluids, solids, tissues, and gases. Environmental samples include environmental material such as surface matter, soil, water, and industrial samples. These examples are not to be construed as limiting the sample types applicable to the present invention.

DETAILED DESCRIPTION OF THE INVENTION

The present invention comprises compositions and methods for decreasing the infectivity, morbidity, and rate of mortality associated with a variety of microbial and pathogenic organisms. The present invention also relates to methods and compositions for decontaminating areas colonized or otherwise infected by pathogenic organisms. Moreover, the present invention relates to methods and compositions for decreasing the infectivity of pathogenic organisms in foodstuffs. In preferred embodiments, decreased pathogenic organism infectivity, morbidity, and mortality is accomplished by contacting the pathogenic organism with an oil-in-water composition comprising an aqueous phase, and oil phase, an at least one other compound. In some preferred embodiments, the compositions of the present invention are non-toxic, non-irritant, and non-corrosive, while possessing potency against a broad spectrum of microorganisms, including bacteria, fungi, viruses, and spores. Certain illustrative embodiments of the present invention are described below. The present invention is not limited to these specific embodiments. The description is provided in the following sections: I) Exemplary Compositions; II) Exemplary Formulation Techniques; III) Properties and Activities; IV) Uses; and V) Specific Examples.

I. Exemplary Compositions

In preferred embodiments, the emulsions of the present invention comprise (i) an aqueous phase; (ii) an oil phase; and at least one additional compound. In some embodiments of the present invention, these additional compounds are admixed into either the aqueous or oil phases of the composition. In other embodiments, these additional compounds are admixed into a composition of previously emulsified oil and aqueous phases. In certain of these embodiments, one or more additional compounds are admixed into an existing emulsion composition immediately prior to its use. In other embodiments, one or more additional compounds are admixed into an existing emulsion composition prior to the compositions immediate use.

Additional compounds suitable for use in the compositions of the present invention include but are not limited to one or more organic, and more particularly, organic phosphate based solvents, surfactants and detergents, cationic halogen containing compounds, germination enhancers, interaction enhancers, food additives (e.g., flavorings, sweetners, bulking agents, and the like) and pharmaceutically acceptable compounds. Certain exemplary embodiments of the various compounds contemplated for use in the compositions of the present invention are presented below.

A. Aqueous Phase

In certain preferred embodiments, the emulsion comprises about 5 to 60, preferably 10 to 40, more preferably 15 to 30, vol. % aqueous phase, based on the total volume of the emulsion, although higher and lower amounts are contemplated. In preferred embodiments, the aqueous phase comprises water at a pH of about 4 to 10, preferably about 6 to 8. When the emulsions of the present invention contain a germination enhancer, the pH is preferably 6 to 8. The water is preferably deionized (hereinafter "Di$H_2O$") or distilled. In some embodiments the aqueous phase comprises phosphate buffered saline (PBS). In those embodiments of the present invention intended for consumption by, or contact to, a host, the aqueous phase, and any additional compounds provided in the aqueous phase, may further be sterile and pyrogen free.

B. Oil Phase and Solvents In certain preferred embodiments, the oil phase (e.g., carrier oil) of the emulsion of the present invention comprises 30-90, preferably 60-80, and more preferably 60-70, vol. % of oil, based on the total volume of the emulsion, although higher and lower amounts are contemplated. Suitable oils include, but are not limited to, soybean oil, avocado oil, flaxseed oil, coconut oil, cottonseed oil, squalene oil, olive oil, canola oil, corn oil, rapeseed oil, safflower oil, sunflower oil, pine oil (e.g., 15%), Olestra oil, fish oils, flavor oils, water insoluble vitamins and mixtures thereof. In particularly preferred embodiments, soybean oil is used. Additional contemplated oils include motor oils, mineral oils, and butter. In preferred embodiments of the present invention, the oil phase is preferably distributed throughout the aqueous phase as droplets having a mean particle size in the range from about 1-2 microns, more preferably from 0.2 to 0.8, and most preferably about 0.8 microns. In other embodiments, the aqueous phase can be distributed in the oil phase. In some preferred embodiments, very small droplet sizes are utilized (e.g., less than 0.5 microns) to produce stable nanoemulsion compositions. It is contemplated that small droplet composition also provide clear solutions, which may find desired use in certain product types.

In some embodiments, the oil phase comprises 3-15, preferably 5-10 vol. % of an organic solvent, based on the total volume of the emulsion, although higher and lower amounts are contemplated. While the present invention is not limited to any particular mechanism, it is contemplated that the organic phosphate-based solvents employed in the emulsions serve to remove or disrupt the lipids in the membranes of the pathogens. Thus, any solvent that removes the sterols or phospholipids in the microbial membranes finds use in the emulsions of the present invention. Suitable organic solvents include, but are not limited to, organic phosphate based solvents or alcohols. In preferred embodiments, the organic phosphate based solvents include, but are not limited to, dialkyl- and trialkyl phosphates (e.g., tri-n-butyl phosphate [TBP]) in any combination. A particularly preferred trialkyl phosphate in certain embodiments comprises tri-n-butyl phosphate, which is a plasticizer. Moreover, in a preferred embodiment, each alkyl group of the di- or trialkyl phosphate has from one to ten or more carbon atoms, more preferably two to eight carbon atoms. The present invention also contemplates that each alkyl group of the di- or trialkyl phosphate may or may not be identical to one another. In certain embodiments, mixtures of different dialkyl and trialkyl phosphates can be employed. In those embodiments comprising one or more alcohols as solvents, such solvents include, but are not limited to, methanol, ethanol, propanol and octanol. In a particularly preferred embodiment, the alcohol is ethanol. In those embodiments of the present invention intended for consumption by, or contact to, a host, the oil phase, and any additional compounds provided in the oil phase, may further be sterile and pyrogen free.

C. Surfactants and Detergents

In some embodiments, the compositions of the present invention further comprise one or more surfactants or detergents (e.g., from about 3 to 15%, and preferably about 10%, although higher and lower amounts are contemplated). While the present invention is not limited to any particular mechanism, and an understanding of the mechanism is not required to practice the present invention, it is contemplated that surfactants, when present in the compositions, help to stabilize the compositions. Both non-ionic (non-anionic) and ionic surfactants are contemplated. Additionally, surfactants from the BRIJ family of surfactants find use in the compositions of the present invention. The surfactant can be provided in either the aqueous or the oil phase. Surfactants suitable for use with the emulsions include a variety of anionic and nonionic surfactants, as well as other emulsifying compounds that are capable of promoting the formation of oil-in-water emulsions. In general, emulsifying compounds are relatively hydrophilic, and blends of emulsifying compounds can be used to achieve the necessary qualities. In some formulations, nonionic surfactants have advantages over ionic emulsifiers in that they are substantially more compatible with a broad pH range and often form more stable emulsions than do ionic (e.g., soap-type) emulsifiers. Thus, in certain preferred embodiments, the compositions of the present invention comprises one or more non-ionic surfactants such as a polysorbate surfactants (e.g., polyoxyethylene ethers), polysorbate detergents, pheoxypolyethoxyethanols, and the like. Examples of polysorbate detergents useful in the present invention include, but are not limited to, TWEEN 20, TWEEN 40, TWEEN 60, TWEEN 80, etc.

TWEEN 60 (polyoxyethylenesorbitan monostearate), together with TWEEN 20, TWEEN 40 and TWEEN 80, comprise polysorbates that are used as emulsifiers in a number of pharmaceutical compositions. In some embodiments of the present invention, these compounds are also used as co-components with adjuvants. TWEEN surfactants also appear to have virucidal effects on lipid-enveloped viruses (See e.g., Eriksson et al., Blood Coagulation and Fibtinolysis 5 (Suppl. 3):S37-S44 [1994]).

Examples of pheoxypolyethoxyethanols, and polymers thereof, useful in the present invention include, but are not limited to, TRITON (e.g., X-100, X-301, X-165, X-102, X-200), and TYLOXAPOL. TRITON X-100 is a strong nonionic detergent and dispersing agent widely used to extract lipids and proteins from biological structures. It also has virucidal effect against broad spectrum of enveloped viruses (See e.g., Maha and Igarashi, Southeast Asian J. Trop. Med. Pub. Health 28:718 [1997]; and Portocala et al., Virologie 27:261 [1976]). Due to this anti-viral activity, it is employed to inactivate viral pathogens in fresh frozen human plasma (See e.g., Horowitz et al., Blood 79:826 [1992]).

In particularly preferred embodiments, the surfactants TRITON X-100 (t-octylphenoxypolyethoxyethanol), and/or TYLOXAPOL are employed. Some other embodiments, employ spermicides (e.g., Nonoxynol-9). Additional surfactants and detergents useful in the compositions of the present invention may be ascertained from reference works (e.g., McCutheon's Volume 1: Emulsions and Detergents—North American Edition, 2000).

In some embodiments, as shown in FIG. 28, compositions that comprise a surfactant and an organic solvent are useful for inactivating enveloped viruses and Gram positive bacteria.

D. Cationic Halogen Containing Compounds

In some embodiments, the compositions of the present invention further comprise a cationic halogen containing compound (e.g., from about 0.5 to 1.0 wt. % or more, based on the total weight of the emulsion, although higher and lower amounts are contemplated). In preferred embodiments, the cationic halogen-containing compound is preferably premixed with the oil phase; however, it should be understood that the cationic halogen-containing compound may be provided in combination with the emulsion composition in a distinct formulation. Suitable halogen containing compounds may be selected, for example, from compounds comprising chloride, fluoride, bromide and iodide ions. In preferred embodiments, suitable cationic halogen containing compounds include, but are not limited to, cetylpyridinium halides, cetyltrimethylammonium halides, cetyldimethylethylammonium halides, cetyldimethylbenzylammonium halides, cetyltributylphosphonium halides, dodecyltrimethylammonium halides, or tetradecyltrimethylammonium halides. In some particular embodiments, suitable cationic halogen containing compounds comprise, but are not limited to, cetylpyridinium chloride (CPC), cetyltrimethylammonium chloride, cetylbenzyldimethylammonium chloride, cetylpyridinium bromide (CPB), cetyltrimethylammonium bromide (CTAB), cetyldimethylethylammonium bromide, cetyltributylphosphonium bromide, dodecyltrimethylammonium bromide, and tetradecyltrimethylammonium bromide. In particularly preferred embodiments, the cationic halogen containing compound is CPC, although the compositions of the present invention are not limited to formulation with an particular cationic containing compound.

In some embodiments, addition of 1.0% wt. or more of a cationic containing compound to the emulsion compositions of the present invention provides a composition that is useful in inactivating enveloped viruses, Gram positive bacteria, Gram negative bacteria and fungi.

E. Germination Enhancers

In other embodiments of the present invention, the compositions further comprise one or more germination enhancing compounds (e.g., from about 1 mM to 15 mM, and more preferably from about 5 mM to 10 mM, although higher and lower amounts are contemplated). In preferred embodiments, the germination enhancing compound is provided in the aqueous phase prior to formation of the emulsion. The present invention contemplates that when germination enhancers are added to the disclosed compositions the sporicidal properties of the compositions are enhanced. The present invention further contemplates that such germination enhancers initiate sporicidal activity near neutral pH (between pH 6-8, and preferably 7). Such neutral pH emulsions can be obtained, for example, by diluting with phosphate buffer saline (PBS) or by preparations of neutral emulsions. The sporicidal activity of the compositions preferentially occurs when the spores initiate germination.

In specific embodiments, it has been demonstrated that the emulsions of the present invention have sporicidal activity. While the present invention is not limited to any particular mechanism, it is believed that the fusigenic component of the emulsions acts to initiate germination and before reversion to the vegetative form is complete the lysogenic component of the emulsion acts to lyse the newly germinating spore. These components of the emulsion thus act in concert to leave the spore susceptible to disruption by the emulsions. The addition of germination enhancer further facilitates the anti-sporicidal activity of the emulsions of the present invention, for example, by speeding up the rate at which the sporicidal activity occurs.

Germination of bacterial endospores and fungal spores is associated with increased metabolism and decreased resistance to heat and chemical reactants. For germination to occur, the spore must sense that the environment is adequate to support vegetation and reproduction. The amino acid L-alanine stimulates bacterial spore germination (See e.g., Hills, J. Gen. Micro. 4:38 [1950]; and Halvorson and Church, Bacteriol Rev. 21:112 [1957]). L-alanine and L-proline have also been reported to initiate fungal spore germination (Yanagita, Arch Mikrobiol 26:329 [1957]). Simple α-amino acids, such as glycine and L-alanine, occupy a central position in metabolism. Transamination or deamination of α-amino acids yields the glycogenic or ketogenic carbohydrates and the nitrogen needed for metabolism and growth. For example, transamination or deamination of L-alanine yields pyruvate which is the end product of glycolytic metabolism (Embden-Meyerhof-Parnas Pathway). Oxidation of pyruvate by pyruvate dehydrogenase complex yields acetyl-CoA, NADH, $H^+$, and $CO_2$. Acetyl-CoA is the initiator substrate for the tricarboxylic acid cycle (Kreb's Cycle) which in turns feeds the mitochondrial electron transport chain. Acetyl-CoA is also the ultimate carbon source for fatty acid synthesis as well as for sterol synthesis. Simple α-amino acids can provide the nitrogen, $CO_2$, glycogenic and/or ketogenic equivalents required for germination and the metabolic activity that follows.

In certain embodiments, suitable germination enhancing agents of the invention include, but are not limited to, α-amino acids comprising glycine and the L-enantiomers of alanine, valine, leucine, isoleucine, serine, threonine, lysine, phenylalanine, tyrosine, and the alkyl esters thereof. Additional information on the effects of amino acids on germination may be found in U.S. Pat. No. 5,510,104, herein incorporated by reference in its entirety. In some embodiments, a mixture of glucose, fructose, asparagine, sodium chloride (NaCl), ammonium chloride ($NH_4Cl$), calcium chloride ($CaCl_2$) and potassium chloride (KCl) also may be used. In particularly preferred embodiments of the present invention, the formulation comprises the germination enhancers L-alanine, $CaCl_2$, Inosine and $NH_4Cl$. In some embodiments, the compositions further comprise one or more common forms of growth media (e.g., trypticase soy broth, and the like) that additionally may or may not itself comprise germination enhancers and buffers.

The above compounds are merely exemplary germination enhancers and it is understood that other known germination enhancers will find use in the compositions of the present invention. A candidate germination enhancer should meet two criteria for inclusion in the compositions of the present invention: it should be capable of being associated with the emulsions of the present invention and it should increase the rate of germination of a target spore in the when incorporated in the emulsions of the present invention. One skilled in the art can determine whether a particular agent has the desired function of acting as an germination enhancer by applying such an agent in combination with the compositions of the present invention to a target and comparing the inactivation of the target when contacted by the admixture with inactivation of like targets by the composition of the present invention without the agent. Any agent that increases germination, and thereby decrease or inhibits the growth of the organisms, is considered a suitable enhancer for use in the present invention.

In still other embodiments, addition of a germination enhancer (or growth medium) to a neutral emulsion composition produces a composition that is useful in treating bacterial spores in addition to enveloped viruses, Gram negative bacteria, and Gram positive bacteria.

In some embodiments, the present invention provides antimicrobial compositions, including compositions that do not comprise emulsion or nanoemulsions, that comprise a germination enhancer. For example, germination enhancers may be added to any other material (e.g., commercial disinfectants, solutions, etc.) to promote germination and increase the ability of a composition to kill or neutralize spores as compared to the activity of the composition in the absence of the germination enhancer(s).

F. Interaction Enhancers

In still other embodiments, the compositions of the present invention comprise one or more compounds capable of increasing the interaction of the compositions (i.e., "interaction enhancer") with target pathogens (e.g., the cell wall of Gram negative bacteria such as *Vibrio, Salmonella, Shigella* and *Pseudomonas*). In preferred embodiments, the interaction enhancer is preferably premixed with the oil phase; however, in other embodiments the interaction enhancer is provided in combination with the compositions after emulsification. In certain preferred embodiments, the interaction enhancer is a chelating agent (e.g., ethylenediaminetetraacetic acid [EDTA] or ethylenebis(oxyethylenenitrilo) tetraacetic acid [EGTA] in a buffer [e.g., tris buffer]). It is understood that chelating agents are merely exemplary interaction enhancing compounds. Indeed, other agents that increase the interaction of the compositions of the present invention with microbial agents and/or pathogens are contemplated. In particularly preferred embodiments, the interaction enhancer is at a concentration of about 50 to about 250 µM, although higher and lower amounts are contemplated. One skilled in the art will be able to determine whether a particular agent has the desired function of acting as an interaction enhancer by applying such an agent in combination with the compositions of the present invention to a target and comparing the inactivation of the target when contacted by the admixture with inactivation of like targets by the composition of the present invention without the agent. Any agent that increases the interaction and thereby decrease or inhibits the growth of the bacteria in comparison to that parameter in its absence is considered an interaction enhancer.

In some embodiments, the addition of an interaction enhancer to the compositions of the present invention produces a composition that is useful in treating enveloped viruses, some Gram positive bacteria and some Gram negative bacteria.

G. Other Components

In some embodiments of the present invention, the nanoemulsion composition comprise one or more additional components to provide a desired property or functionality to the nanoemulsions. These components may be incorporated into the aqueous phase or the oil phase of the nanoemulsions and may be added prior to or following emulsification. For example, in some embodiments, the nanoemulsions further comprise phenols (e.g., triclosan, phenyl phenol), acidifying agents (e.g., citric acid [e.g., 1.5-6%], acetic acid, lemon juice), alkylating agents (e.g., sodium hydroxide [e.g., 0.3%]), buffers (e.g., citrate buffer, acetate buffer, and other buffers useful to maintain a specific pH), and halogens (e.g., polyvinylpyrrolidone, sodium hypochlorite, hydrogen peroxide).

II. Exemplary Formulations

In section A), set forth below, the present invention describes exemplary techniques for making generic formulations of the disclosed compositions. Additionally, the present invention recites a number of specific, although exemplary, formulation recipes in section B) set forth below.

A. Formulation Techniques

The pathogen inactivating oil-in-water emulsions of the present invention can be formed using classic emulsion forming techniques. In brief, the oil phase is mixed with the aqueous phase under relatively high shear forces (e.g., using high hydraulic and mechanical forces) to obtain an oil-in-water nanoemulsion. The emulsion is formed by blending the oil phase with an aqueous phase on a volume-to-volume basis ranging from about 1:9 to 5:1, preferably about 5:1 to 3:1, most preferably 4:1, oil phase to aqueous phase. The oil and aqueous phases can be blended using any apparatus capable of producing shear forces sufficient to form an emulsion such as French Presses or high shear mixers (e.g., FDA approved high shear mixers are available, for example, from Admix, Inc., Manchester, N.H.). Methods of producing such emulsions are described in U.S. Pat. Nos. 5,103,497 and 4,895,452, herein incorporated by reference in their entireties.

In preferred embodiments, the compositions used in the methods of the present invention comprise droplets of an oily discontinuous phase dispersed in an aqueous continuous phase, such as water. In preferred embodiments, the compositions of the present invention are stable, and do not decompose even after long storage periods (e.g., one or more years). Certain compositions of the present invention are non-toxic and safe when swallowed, inhaled, or contacted to the skin of a host. This is in contrast to many chemical microbicides, which are known irritants. Additionally, in some embodiments, the compositions are also non-toxic to plants.

The compositions of the present invention can be produced in large quantities and are stable for many months at a broad range of temperatures. Undiluted, they tend to have the texture of a semi-solid cream and can be applied topically by hand or mixed with water. Diluted, they tend to have a consistency and appearance similar to skim milk, and can be sprayed to decontaminate surfaces or potentially interact with aerosolized spores before inhalation. These properties provide a flexibility that is useful for a broad range of antimicrobial applications. Additionally, these properties make the compositions of the present invention particularly well suited to decontamination applications.

As stated above, at least a portion of the emulsion may be in the form of lipid structures including, but not limited to, unilamellar, multilamellar, and paucliamellar lipid vesicles, micelles, and lamellar phases.

Some embodiments of the present invention employ an oil phase containing ethanol. For example, in some embodiments, the emulsions of the present invention contain (i) an aqueous phase and (ii) an oil phase containing ethanol as the organic solvent and optionally a germination enhancer, and (iii) TYLOXAPOL as the surfactant (preferably 2-5%, more preferably 3%). This formulation is highly efficacious against microbes and is also non-irritating and non-toxic to mammalian users (and can thus be contacted with mucosal membranes).

In some other embodiments, the emulsions of the present invention comprise a first emulsion emulsified within a second emulsion, wherein (a) the first emulsion comprises (i) an aqueous phase; and (ii) an oil phase comprising an oil and an organic solvent; and (iii) a surfactant; and (b) the second emulsion comprises (i) an aqueous phase; and (ii) an oil phase comprising an oil and a cationic containing compound; and (iii) a surfactant.

B. Exemplary Formulations

Figure 30:
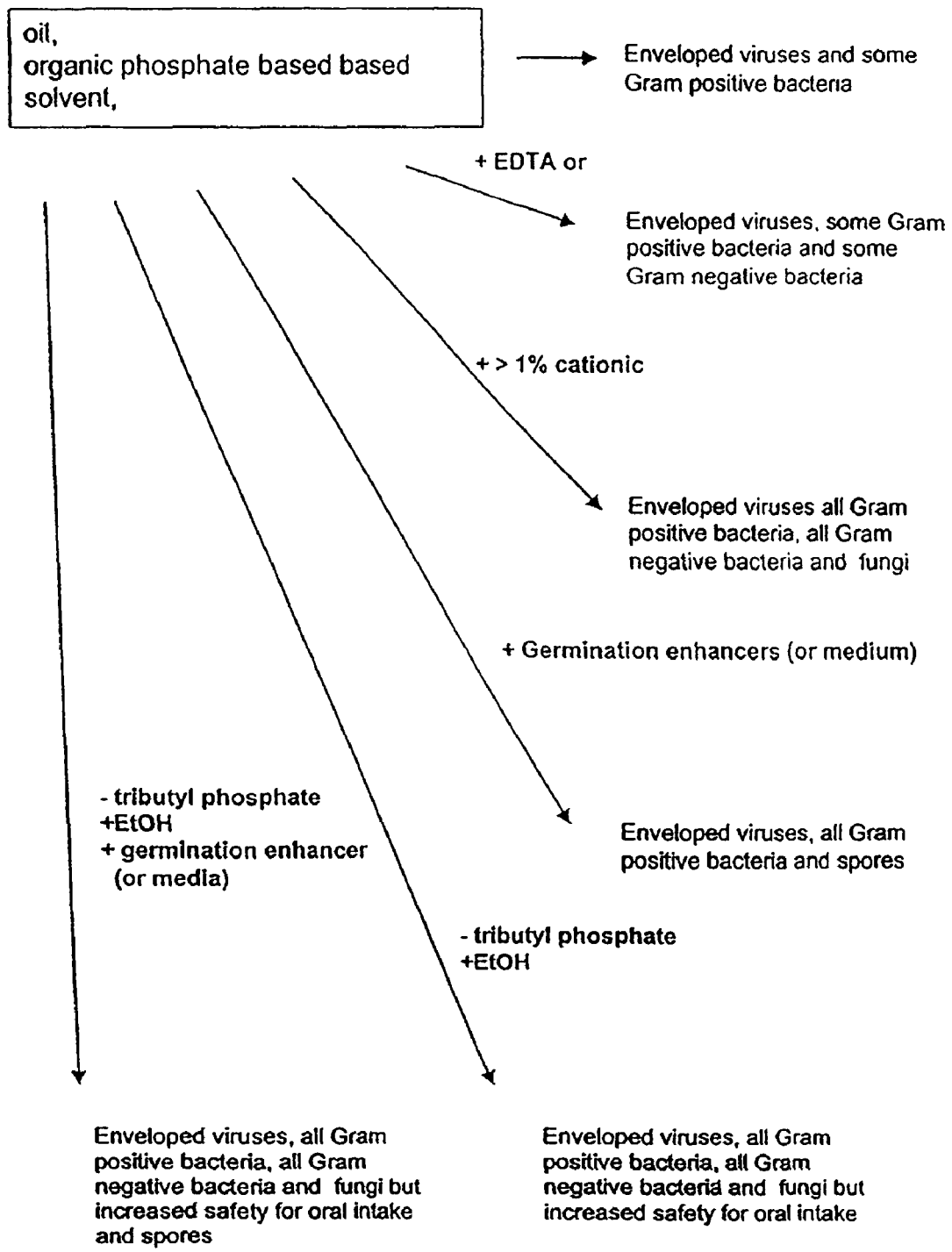

The following description provides a number of exemplary emulsions including formulations for compositions BCTP and $X_8W_{60}PC$. BCTP comprises a water-in oil nanoemulsion, in which the oil phase was made from soybean oil, tri-n-butyl phosphate, and TRITON X-100 in 80% water. $X_8W_{60}PC$ comprises a mixture of equal volumes of BCTP with $W_{80}8P$. $W_{80}8P$ is a liposome-like compound made of glycerol monostearate, refined oya sterols (e.g., GENEROL sterols), TWEEN 60, soybean oil, a cationic ion halogen-containing CPC and peppermint oil. The GENEROL family are a group of a polyethoxylated soya sterols (Henkel Corporation, Ambler, Pa.). Emulsion formulations are given in Table 1 for certain embodiments of the present invention. These particular formulations may be found in U.S. Pat. No. 5,700,679 (NN); U.S. Pat. Nos. 5,618,840; 5,549,901 ($W_{80}8P$); and U.S. Pat. No. 5,547,677, herein incorporated by reference in their entireties. Certain other emulsion formulations are presented in FIG. 29. Moreover, FIG. 30 schematically presents generalized formulations and uses of certain embodiments of the present invention.

The $X_8W_{60}PC$ emulsion is manufactured by first making the $W_{80}8P$ emulsion and BCTP emulsions separately. A mixture of these two emulsions is then re-emulsified to produce a fresh emulsion composition termed $X_8W_{60}PC$. Methods of producing such emulsions are described in U.S. Pat. Nos. 5,103,497 and 4,895,452 (herein incorporated by reference in their entireties). These compounds have broad-spectrum antimicrobial activity, and are able to inactivate vegetative bacteria through membrane disruption.

TABLE 1

| Name | Oil Phase Formula | Water to Oil Phase Ratio (Vol/Vol) |
|---|---|---|
| BCTP | 1 vol. Tri(N-butyl)phosphate<br>1 vol. TRITON X-100<br>8 vol. Soybean oil | 4:1 |
| NN | 86.5 g Glycerol monooleate<br>60.1 ml Nonoxynol-9<br>24.2 g GENEROL 122<br>3.27 g Cetylpyridinium chloride<br>554 g Soybean oil | 3:1 |
| $W_{80}8P$ | 86.5 g Glycerol monooleate<br>21.2 g Polysorbate 60<br>24.2 g GENEROL 122<br>3.27 g Cetylpyddinium chloride<br>4 ml Peppermint oil<br>554 g Soybean oil | 3.2:1 |
| SS | 86.5 g Glycerol monooleate<br>21.2 g Polysorbate 60<br>24.2 g GENEROL 122<br>3.27 g Cetylpyridinium chloride<br>554 g Soybean oil | 3.2:1<br>(1% bismuth in water) |

The compositions listed above are only exemplary and those of skill in the art will be able to alter the amounts of the components to arrive at a nanoemulsion composition suitable for the purposes of the present invention. Those skilled in the art will understand that the ratio of oil phase to water as well as the individual oil carrier, surfactant CPC and organic phosphate buffer, components of each composition may vary.

Although certain compositions comprising BCTP have a water to oil ratio of 4:1, it is understood that the BCTP may be formulated to have more or less of a water phase. For example, in some embodiments, there is 3, 4, 5, 6, 7, 8, 9, 10, or more parts of the water phase to each part of the oil phase. The same holds true for the $W_{80}8P$ formulation. Similarly, the ratio of Tri(N-butyl)phosphate:TRITON X-100:soybean oil also may be varied.

Although Table 1 lists specific amounts of glycerol monooleate, polysorbate 60, GENEROL 122, cetylpyridinium chloride, and carrier oil for $W_{80}8P$, these are merely exemplary. An emulsion that has the properties of $W_{80}8P$ may be formulated that has different concentrations of each of these components or indeed different components that will fulfill the same function. For example, the emulsion may have between about 80 to about 100 g of glycerol monooleate in the initial oil phase. In other embodiments, the emulsion may have between about 15 to about 30 g polysorbate 60 in the initial oil phase. In yet another embodiment the composition may comprise between about 20 to about 30 g of a GENEROL sterol, in the initial oil phase.

The nanoemulsions structure of the certain embodiments of the emulsions of the present invention may play a role in their biocidal activity as well as contributing to the non-toxicity of these emulsions. For example, the active component in BCTP, TRITON-X100 shows less biocidal activity against virus at concentrations equivalent to 11% BCTP. Adding the oil phase to the detergent and solvent markedly reduces the toxicity of these agents in tissue culture at the same concentrations. While not being bound to any theory (an understanding of the mechanism is not necessary to practice the present invention, and the present invention is not limited to any particular mechanism), it is suggested that the nanoemulsion enhances the interaction of its components with the pathogens thereby facilitating the inactivation of the pathogen and reducing the toxicity of the individual components. It should be noted that when all the components of BCTP are combined in one composition but are not in a nanoemulsion structure, the mixture is not as effective as an antimicrobial as when the components are in a nanoemulsion structure.

Numerous additional embodiments presented in classes of formulations with like compositions are presented below. The effect of a number of these compositions as antipathogenic materials is provided in FIG. 31. The following compositions recite various ratios and mixtures of active components. One skilled in the art will appreciate that the below recited formulation are exemplary and that additional formulations comprising similar percent ranges of the recited components are within the scope of the present invention.

In certain embodiments of the present invention, the inventive formulation comprise from about 3 to 8 vol. % of TYLOXAPOL, about 8 vol. % of ethanol, about 1 vol. % of cetylpyridinium chloride (CPC), about 60 to 70 vol. % oil (e.g., soybean oil), about 15 to 25 vol. % of aqueous phase (e.g., $DiH_2O$ or PBS), and in some formulations less than about 1 vol. % of 1N NaOH. Some of these embodiments comprise PBS. It is contemplated that the addition of 1N NaOH and/or PBS in some of these embodiments, allows the user to advantageously control the pH of the formulations, such that pH ranges from about 7.0 to about 9.0, and more preferably from about 7.1 to 8.5 are achieved. For example, one embodiment of the present invention comprises about 3 vol. % of TYLOXAPOL, about 8 vol. % of ethanol, about 1 vol. % of CPC, about 64 vol. % of soybean oil, and about 24 vol. % of $DiH_2O$ (designated herein as Y3EC). Another similar embodiment comprises about 3.5 vol. % of TYLOXAPOL, about 8 vol. % of ethanol, and about 1 vol. % of CPC, about 64 vol. % of soybean oil, and about 23.5 vol. % of $DiH_2O$ (designated herein as Y3.5EC). Yet another embodiment comprises about 3 vol. % of TYLOXAPOL, about 8 vol. % of ethanol, about 1 vol. % of CPC, about 0.067 vol. % of 1N NaOH, such that the pH of the formulation is about 7.1, about 64 vol. % of soybean oil, and about 23.93 vol. % of $DiH_2O$ (designated herein as Y3EC pH 7.1). Still another embodiment comprises about 3 vol. % of TYLOXAPOL, about 8 vol. % of ethanol, about 1 vol. % of CPC, about 0.67 vol. % of 1N NaOH, such that the pH of the formulation is about 8.5, and about 64 vol. % of soybean oil, and about 23.33 vol. % of $DiH_2O$ (designated herein as Y3EC pH 8.5). Another similar embodiment comprises about 4% TYLOXAPOL, about 8 vol. % ethanol, about 1% CPC, and about 64 vol. % of soybean oil, and about 23 vol. % of $DiH_2O$ (designated herein as Y4EC). In still another embodiment the formulation comprises about 8% TYLOXAPOL, about 8% ethanol, about 1 vol. % of CPC, and about 64 vol. % of soybean oil, and about 19 vol. % of $DiH_2O$ (designated herein as Y8EC). A further embodiment comprises about 8 vol. % of TYLOXAPOL, about 8 vol. % of ethanol, about 1 vol. % of CPC, about 64 vol. % of soybean oil, and about 19 vol. % of 1×PBS (designated herein as Y8EC PBS).

In some embodiments of the present invention, the inventive formulations comprise about 8 vol. % of ethanol, and about 1 vol. % of CPC, and about 64 vol. % of oil (e.g., soybean oil), and about 27 vol. % of aqueous phase (e.g., $DiH_2O$ or PBS) (designated herein as EC).

In the present invention, some embodiments comprise from about 8 vol. % of sodium dodecyl sulfate (SDS), about 8 vol. % of tributyl phosphate (TBP), and about 64 vol. % of oil (e.g., soybean oil), and about 20 vol. % of aqueous phase (e.g., $DiH_2O$ or PBS) (designated herein as S8P).

In certain embodiments of the present invention, the inventive formulation comprise from about 1 to 2 vol. % of TRITON X-100, from about 1 to 2 vol. % of TYLOXAPOL, from about 7 to 8 vol. % of ethanol, about 1 vol. % of cetylpyridinium chloride (CPC), about 64 to 57.6 vol. % of oil (e.g., soybean oil), and about 23 vol. % of aqueous phase (e.g., $DiH_2O$ or PBS). Additionally, some of these formulations further comprise about 5 mM of L-alanine/Inosine, and about 10 mM ammonium chloride. Some of these formulations comprise PBS. It is contemplated that the addition of PBS in some of these embodiments, allows the user to advantageously control the pH of the formulations. For example, one embodiment of the present invention comprises about 2 vol. % of TRITON X-100, about 2 vol. % of TYLOXAPOL, about 8 vol. % of ethanol, about 1 vol. % CPC, about 64 vol. % of soybean oil, and about 23 vol. % of aqueous phase $DiH_2O$. In another embodiment the formulation comprises about 1.8 vol. % of TRITON X-100, about 1.8 vol. % of TYLOXAPOL, about 7.2 vol. % of ethanol, about 0.9 vol. % of CPC, about 5 mM L-alanine/Inosine, and about 10 mM ammonium chloride, about 57.6 vol. % of soybean oil, and the remainder of 1×PBS (designated herein as 90% X2Y2EC/GE).

In alternative embodiments of the present invention, the formulations comprise from about 5 vol. % of TWEEN 80, from about 8 vol. % of ethanol, from about 1 vol. % of CPC, about 64 vol. % of oil (e.g., soybean oil), and about 22 vol. % of $DiH_2O$ (designated herein as $W_{80}5EC$).

In still other embodiments of the present invention, the formulations comprise from about 5 vol. % of TWEEN 20, from about 8 vol. % of ethanol, from about 1 vol. % of CPC, about 64 vol. % of oil (e.g., soybean oil), and about 22 vol. % of $DiH_2O$ (designated herein as $W_{20}5EC$).

In still other embodiments of the present invention, the formulations comprise from about 2 to 8 vol. % of TRITON X-100, about 8 vol. % of ethanol, about 1 vol. % of CPC, about 60 to 70 vol. % of oil (e.g., soybean, or olive oil), and about 15 to 25 vol. % of aqueous phase (e.g., $DiH_2O$ or PBS). For example, the present invention contemplates formulations comprising about 2 vol. % of TRITON X-100, about 8 vol. % of ethanol, about 64 vol. % of soybean oil, and about 26 vol. % of $DiH_2O$ (designated herein as X2E). In other similar embodiments, the formulations comprise about 3 vol. % of TRITON X-100, about 8 vol. % of ethanol, about 64 vol. % of soybean oil, and about 25 vol. % of $DiH_2O$ (designated herein as X3E). In still further embodiments, the formulations comprise about 4 vol. % Triton of X-100, about 8 vol. % of ethanol, about 64 vol. % of soybean oil, and about 24 vol. % of $DiH_2O$ (designated herein as X4E). In yet other embodiments, the formulations comprise about 5 vol. % of TRITON X-100, about 8 vol. % of ethanol, about 64 vol. % of soybean oil, and about 23 vol. % of $DiH_2O$ (designated herein as X5E). Another embodiment of the present invention comprises about 6 vol. % of TRITON X-100, about 8 vol. % of ethanol, about 64 vol. % of soybean oil, and about 22 vol. % of $DiH_2O$ (designated herein as X6E). In still further embodiments of the present invention, the formulations comprise about 8 vol. % of TRITON X-100, about 8 vol. % of ethanol, about 64 vol. % of soybean oil, and about 20 vol. % of $DiH_2O$ (designated herein as X8E). In still further embodiments of the present invention, the formulations comprise about 8 vol. % of TRITON X-100, about 8 vol. % of ethanol, about 64 vol. % of olive oil, and about 20 vol. % of $DiH_2O$ (designated herein as X8E O). In yet another embodiment comprises 8 vol. % of TRITON X-100, about 8 vol. % ethanol, about 1 vol. % CPC, about 64 vol. % of soybean oil, and about 19 vol. % of $DiH_2O$ (designated herein as X8EC).

In alternative embodiments of the present invention, the formulations comprise from about 1 to 2 vol. % of TRITON X-100, from about 1 to 2 vol. % of TYLOXAPOL, from about 6 to 8 vol. % TBP, from about 0.5 to 1.0 vol. % of CPC, from about 60 to 70 vol. % of oil (e.g., soybean), and about 1 to 35 vol. % of aqueous phase (e.g., $DiH_2O$ or PBS). Additionally, certain of these formulations may comprise from about 1 to 5 vol. % of trypticase soy broth, from about 0.5 to 1.5 vol. % of yeast extract, about 5 mM L-alanine/Inosine, about 10 mM ammonium chloride, and from about 20-40 vol. % of liquid baby formula. In some of the embodiments comprising liquid baby formula, the formula comprises a casein hydrolysate (e.g., Neutramigen, or Progestimil, and the like). In some of these embodiments, the inventive formulations further comprise from about 0.1 to 1.0 vol. % of sodium thiosulfate, and from about 0.1 to 1.0 vol. % of sodium citrate. Other similar embodiments comprising these basic components employ phosphate buffered saline (PBS) as the aqueous phase. For example, one embodiment comprises about 2 vol. % of TRITON X-100, about 2 vol. % TYLOXAPOL, about 8 vol. % TBP, about 1 vol. % of CPC, about 64 vol. % of soybean oil, and about 23 vol. % of $DiH_2O$ (designated herein as X2Y2EC). In still other embodiments, the inventive formulation comprises about 2 vol. % of TRITON X-100, about 2 vol. % TYLOXAPOL, about 8 vol. % TBP, about 1 vol. % of CPC, about 0.9 vol. % of sodium thiosulfate, about 0.1 vol. % of sodium citrate, about 64 vol. % of soybean oil, and about 22 vol. % of $DiH_2O$ (designated herein as X2Y2PC STS1). In another similar embodiment, the formulations comprise about 1.7 vol. % TRITON X-100, about 1.7 vol. % TYLOXAPOL, about 6.8 vol. % TBP, about 0.85% CPC, about 29.2% NEUTRAMIGEN, about 54.4 vol. % of soybean oil, and about 4.9 vol. % of $DiH_2O$ (designated herein as 85% X2Y2PC/baby). In yet another embodiment of the present invention, the formulations comprise about 1.8 vol. % of TRITON X-100, about 1.8 vol. % of TYLOXAPOL, about 7.2 vol. % of TBP, about 0.9 vol. % of CPC, about 5 mM L-alanine/Inosine, about 10 mM ammonium chloride, about 57.6 vol. % of soybean oil, and the remainder vol. % of 0.1×PBS (designated herein as 90% X2Y2 PC/GE). In still another embodiment, the formulations comprise about 1.8 vol. % of TRITON X-100, about 1.8 vol. % of TYLOXAPOL, about 7.2 vol. % TBP, about 0.9 vol. % of CPC, and about 3 vol. % trypticase soy broth, about 57.6 vol. % of soybean oil, and about 27.7 vol. % of $DiH_2O$ (designated herein as 90% X2Y2PC/TSB). In another embodiment of the present invention, the formulations comprise about 1.8 vol. % TRITON X-100, about 1.8 vol. % TYLOXAPOL, about 7.2 vol. % TBP, about 0.9 vol. % CPC, about 1 vol. % yeast extract, about 57.6 vol. % of soybean oil, and about 29.7 vol. % of $DiH_2O$ (designated herein as 90% X2Y2PC/YE).

In some embodiments of the present invention, the inventive formulations comprise about 3 vol. % of TYLOXAPOL, about 8 vol. % of TBP, and about 1 vol. % of CPC, about 60 to 70 vol. % of oil (e.g., soybean or olive oil), and about 15 to 30 vol. % of aqueous phase (e.g., $DiH_2O$ or PBS). In a particular embodiment of the present invention, the inventive formulations comprise about 3 vol. % of TYLOXAPOL, about 8 vol. % of TBP, and about 1 vol. % of CPC, about 64 vol. % of soybean, and about 24 vol. % of DiH$_2$O (designated herein as Y3PC).

In some embodiments of the present invention, the inventive formulations comprise from about 4 to 8 vol. % of TRITON X-100, from about 5 to 8 vol. % of TBP, about 30 to 70 vol. % of oil (e.g., soybean or olive oil), and about 0 to 30 vol. % of aqueous phase (e.g., DiH$_2$O or PBS). Additionally, certain of these embodiments further comprise about 1 vol. % of CPC, about 1 vol. % of benzalkonium chloride, about 1 vol. % cetylyridinium bromide, about 1 vol. % cetyldimethyletylammonium bromide, 500 µM EDTA, about 10 mM ammonium chloride, about 5 mM Inosine, and about 5 mM L-alanine. For example, in certain of these embodiments, the inventive formulations comprise about 8 vol. % of TRITON X-100, about 8 vol. % of TBP, about 64 vol. % of soybean oil, and about 20 vol. % of DiH$_2$O (designated herein as X8P). In another embodiment of the present invention, the inventive formulations comprise about 8 vol. % of TRITON X-100, about 8 vol. % of TBP, about 1% of CPC, about 64 vol. % of soybean oil, and about 19 vol. % of DiH$_2$O (designated herein as X8PC). In still another embodiment, the formulations comprise about 8 vol. % TRITON X-100, about 8 vol. % of TBP, about 1 vol. % of CPC, about 50 vol. % of soybean oil, and about 33 vol. % of DiH$_2$O (designated herein as ATB-X1001). In yet another embodiment, the formulations comprise about 8 vol. % of TRITON X-100, about 8 vol. % of TBP, about 2 vol. % of CPC, about 50 vol. % of soybean oil, and about 32 vol. % of DiH$_2$O (designated herein as ATB-X002). Another embodiment of the present invention comprises about 4 vol. % TRITON X-100, about 4 vol. % of TBP, about 0.5 vol. % of CPC, about 32 vol. % of soybean oil, and about 59.5 vol. % of DiH$_2$O (designated herein as 50% X8PC). Still another related embodiment comprises about 8 vol. % of TRITON X-100, about 8 vol. % of TBP, about 0.5 vol. % CPC, about 64 vol. % of soybean oil, and about 19.5 vol. % of DiH$_2$O (designated herein as X8PC$_{1/2}$). In some embodiments of the present invention, the inventive formulations comprise about 8 vol. % of TRITON X-100, about 8 vol. % of TBP, about 2 vol. % of CPC, about 64 vol. % of soybean oil, and about 18 vol. % of DiH$_2$O (designated herein as X8PC2). In other embodiments, the inventive formulations comprise about 8 vol. % of TRITON X-100, about 8% of TBP, about 1% of benzalkonium chloride, about 50 vol. % of soybean oil, and about 33 vol. % of DiH$_2$O (designated herein as X8P BC). In an alternative embodiment of the present invention, the formulation comprise about 8 vol. % of TRITON X-100, about 8 vol. % of TBP, about 1 vol. % of cetylyridinium bromide, about 50 vol. % of soybean oil, and about 33 vol. % of DiH$_2$O (designated herein as X8P CPB). In another exemplary embodiment of the present invention, the formulations comprise about 8 vol. % of TRITON X-100, about 8 vol. % of TBP, about 1 vol. % of cetyldimethyletylammonium bromide, about 50 vol. % of soybean oil, and about 33 vol. % of DiH$_2$O (designated herein as X8P CTAB). In still further embodiments, the present invention comprises about 8 vol. % of TRITON X-100, about 8 vol. % of TBP, about 1 vol. % of CPC, about 500 µM EDTA, about 64 vol. % of soybean oil, and about 15.8 vol. % DiH$_2$O (designated herein as X8PC EDTA). Additional similar embodiments comprise 8 vol. % of TRITON X-100, about 8 vol. % of TBP, about 1 vol. % of CPC, about 10 mM ammonium chloride, about 5 mM Inosine, about 5 mM L-alanine, about 64 vol. % of soybean oil, and about 19 vol. % of DiH$_2$O or PBS (designated herein as X8PC GE$_{1-x}$). In another embodiment of the present invention, the inventive formulations further comprise about 5 vol. % of TRITON X-100, about 5% of TBP, about 1 vol. % of CPC, about 40 vol. % of soybean oil, and about 49 vol. % of DiH$_2$O (designated herein as X5P$_5$C).

In some embodiments of the present invention, the inventive formulations comprise about 2 vol. % TRITON X-100, about 6 vol. % TYLOXAPOL, about 8 vol. % ethanol, about 64 vol. % of soybean oil, and about 20 vol. % of DiH$_2$O (designated herein as X2Y6E).

In an additional embodiment of the present invention, the formulations comprise about 8 vol. % of TRITON X-100, and about 8 vol. % of glycerol, about 60 to 70 vol. % of oil (e.g., soybean or olive oil), and about 15 to 25 vol. % of aqueous phase (e.g., DiH$_2$O or PBS). Certain related embodiments further comprise about 1 vol. % L-ascorbic acid. For example, one particular embodiment comprises about 8 vol. % of TRITON X-100, about 8 vol. % of glycerol, about 64 vol. % of soybean oil, and about 20 vol. % of DiH$_2$O (designated herein as X8G). In still another embodiment, the inventive formulations comprise about 8 vol. % of TRITON X-100, about 8 vol. % of glycerol, about 1 vol. % of L-ascorbic acid, about 64 vol. % of soybean oil, and about 19 vol. % of DiH$_2$O (designated herein as X8GV$_c$).

In still further embodiments, the inventive formulations comprise about 8 vol. % of TRITON X-100, from about 0.5 to 0.8 vol. % of TWEEN 60, from about 0.5 to 2.0 vol. % of CPC, about 8 vol. % of TBP, about 60 to 70 vol. % of oil (e.g., soybean or olive oil), and about 15 to 25 vol. % of aqueous phase (e.g., DiH$_2$O or PBS). For example, in one particular embodiment the formulations comprise about 8 vol. % of TRITON X-100, about 0.70 vol. % of TWEEN 60, about 1 vol. % of CPC, about 8 vol. % of TBP, about 64 vol. % of soybean oil, and about 18.3 vol. % of DiH$_2$O (designated herein as X8W60PC$_1$). Another related embodiment comprises about 8 vol. % of TRITON X-100, about 0.71 vol. % of TWEEN 60, about 1 vol. % of CPC, about 8 vol. % of TBP, about 64 vol. % of soybean oil, and about 18.29 vol. % of DiH$_2$O (designated herein as W60$_{0.7}$X8PC). In yet other embodiments, the inventive formulations comprise from about 8 vol. % of TRITON X-100, about 0.7 vol. % of TWEEN 60, about 0.5 vol. % of CPC, about 8 vol. % of TBP, about 64 to 70 vol. % of soybean oil, and about 18.8 vol. % of DiH$_2$O (designated herein as X8W60PC$_2$). In still other embodiments, the present invention comprises about 8 vol. % of TRITON X-100, about 0.71 vol. % of TWEEN 60, about 2 vol. % of CPC, about 8 vol. % of TBP, about 64 vol. % of soybean oil, and about 17.3 vol. % of DiH$_2$O. In another embodiment of the present invention, the formulations comprise about 0.71 vol. % of TWEEN 60, about 1 vol. % of CPC, about 8 vol. % of TBP, about 64 vol. % of soybean oil, and about 25.29 vol. % of DiH$_2$O (designated herein as W60$_{0.7}$PC).

In another embodiment of the present invention, the inventive formulations comprise about 2 vol. % of dioctyl sulfosuccinate, either about 8 vol. % of glycerol, or about 8 vol. % TBP, in addition to, about 60 to 70 vol. % of oil (e.g., soybean or olive oil), and about 20 to 30 vol. % of aqueous phase (e.g., DiH$_2$O or PBS). For example, one embodiment of the present invention comprises about 2 vol. % of dioctyl sulfosuccinate, about 8 vol. % of glycerol, about 64 vol. % of soybean oil, and about 26 vol. % of DiH$_2$O (designated herein as D2G). In another related embodiment, the inventive formulations comprise about 2 vol. % of dioctyl sulfosuccinate, and about 8 vol. % of TBP, about 64 vol. % of soybean oil, and about 26 vol. % of DiH$_2$O (designated herein as D2P).

In still other embodiments of the present invention, inventive formulations comprise about 8 to 10 vol. % of glycerol, and about 1 to 10 vol. % of CPC, about 50 to 70 vol. % of oil (e.g., soybean or olive oil), and about 15 to 30 vol. % of aqueous phase (e.g., DiH$_2$O or PBS). Additionally, in certain of these embodiments, the compositions further comprise about 1 vol. % of L-ascorbic acid. For example, one particular embodiment comprises about 8 vol. % of glycerol, about 1 vol. % of CPC, about 64 vol. % of soybean oil, and about 27 vol. % of DiH$_2$O (designated herein as GC). An additional related embodiment comprises about 10 vol. % of glycerol, about 10 vol. % of CPC, about 60 vol. % of soybean oil, and about 20 vol. % of DiH$_2$O (designated herein as GC10). In still another embodiment of the present invention, the inventive formulations comprise about 10 vol. % of glycerol, about 1 vol. % of CPC, about 1 vol. % of L-ascorbic acid, about 64 vol. % of soybean or oil, and about 24 vol. % of DiH$_2$O (designated herein as GCV$_c$).

In some embodiments of the present invention, the inventive formulations comprise about 8 to 10 vol. % of glycerol, about 8 to 10 vol. % of SDS, about 50 to 70 vol. % of oil (e.g., soybean or olive oil), and about 15 to 30 vol. % of aqueous phase (e.g., DiH$_2$O or PBS). Additionally, in certain of these embodiments, the compositions further comprise about 1 vol. % of lecithin, and about 1 vol. % of p-Hydroxybenzoic acid methyl ester. Exemplary embodiments of such formulations comprise about 8 vol. % SDS, 8 vol. % of glycerol, about 64 vol. % of soybean oil, and about 20 vol. % of DiH$_2$O (designated herein as S8G). A related formulation comprises about 8 vol. % of glycerol, about 8 vol. % of SDS, about 1 vol. % of lecithin, about 1 vol. % of p-Hydroxybenzoic acid methyl ester, about 64 vol. % of soybean oil, and about 18 vol. % of DiH$_2$O (designated herein as S8GL1B1).

In yet another embodiment of the present invention, the inventive formulations comprise about 4 vol. % of TWEEN 80, about 4 vol. % of TYLOXAPOL, about 1 vol. % of CPC, about 8 vol. % of ethanol, about 64 vol. % of soybean oil, and about 19 vol. % of DiH$_2$O (designated herein as W$_{80}$4Y4EC).

In some embodiments of the present invention, the inventive formulations comprise about 0.01 vol. % of CPC, about 0.08 vol. % of TYLOXAPOL, about 10 vol. % of ethanol, about 70 vol. % of soybean oil, and about 19.91 vol. % of DiH$_2$O (designated herein as Y.08EC.01).

In yet another embodiment of the present invention, the inventive formulations comprise about 8 vol. % of sodium lauryl sulfate, and about 8 vol. % of glycerol, about 64 vol. % of soybean oil, and about 20 vol. % of DiH$_2$O (designated herein as SLS8G).

C. Additional Formulations

The specific formulations described above are simply examples to illustrate the variety of compositions that find use in the present invention. The present invention contemplates that many variations of the above formulation, as well as additional nanoemulsions, find use in the methods of the present invention. To determine if a candidate emulsion is suitable for use with the present invention, three criteria may be analyzed. Using the methods and standards described herein, candidate emulsions can be easily tested to determine if they are suitable. First, the desired ingredients are prepare using the methods described herein, to determine if an emulsion can be formed. If an emulsion cannot be formed, the candidate is rejected. For example, a candidate composition made of 4.5% sodium thiosulfate, 0.5% sodium citrate, 10% n-butanol, 64% soybean oil, and 21% DiH$_2$O did not form an emulsion.

Second, the candidate emulsion should form a stable emulsion. An emulsion is stable if it remains in emulsion form for a sufficient period to allow its intended use. For example, for emulsions that are to be stored, shipped, etc., it may be desired that the composition remain in emulsion form for months to years. Typical emulsions that are relatively unstable, will lose their form within a day. For example, a candidate composition made of 8% 1-butanol, 5% Tween 10, 1% CPC, 64% soybean oil, and 22% DiH$_2$O did not form a stable emulsion. The following candidate emulsions were shown to be stable using the methods described herein: 0.08% Triton X-100, 0.08% Glycerol, 0.01% Cetylpyridinium Chloride, 99% Butter, and 0.83% diH$_2$O (designated herein as 1% X8GC Butter); 0.8% Triton X-100, 0.8% Glycerol, 0.1% Cetylpyridinium Chloride, 6.4% Soybean Oil, 1.9% diH$_2$O, and 90% Butter (designated herein as 10% X8GC Butter); 2% W$_{20}$5EC, 1% Natrosol 250L NF, and 97% diH$_2$O (designated herein as 2% W$_{20}$5EC L GEL); 1% Cetylpyridinium Chloride, 5% Tween 20, 8% Ethanol, 64% 70 Viscosity Mineral Oil, and 22% diH$_2$O (designated herein as W$_{20}$5EC 70 Mineral Oil); 1% Cetylpyridinium Chloride, 5% Tween 20, 8% Ethanol, 64% 350 Viscosity Mineral Oil, and 22% diH$_2$O (designated herein as W$_{20}$5EC 350 Mineral Oil). In some embodiments, nanoemulsions of the present invention are stable for over a week, over a month, or over a year.

Third, the candidate emulsion should have efficacy for its intended use. For example, an anti-bacterial emulsion should kill or disable bacteria to a detectable level or to a preferred kill level (e.g., 1 log, 2 log, 3 log, 4 log, . . . reduction). As shown herein, certain emulsions of the present invention have efficacy against specific microorganisms, but not against others. Using the methods described herein, one is capable of determining the suitability of a particular candidate emulsion against the desired microorganism. Generally, this involves exposing the microorganism to the emulsion for one or more time periods in a side-by-side experiment with the appropriate control samples (e.g., a negative control such as water) and determining if, and to what degree, the emulsion kills or disable the microorganism. For example, a candidate composition made of 1% ammonium chloride, 5% Tween 20, 8% ethanol, 64% soybean oil, and 22% DiH$_2$O was shown not to be an effective emulsion. The following candidate emulsions were shown to be effective using the methods described herein: 5% Tween 20, 5% Cetylpyridinium Chloride, 10% Glycerol, 60% Soybean Oil, and 20% diH$_2$O (designated herein as W$_{20}$5GC5); 1% Cetylpyridinium Chloride, 5% Tween 20, 10% Glycerol, 64% Soybean Oil, and 20% diH$_2$O (designated herein as W$_{20}$5GC); 1% Cetylpyridinium Chloride, 5% Tween 20, 8% Ethanol, 64% Olive Oil, and 22% diH$_2$O (designated herein as W$_{20}$5EC Olive Oil); 1% Cetylpyridinium Chloride, 5% Tween 20, 8% Ethanol, 64% Flaxseed Oil, and 22% diH$_2$O (designated herein as W$_{20}$5EC Flaxseed Oil); 1% Cetylpyridinium Chloride, 5% Tween 20, 8% Ethanol, 64% Corn Oil, and 22% diH$_2$O (designated herein as W$_{20}$5EC Corn Oil); 1% Cetylpyridinium Chloride, 5% Tween 20, 8% Ethanol, 64% Coconut Oil, and 22% diH$_2$O (designated herein as W$_{20}$5EC Coconut Oil); 1% Cetylpyridinium Chloride, 5% Tween 20, 8% Ethanol, 64% Cottonseed Oil, and 22% diH$_2$O (designated herein as W$_{20}$5EC Cottonseed Oil); 8% Dextrose, 5% Tween 10, 1% Cetylpyridinium Chloride, 64% Soybean Oil, and 22% diH$_2$O (designated herein as W$_{20}$5C Dextrose); 8% PEG 200, 5% Tween 10, 1% Cetylpyridinium Chloride, 64% Soybean Oil, and 22% diH$_2$O (designated herein as W$_{20}$5C PEG 200); 8% Methanol, 5% Tween 10, 1% Cetylpyridinium Chloride, 64% Soybean Oil, and 22% diH$_2$O (designated herein as W$_{20}$5C Methanol); 8% PEG 1000, 5% Tween 10, 1% Cetylpyridinium Chloride, 64% Soybean Oil, and 22% diH$_2$O (designated herein as W$_{20}$5C PEG 1000); 2% W$_{20}$5EC, 2% Natrosol 250H NF, and 96% diH$_2$O (designated herein as 2% W$_{20}$5EC Natrosol 2, also called 2% W$_{20}$5EC GEL); 2% W$_{20}$5EC, 1% Natrosol 250H NF, and 97% diH$_2$O (designated herein as 2% W$_{20}$5EC Natrosol 1); 2% W$_{20}$5EC, 3% Natrosol 250H NF, and 95% diH$_2$O (designated herein as 2% W$_{20}$5EC Natrosol 3); 2% W$_{20}$5EC, 0.5% Natrosol 250H NF, and 97.5% diH$_2$O (designated herein as 2% W$_{20}$5EC Natrosol 0.5); 2% W$_{20}$5EC, 2% Methocel A, and 96% diH$_2$O (designated herein as 2% W$_{20}$5EC Methocel A); 2% W$_{20}$5EC, 2% Methocel K, and 96% diH$_2$O (designated herein as 2% W$_{20}$5EC Methocel K); 2% Natrosol, 0.1% X8PC, 0.1×PBS, 5 mM L-alanine, 5 mM Inosine, 10 mM Ammonium Chloride, and diH$_2$O (designated herein as 0.1% X8PC/GE+2% Natrosol); 2% Natrosol, 0.8% Triton X-100, 0.8% Tributyl Phosphate, 6.4% Soybean Oil, 0.1% Cetylpyridinium Chloride, 0.1×PBS, 5 mM L-alanine, 5 mM Inosine, 10 mM Ammonium Chloride, and diH$_2$O (designated herein as 10% X8PC/GE+2% Natrosol); 1% Cetylpyridinium Chloride, 5% Tween 20, 8% Ethanol, 64% Lard, and 22% diH$_2$O (designated herein as W$_{20}$5EC Lard); 1% Cetylpyridinium Chloride, 5% Tween 20, 8% Ethanol, 64% Mineral Oil, and 22% diH$_2$O (designated herein as W$_{20}$5EC Mineral Oil); 0.1% Cetylpyridinium Chloride, 2% Nerolidol, 5% Tween 20, 10% Ethanol, 64% Soybean Oil, and 18.9% diH$_2$O (designated herein as W$_{20}$5EC$_{0.1}$N); 0.1% Cetylpyridinium Chloride, 2% Farnesol, 5% Tween 20, 10% Ethanol, 64% Soybean Oil, and 18.9% diH$_2$O (designated herein as W$_{20}$5EC$_{0.1}$F); 0.1% Cetylpyridinium Chloride, 5% Tween 20, 10% Ethanol, 64% Soybean Oil, and 20.9% diH$_2$O (designated herein as W$_{20}$5EC$_{0.1}$); 10% Cetylpyridinium Chloride, 8% Tributyl Phosphate, 8% Triton X-100, 54% Soybean Oil, and 20% diH$_2$O (designated herein as X8PC$_{10}$); 5% Cetylpyridinium Chloride, 8% Triton X-100, 8% Tributyl Phosphate, 59% Soybean Oil, and 20% diH$_2$O (designated herein as X8PC$_5$); 0.02% Cetylpyridinium Chloride, 0.1% Tween 20, 10% Ethanol, 70% Soybean Oil, and 19.88% diH$_2$O (designated herein as W$_{20}$0.1EC$_{0.02}$); 1% Cetylpyridinium Chloride, 5% Tween 20, 8% Glycerol, 64% Mobil 1, and 22% diH$_2$O (designated herein as W$_{20}$5GC Mobil 1); 7.2% Triton X-100, 7.2% Tributyl Phosphate, 0.9% Cetylpyridinium Chloride, 57.6% Soybean Oil, 0.1×PBS, 5 mM L-alanine, 5 mM Inosine, 10 mM Ammonium Chloride, and 25.87% diH$_2$O (designated herein as 90% X8PC/GE); 7.2% Triton X-100, 7.2% Tributyl Phosphate, 0.9% Cetylpyridinium Chloride, 57.6% Soybean Oil, 1% EDTA, 5 mM L-alanine, 5 mM Inosine, 10 mM Ammonium Chloride, 0.1×PBS, and diH$_2$O (designated herein as 90% X8PC/GE EDTA); and 7.2% Triton X-100, 7.2% Tributyl Phosphate, 0.9% Cetylpyridinium Chloride, 57.6% Soybean Oil, 1% Sodium Thiosulfate, 5 mM L-alanine, 5 mM Inosine, 10 mM Ammonium Chloride, 0.1×PBS, and diH$_2$O (designated herein as 90% X8PC/GE STS).

D. Non-Toxic, Non-Irritant, Non-Corrosive Formulations

In preferred embodiments of the present invention, the nanoemulsions are non-toxic (e.g., to humans, plants, or animals), non-irritant (e.g., to humans, plants, or animals), and non-corrosive (e.g., to humans, plants, or animals or the environment), while possessing potency against a broad range of microorganisms including bacteria, fungi, viruses, and spores. While a number of the above described nanoemulsions meet these qualifications, the following description provides a number of preferred non-toxic, non-irritant, non-corrosive, anti-microbial nanoemulsions of the present invention (hereinafter in this section referred to as "non-toxic nanoemulsions").

In some embodiments the non-toxic nanoemulsions comprise surfactant lipid preparations (SLPs) for use as broad-spectrum antimicrobial agents that are effective against bacteria and their spores, enveloped viruses, and fungi. In preferred embodiments, these SLPs comprises a mixture of oils, detergents, solvents, and cationic halogen-containing compounds in addition to several ions that enhance their biocidal activities. These SLPs are characterized as stable, non-irritant, and non-toxic compounds compared to commercially available bactericidal and sporicidal agents, which are highly irritant and/or toxic.

Ingredients for use in the non-toxic nanoemulsions include, but are not limited to: detergents (e.g., TRITON X-100 [5-15%] or other members of the TRITON family, TWEEN 60 [0.5-2%] or other members of the TWEEN family, or TYLOXAPOL [1-10%]); solvents (e.g., tributyl phosphate [5-15%]); alcohols (e.g., ethanol [5-15%] or glycerol [5-15%]); oils (e.g., soybean oil [40-70%]); cationic halogen-containing compounds (e.g., cetylpyridinium chloride [0.5-2%], cetylpyridinium bromide [0.5-2%], or cetyldimethylethyl ammonium bromide [0.5-2%]); quaternary ammonium compounds (e.g., benzalkonium chloride [0.5-2%], N-alkyldimethylbenzyl ammonium chloride [0.5-2%]); ions (calcium chloride [1 mM-40 mM], ammonium chloride [1 mM-20 mM], sodium chloride [5 mM-200 mM], sodium phosphate [1 mM-20 mM]); nucleosides (e.g., inosine [50 µM-20 mM]); and amino acids (e.g., L-alanine [50 µM-20 mM]). Emulsions are prepared, for example, by mixing in a high shear mixer for 3-10 minutes. The emulsions may or may not be heated before mixing at 82° C. for 1 hour.

Quaternary ammonium compounds for use in the present include, but are not limited to, N-alkyldimethyl benzyl ammonium saccharinate; 1,3,5-Triazine-1,3,5 (2H,4H,6H)-triethanol; 1-Decanaminium, N-decyl-N,N-dimethyl-, chloride (or) Didecyl dimethyl ammonium chloride; 2-(2-(p-(Diisobuyl)cresosxy)ethoxy)ethyl dimethyl benzyl ammonium chloride; 2-(2-(p-(Diisobutyl)phenoxy)ethoxy)ethyl dimethyl benzyl ammonium chloride; alkyl 1 or 3 benzyl-1-(2-hydroxethyl)-2-imidazolinium chloride; alkyl bis(2-hydroxyethyl)benzyl ammonium chloride; alkyl demethyl benzyl ammonium chloride; alkyl dimethyl 3,4-dichlorobenzyl ammonium chloride (100% C12); alkyl dimethyl 3,4-dichlorobenzyl ammonium chloride (50% C14, 40% C12, 10% C16); alkyl dimethyl 3,4-dichlorobenzyl ammonium chloride (55% C14, 23% C12, 20% C16); alkyl dimethyl benzyl ammonium chloride; alkyl dimethyl benzyl ammonium chloride (100% C14); alkyl dimethyl benzyl ammonium chloride (100% C16); alkyl dimethyl benzyl ammonium chloride (41% C14, 28% C12); alkyl dimethyl benzyl ammonium chloride (47% C12, 18% C14); alkyl dimethyl benzyl ammonium chloride (55% C16, 20% C14); alkyl dimethyl benzyl ammonium chloride (58% C14, 28% C16); alkyl dimethyl benzyl ammonium chloride (60% C14, 25% C12); alkyl dimethyl benzyl ammonium chloride (61% C11, 23% C14); alkyl dimethyl benzyl ammonium chloride (61% C12, 23% C14); alkyl dimethyl benzyl ammonium chloride (65% C12, 25% C14); alkyl dimethyl benzyl ammonium chloride (67% C12, 24% C14); alkyl dimethyl benzyl ammonium chloride (67% C12, 25% C14); alkyl dimethyl benzyl ammonium chloride (90% C14, 5% C12); alkyl dimethyl benzyl ammonium chloride (93% C14, 4% C12); alkyl dimethyl benzyl ammonium chloride (95% C16, 5% C18); alkyl dimethyl benzyl ammonium chloride (and) didecyl dimethyl ammonium chloride; alkyl dimethyl benzyl ammonium chloride (as in fatty acids); alkyl dimethyl benzyl ammonium chloride (C12-C16); alkyl dimethyl benzyl ammonium chloride (C12-C18); alkyl dimethyl benzyl and dialkyl dimethyl ammonium chloride; alkyl dimethyl dimethybenzyl ammonium chloride; alkyl dimethyl ethyl ammonium bromide (90% C14, 5% C16, 5% C12); alkyl dimethyl ethyl ammonium bromide (mixed alkyl and alkenyl groups as in the fatty acids of soybean oil); alkyl dimethyl ethylbenzyl ammonium chloride; alkyl dimethyl ethylbenzyl ammonium chloride (60% C14); alkyl dimethyl isoproylbenzyl ammonium chloride (50% C12, 30% C14, 17% C16, 3% C18); alkyl trimethyl ammonium chloride (58% C18, 40% C16, 1% C14, 1% C12); alkyl trimethyl ammonium chloride (90% C18, 10% C16); alkyldimethyl(ethylbenzyl) ammonium chloride (C12-18); Di-(C8-10)-alkyl dimethyl ammonium chlorides; dialkyl dimethyl ammonium chloride; dialkyl dimethyl ammonium chloride; dialkyl dimethyl ammonium chloride; dialkyl methyl benzyl ammonium chloride; didecyl dimethyl ammonium chloride; diisodecyl dimethyl ammonium chloride; dioctyl dimethyl ammonium chloride; dodecyl bis(2-hydroxyethyl) octyl hydrogen ammonium chloride; dodecyl dimethyl benzyl ammonium chloride; dodecylcarbamoyl methyl dimethyl benzyl ammonium chloride; heptadecyl hydroxyethylimidazolinium chloride; hexahydro-1,3,5-thris(2-hydroxyethyl)-s-triazine; myristalkonium chloride (and) Quat RNIUM 14; N,N-Dimethyl-2-hydroxypropylammonium chloride polymer; n-alkyl dimethyl benzyl ammonium chloride; n-alkyl dimethyl ethylbenzyl ammonium chloride; n-tetradecyl dimethyl benzyl ammonium chloride monohydrate; octyl decyl dimethyl ammonium chloride; octyl dodecyl dimethyl ammonium chloride; octyphenoxyethoxyethyl dimethyl benzyl ammonium chloride; oxydiethylenebis (alkyl dimethyl ammonium chloride); quaternary ammonium compounds, dicoco alkyldimethyl, chloride; trimethoxysily propyl dimethyl octadecyl ammonium chloride; trimethoxysilyl quats, trimethyl dodecylbenzyl ammonium chloride; n-dodecyl dimethyl ethylbenzyl ammonium chloride; n-hexadecyl dimethyl benzyl ammonium chloride; n-tetradecyl dimethyl benzyl ammonium chloride; n-tetradecyl dimethyl ethylbenzyl ammonium chloride; and n-octadecyl dimethyl benzyl ammonium chloride.

In general, the preferred non-toxic nanoemulsions are characterized by the following: they are approximately 200-800 nm in diameter, although both larger and smaller diameter nanoemulsions are contemplated; the charge depends on the ingredients; they are stable for relatively long periods of time (e.g., up to two years), with preservation of their biocidal activity; they are non-irritant and non-toxic compared to their individual components due, at least in part, to their oil contents that markedly reduce the toxicity of the detergents and the solvents; they are effective at concentrations as low as 0.1%; they have antimicrobial activity against most vegetative bacteria (including Gram-positive and Gram-negative organisms), fungi, and enveloped and nonenveloped viruses in 15 minutes (e.g., 99.99% killing); and they have sporicidal activity in 1-4 hours (e.g., 99.99% killing) when produced with germination enhancers.

III. Properties and Activities

The specific compositions of the present invention possess a range of beneficial activities and properties. A number of the exemplary beneficial properties and activities are set forth below: A) Microbicidal and Microbistatic Activity; B) Sporicidial and Sporistatic Activity: C) Viricidal and Viralstatic Activity; D) Fungicidal and Fungistatic Activity; and E) In vivo Effects. Additionally, FIG. 31A-C provides properties of certain exemplary formulations of the present invention. In some preferred embodiments, the nanoemulsions of the present invention have broad spectrum killing activities, whereby they kill or disable, two or more of: 1) bacteria (gram positive and gram negative), 2) viruses, 3) fungi, and 4) spores (e.g., 1 log, 2 log, 3 log, 4 log, . . . reduction).

A. Microbicidal and Microbistatic Activity

The methods of the present invention can be used to rapidly inactivate bacteria. In certain embodiments, the compositions are particularly effective at inactivating Gram positive bacteria. In preferred embodiments, the inactivation of bacteria occurs after about five to ten minutes. Thus, bacteria may be contacted with an emulsion according to the present invention and will be inactivated in a rapid and efficient manner. It is expected that the period of time between the contacting and inactivation may be as little as 5-10 minutes or less where the bacteria is directly exposed to the emulsion. However, it is understood that when the emulsions of the present invention are employed in a therapeutic context and applied systemically, the inactivation may occur over a longer period of time including, but not limited to, 5, 10, 15, 20, 25, 30, 60 minutes post application. Further, in additional embodiments it may be that the inactivation may take two, three, four, five or six hours to occur.

In other embodiments, the compositions and methods of the invention can also rapidly inactivate certain Gram negative bacteria. In some embodiments, the bacteria inactivating emulsions are premixed with a compound that increases the interaction of the emulsion by the cell wall. The use of these enhancers in the compositions of the present invention is discussed herein below. It should be noted that certain emulsions especially those comprising enhancers are effective against certain Gram positive and negative bacteria and may be administered orally where they will come in contact with necessary gut bacteria.

Figure 26:
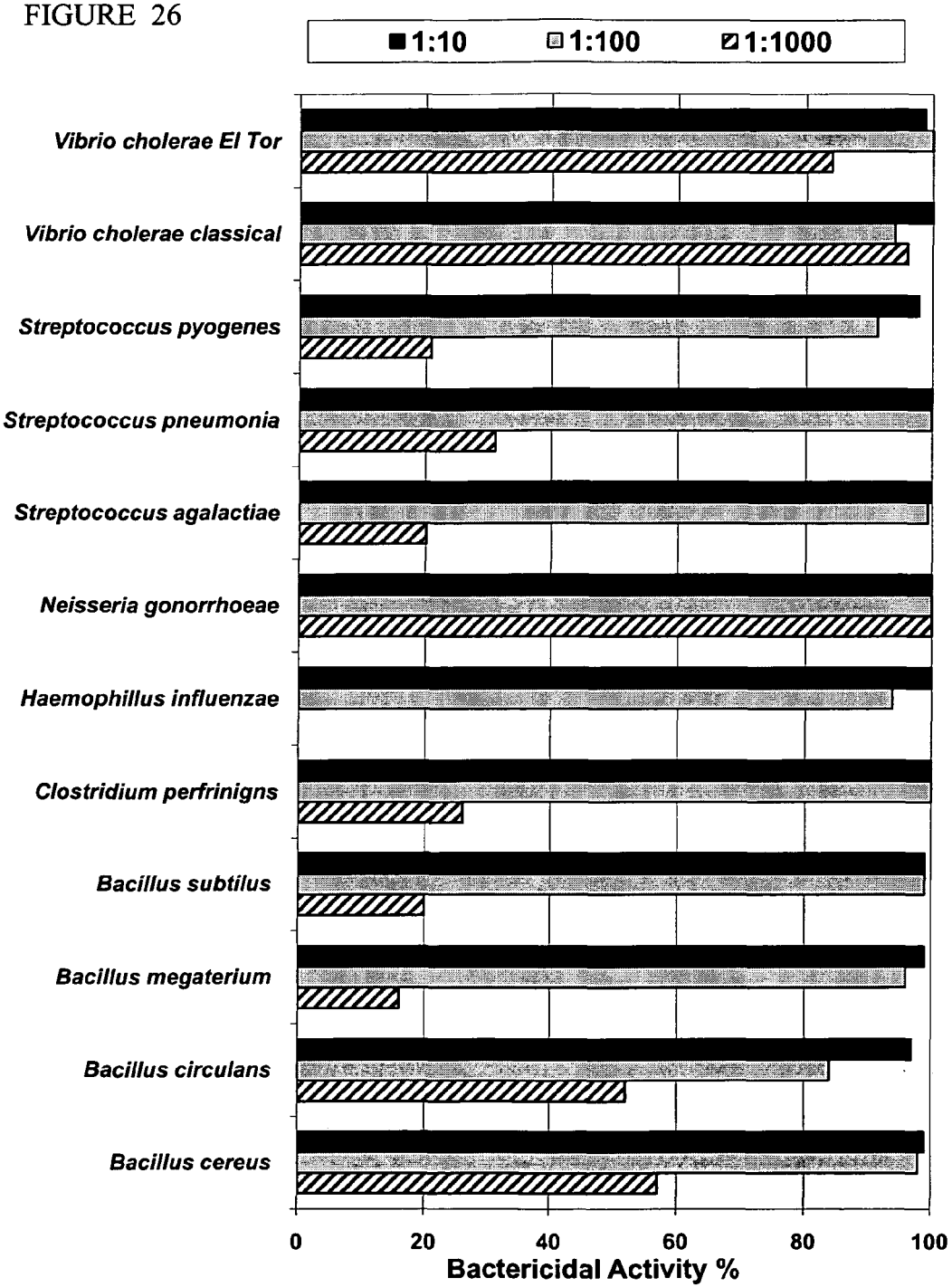

In specific embodiments, the present invention has shown that the emulsions of the present invention have potent, selective biocidal activity with minimal toxicity against vegetative bacteria. BCTP was highly effective against *B. cereus, B. circulans* and *B. megaterium, C. perfringens, H. influenzae, N. gonorrhoeae, S. agalactiae, S. pneumonia, S. pyogenes* and *V. cholerae* classical and Eltor (FIG. 26). This inactivation starts immediately on contact and is complete within 15 to 30 minutes for most of the susceptible microorganisms.

FIG. 31A shows the effectiveness of a number of exemplary nanoemulsions of the present invention against *E. coli*.

B. Sporicidial and Sporistatic Activity

In certain specific embodiments, the present invention has demonstrated that the emulsions of the present invention have sporicidal activity. Without being bound to any theory (an understanding of the mechanism is not necessary to practice the present invention, and the present invention is not limited to any particular mechanism), it is proposed the that the sporicidal ability of these emulsions occurs through initiation of germination without complete reversion to the vegetative form leaving the spore susceptible to disruption by the emulsions. The initiation of germination could be mediated by the action of the emulsion or its components.

The results of electron microscopy studies show disruption of the spore coat and cortex with disintegration of the core contents following BCTP treatment. Sporicidal activity appears to be mediated by both the TRITON X-100 and tri-n-butyl phosphate components since nanoemulsions lacking either component are inactive in vivo. This unique action of the emulsions, which is similar in efficiency to 1% bleach, is interesting because *Bacillus* spores are generally resistant to most disinfectants including many commonly used detergents (Russell, Clin. Micro. 3; 99 [1990]).

The present invention demonstrates that mixing BCTP with *B. cereus* spores before injecting into mice prevented the pathological effect of *B. cereus*. Further, the present invention shows that BCTP treatment of simulated wounds contaminated with *B. oereus* spores markedly reduced the risk of infection and mortality in mice. The control animals, that were injected with BCTP alone diluted 1:10, did not show any inflammatory effects proving that BCTP does not have cutaneous toxicity in mice. These results suggest that immediate treatment of spores prior to or following exposure can effectively reduce the severity of tissue damage of the experimental cutaneous infection.

Other experiments conducted during the development of the present invention compared the effects of BCTP and other emulsions derived from BCTP to inactivate different *Bacillus* spores. BCTP diluted up to 1:1000 (v/v) inactivated more than 90% of *B. anthracis* spores in four hours, and was also sporicidal against three other *Bacillus* species through the apparent disruption of spore coat. $X_8W_{60}PC$ diluted 1:1000 had more sporicidal activity against *B. anthracis, B. cereus,* and *B. subtilis* and had an onset of action in less than 30 minutes. In mice, mixing BCTP with *B. cereus* before subcutaneous injection or wound irrigation with BCTP 1 hour following spore inoculation resulted in over 98% reduction in skin lesion size. Mortality was reduced 4-fold in the latter experiment. The present compositions are stable, easily dispersed, non-irritant and nontoxic compared to the other available sporicidal agents.

The bacteria-inactivating oil-in-water emulsions used in the methods of the present invention can be used to inactivate a variety of bacteria and bacterial spores upon contact. For example, the presently disclosed emulsions can be used to inactivate *Bacillus* including *B. cereus, B. circulans* and *B. megatetium*, also including *Clostridium* (e.g., *C. botulinum* and *C. tetani*). The methods of the present invention may be particularly useful in inactivating certain biological warfare agents (e.g., *B. anthracis*). In addition, the formulations of the present invention also find use in combating *C. perftingens, H. influenzae, N. gonorrhoeae, S. agalactiae, S. pneumonia, S. pyogenes* and *V. cholerae* classical and Eltor (FIG. 26).

BCTP contains TRITON X-100 while SS and $W_{80}8P$ contain TWEEN 60, and NN contained nonoxynol-9 surfactant. Each is a non-ionic surfactant, but differs in its chemistry and biological characteristics. Nonoxynol-9 has strong spermicidal activity and it is widely used as a component of vaginally delivered contraceptive products (Lee, 1996). It has been claimed to have virucidal effect against enveloped viruses (Hermonat et al., 1992; Zeitlin et al., 1997). However, nanoxynol-9 has not been shown to be effective against non-enveloped viruses (Hermonat et al., 1992).

FIG. 31B shows the effectiveness of a number of exemplary nanoemulsions of the present invention against *B. globigii* spores.

C. Viricidal and Viralstatic Activity

In additional embodiments, it was demonstrated that the nanoemulsion compositions of the present invention have anti-viral properties. The effect of these emulsions on viral agents was monitored using plaque reduction assay (PRA), cellular enzyme-linked immunosorbent assay (ELISA), P-galactosidase assay, and electron microscopy (EM) and the cellular toxicity of lipid preparations was assessed using a (4,5-dimethylthiazole-2-yl)-2,5 diphenyltetrazolium (MTT) staining assay (Mosmann 1983).

There was a marked reduction of influenza A infectivity of MDCK cells as measured by cellular ELISA with subsequent confirmation by PRA. BCTP and SS at dilution 1:10 reduced virus infectivity over 95%. Two other emulsions showed only intermediate effects on the virus reducing infectivity by approximately 40% at dilution 1:10. BCTP was the most potent preparation and showed undiminished virucidal effect even at dilution 1:100. Kinetic studies showed that 5 min incubation of virus with BCTP at 1:10 dilution completely abolished its infectivity. TRITON X-100, an active compound of BCTP, at dilution 1:5000 only partially inhibited the infectivity of virus as compared to BCTP, indicating that the nanoemulsion itself contributes to the anti-viral efficacy. To further examine the anti-viral properties of BCTP, its action on non-enveloped viruses was investigated. The BCTP treatment did not affect the replication of lacZ adenovirus construct in 293 cells as measured using β-galactosidase assay. When examined with EM, influenza A virus was completely disrupted after incubation with BCTP while adenovirus remained intact.

Figure 27:
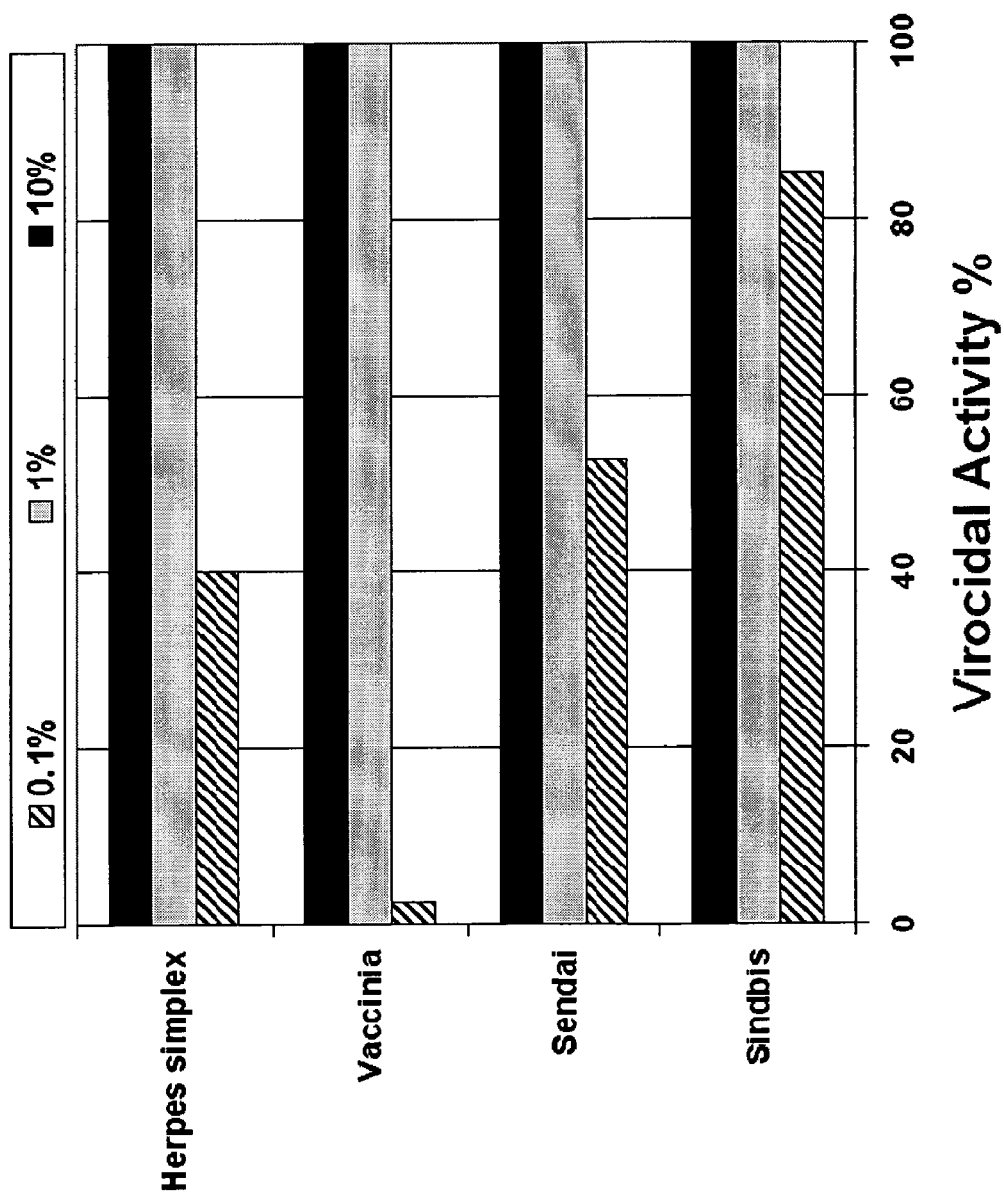

In addition, pre-incubation of virus with 10% and 1% BCTP in PBS completely eliminates herpes, sendai, sindbis and vaccinia viruses as assessed by plaque reduction assays (FIG. 27). Time course analyses showed the onset of inactivation to be rapid and complete within 5 minutes of incubation with 10% BCTP and within 30 minutes with 1% BCTP. Adenovirus treated with different dilutions of BCTP showed no reduction in infectivity.

The efficacy of certain BCTP based compositions against various viral onslaught and their minimal toxicity to mucous membranes demonstrate their potential as effective disinfectants and agents for prevention of diseases resulting from infection with enveloped viruses.

In some embodiments, the nanoemulsions of the present invention are used in conjunction with a low pH buffer. Such nanoemulsions find use as rapid killers of viruses (e.g., rhinovirus or other picornaviruses).

FIG. 31C shows the effectiveness of a number of exemplary nanoemulsions of the present invention against influenza A.

D. Fungicidal and Fungistatic Activity

Yet another property of the nanoemulsions of the present invention is that they possess antifungal activity. Common agents of fungal infections include various species of the genii *Candida* and *Aspergillus*, and types thereof, as well as others. While external fungus infections can be relatively minor, systemic fungal infections can give rise to serious medical consequences. There is an increasing incidence of fungal infections in humans, attributable in part to an increasing number of patients having impaired immune systems. Fungal disease, particularly when systemic, can be life threatening to patients having an impaired immune system.

Experiments conducted during the development of the present invention have shown that 1% BCTP has a greater than 92% fungistatic activity when applied to *Candida albicans*. *Candida* was grown at 37° C. overnight. Cells were then washed and counted using a hemacytometer. A known amount of cells were mixed with different concentrations of BCTP and incubated for 24 hours. The *Candida* was then grown on dextrose agar, incubated overnight, and the colonies were counted. The fungistatic effect of the BCTP was determined as follows:

$$\text{Fungistatic effect } (FSE) = \left(1 - \frac{\# \text{ of treated cells} - \text{Initial} \# \text{ of cells}}{\# \text{ of untreated cells} - \text{Initial} \# \text{ of cells}}\right) \times 100$$

One of skill in the art will be able to take the formulations of the present invention and place them into appropriate formulations for the treatment of fungal disease. The nanoemulsions of the present invention find use in combatting infections such as athletes foot, candidosis and other acute or systemic fungal infections.

E. In Vivo Effects

Animal studies demonstrated the protective and therapeutic effect of the present compositions and methods. *Bacillus cereus* infection in experimental animals has been used previously as a model system for the study of anthrax (See e.g., Burdon and Wende, J Infect. Diseas. 170(2):272 [1960]; Lamanna and Jones, J. Bact. 85:532 [1963]; and Burdon et al., J Infect. Diseas. 117:307 [1967]). The disease syndrome induced in animals experimentally infected with *B. cereus* is similar to anthrax (Drobniewski, Clin. microbio. Rev. 6:324 [1993]; and Fritz et al., Lab. Invest. 73:691 [1995]). Experiments conducted during the development of the present invention demonstrated that mixing BCTP with *B. cereus* spores before injecting into mice prevented the pathological effect of *B. cereus*. Further, it was demonstrated that BCTP treatment of simulated wounds contaminated with *B. cereus* spores markedly reduced the risk of infection and mortality in mice. The control animals, which were injected with BCTP alone diluted 1:10, did not show any inflammatory effects proving that BCTP does not have cutaneous toxicity in mice. These results suggest that immediate treatment of spores prior to or following exposure can effectively reduce the severity of tissue damage of the experimental cutaneous infection.

In a particular example, Guinea Pigs were employed as experimental animals for the study of *C. perfringens* infection. A 1.5 cm skin wound was made, the underlying muscle was crushed and infected with $5 \times 10^7$ cfu of *C. perfringens* without any further treatment. Another group was infected with the same number of bacteria, then 1 hour later it was irrigated with either saline or BCTP to simulate post-exposure decontamination. Irrigation of experimentally infected wounds with saline did not result in any apparent benefit. However, BCTP irrigation of the wound infected with *C. perfingens* showed marked reduction of edema, inflammatory reaction and necrosis. As such, it was demonstrated that certain formulations of the present invention can be used to combat a bacterial infection.

Further, a subcutaneous injection of 10% BCTP did not cause distress in experimental animals and resulted in no gross histological tissue damage. All rats in the oral toxicity study showed weight gain over the study period. No adverse clinical signs were noted and all tissues appeared within normal limits on gross examination. Bacterial cultures from the stools of treated animals were not significantly different from those of untreated animals.

IV. Exemplary Uses

Set forth below are a number of exemplary uses for the compositions disclosed herein: A) Pharmaceuticals and Therapeutics; B) Decontamination and Sterilization; C) Food Preparation; and D) Kits, as well as a description of methods and systems for the E) Modification, Preparation, and Delivery of the compositions of the present invention.

A. Pharmaceuticals and Therapeutics

The present invention contemplates formulations that may be employed in pharmaceutical and therapeutic compositions and applications suitable for combatting and/or treating microbial infections. Such compositions may be employed to reduce infection, kill microbes, inhibit microbial growth or otherwise abrogate the deleterious effects of microbial infection.

For in vivo applications, the compositions can be administered in any effective pharmaceutically acceptable form to warm blooded animals, including human and animal subjects. Generally, this entails preparing compositions that are essentially free of pyrogens, as well as other impurities that could be harmful to humans or animals.

Particular examples of pharmaceutically acceptable forms include but are not limited to oral, nasal, buccal, rectal, vaginal, topical or nasal spray or in any other form effective to deliver active compositions of the present invention to a site of microorganism infection. In preferred embodiments, the route of administration is designed to obtain direct contact of the compositions with the infecting microorganisms. In other embodiments, administration may be by orthotopic, intradermal, subcutaneous, intramuscular or intraperitoneal injection. The compositions may also be administered to subjects parenterally or intraperitonealy. Such compositions would normally be administered as pharmaceutically acceptable compositions. Except insofar as any conventional pharmaceutically acceptable media or agent is incompatible with the emulsions of the present invention, the use of known pharmaceutically acceptable media and agents in these particular embodiments is contemplated. In additional embodiments, supplementary active ingredients also can be incorporated into the compositions.

For topical applications, the pharmaceutically acceptable carrier may take the form of a liquid, cream, foam, lotion, or gel, and may additionally comprise organic solvents, emulsifiers, gelling agents, moisturizers, stabilizers, surfactants, wetting agents, preservatives, time release agents, and minor amounts of humectants, sequestering agents, dyes, perfumes, and other components commonly employed in pharmaceutical compositions for topical administration.

Tablet and dosage forms of the compositions in which the emulsions are formulated for oral or topical administration include liquid capsules, and suppositories. In solid dosage forms for oral administration, the compositions may be admixed with one or more substantially inert diluent (e.g., sucrose, lactose, or starch, and the like) and may additionally comprise lubricating agents, buffering agents, enteric coatings, and other components well known to those skilled in the art.

In another embodiment of the invention, the compositions of the invention may be specifically designed for in vitro applications, such as disinfecting or sterilization of medical instruments and devices, contact lenses and the like, particularly when the devices or lenses are intended to be used in contact with a patient or wearer. For example, the compositions may be used to cleanse and decontaminate medical and surgical instruments and supplies prior to contacting a subject. Additionally, the compositions may be used to postoperatively, or after any invasive procedure, to help minimize the occurrence of post operative infections. In especially preferred embodiments, the compositions are administered to subjects with compromised or ineffective immunological defenses (e.g., the elderly and the very young, burn and trauma victims, and those infected with HIV and the like). For applications of this type, the compositions may be conveniently provided in the form of a liquid, foam, paste or gel and may be provided with emulsifiers, surfactants, buffering agents, wetting agents, preservatives, metal ions, antibiotics and other components commonly found in compositions of this type.

In some embodiments, the compositions are used in association with organ or artificial tissue transplantation or maintenance. For example, the composition may be used on the surface of a transplanted organ to sterilize the organ. The compositions may also be used in conduction with organ preservation or storage solutions (e.g., VIASPAN, Barr Laboratories).

In other embodiments, the compositions may be impregnated into absorptive materials, such as sutures, bandages, and gauze, or coated onto the surface of solid phase materials, such as surgical staples, zippers and catheters to deliver the compositions to a site for the prevention of microbial infection. Other delivery systems of this type will be readily apparent to those skilled in the art.

In yet another embodiment, the compositions can be used in the personal health care industry in deodorants, soaps, acne/dermatophyte treatment agents, treatments for halitosis, treatments for vaginal yeast infections, and the like. The compositions can also be used to treat other internal and external microbial infections (e.g., influenza, H. simplex, toenail fungus, etc.). In these applications, the emulsions can be formulated with therapeutic carriers as described above. In some embodiments, the nanoemulsions of the present invention are formulated into gels, wherein the gels are applied topically.

In certain embodiments, the antimicrobial compositions and methods of the present invention also include a variety of combination therapies. For example, often single antimicrobial agents are much less effective at inhibiting microbes than are several agents employed in conjunction with each other. This approach is often advantageous in avoiding the problems encountered as a result of multidrug resistance. This is particularly prevalent in bacteria that have drug transporters that mediate the efflux of drugs from the organism. The present invention further contemplates the use of the present methods and compositions in such combination therapies.

In some embodiments, the nanoemulsion compositions of the present invention are used as a delivery system for another agent (e.g., a pharmaceutical agent). In some embodiments, the agent has antimicrobial properties. In such embodiments, the nanoemulsions of the present invention increase the antimicrobial effect, compared to the delivery of the agent in the absence of the nanoemulsions of the present invention. However, in some embodiments, the nanoemulsions are used without another antimicrobial agent (i.e., the nanoemulsion itself is the only antimicrobial portion of the composition).

There are an enormous amount of antimicrobial agents currently available for use in treating bacterial, fungal and viral infections. For a comprehensive treatise on the general classes of such drugs and their mechanisms of action, the skilled artisan is referred to Goodman & Gilman's "The Pharmacological Basis of Therapeutics" Eds. Hardman et al., 9th Edition, Pub. McGraw Hill, chapters 43 through 50, 1996, (herein incorporated by reference in its entirety). Generally, these agents include agents that inhibit cell wall synthesis (e.g., penicillins, cephalosporins, cycloserine, vancomycin, bacitracin); and the imidazole antifungal agents (e.g., miconazole, ketoconazole and clotrimazole); agents that act directly to disrupt the cell membrane of the microorganism (e.g., detergents such as polmyxin and colistimethate and the antifungals nystatin and amphotericin B); agents that affect the ribosomal subunits to inhibit protein synthesis (e.g., chloramphenicol, the tetracyclines, erthromycin and clindamycin); agents that alter protein synthesis and lead to cell death (e.g., aminoglycosides); agents that affect nucleic acid metabolism (e.g., the rifamycins and the quinolones); the antimetabolites (e.g., trimethoprim and sulfonamides); and the nucleic acid analogues such as zidovudine, gangcyclovir, vidarabine, and acyclovir which act to inhibit viral enzymes essential for DNA synthesis. Various combinations of antimicrobials may be employed.

Actual amounts of compositions and any enhancing agents in the compositions may be varied so as to obtain amounts of emulsion and enhancing agents at the site of treatment that are effective in killing vegetative as well as sporular microorganisms and neutralizing their toxic products. Accordingly, the selected amounts will depend on the nature and site for treatment, the desired response, the desired duration of biocidal action and other factors. Generally, the emulsion compositions of the invention will comprise at least 0.001% to 100%, preferably 0.01 to 90%, of emulsion per ml of liquid composition. It is envisioned that viral infections may be treated using between about 0.01% to 100% of emulsion per ml of liquid composition. Bacterial infections may be attacked with compositions comprising between about 0.001% to about 100% of emulsion per ml of liquid composition. Spores can be killed by emulsions comprising from about 0.001% to about 100% of emulsion per ml of liquid composition. These are merely exemplary ranges. It is envisioned that the formulations may comprise about 0.001%, about 0.0025%, about 0.005%, about 0.0075%, about 0.01%, about 0.025%, about 0.05%, about 0.075%, about 0.1%, about 0.25%, about 0.5%, about 1.0%, about 2.5%, about 5%, about 7.5%, about 10%, about 12.5%, about 15%, about 20%, about 25%, about 30%, about 35%, about 40%, about 50%, about 55%, about 60%, about 65%, about 70%, about 75%, about 80%, about 85%, about 90%, about 95% or about 100% of emulsion per ml of liquid composition. It should be understood that a range between any two figures listed above is specifically contemplated to be encompassed within the metes and bounds of the present invention. Some variation in dosage will necessarily occur depending on the condition of the subject being treated.

The person responsible for administration will, in any event, determine the appropriate dose for the individual subject. Moreover, for human administration, preparations should meet sterility, pyrogenicity, general safety and purity standards as required by the FDA Office of Biologics standards.

B. Decontamination and Sterilization

In general, the present invention contemplates compositions and methods that find use as environmental decontamination agents and for treatment of casualties in both military and terrorist attack. The inactivation of a broad range of pathogens, including vegetative bacteria and enveloped viruses (See e.g., Chatlyyne et al., "*A lipid emulsion with effective virucidal activity against HIV-1 and other common viruses*," Foundation for Retrovirology and Humna Health, 3rd Conference on retroviruses and Opportunistic Infections, Washington, D.C., U.S.A. [1996]) and bacterial spores, combined with low toxicity in experimental animals, makes the present emulsions suitable for use as general decontamination agents before a specific pathogen is identified. Preferred compositions of the present invention can be rapidly produced in large quantities and are stable for many months at a broad range of temperatures. These properties provide a flexibility that is useful for a broad range of decontamination applications.

For example, certain formulations of the present invention are especially effective at destroying many of the bacterial spores and agents used in biological warfare. In this regard, the compositions and methods of the present are useful in decontaminating personnel and materials contaminated by biological warfare agents. Solutions of present compositions may be sprayed directly onto contaminated materials or personnel from ground based, or aerial spraying systems. In certain of these applications, the present invention contemplates that an effective amount of composition be contacted to contaminated materials or personnel such that decontamination occurs. Alternatively, personal decontamination kits can be supplied to military or civilians likely to become contaminated with biological agents.

The inactivation of a broad range of pathogens, including vegetative bacteria and enveloped viruses (See e.g., Chatlyyne et al., "*A lipid emulsion with effective virucidal activity against HIV-1 and other common viruses*," Foundation for Retrovirology and Humna Health, 3rd Conference on retroviruses and Opportunistic Infections, Washington, D.C., U.S.A. [1996]) and bacterial spores (See e.g., Hamouda et al., J. Infect. Disease 180:1939 [1999]), combined with low toxicity makes the present compositions particularly well suited for use as general decontamination agents before a specific pathogen is identified.

Thus, certain embodiments of the present invention specifically contemplate the use of the present compositions in disinfectants and detergents to decontaminate soil, machinery, vehicles and other equipment, and waterways that may have been subject to an undesired pathogen. Such decontamination procedures may involve simple application of the formulation in the form of a liquid spray or may require a more rigorous regimen. Also, the present emulsions can be used to treat crops for various plant viruses (in place of or for use with conventional antibiotics). Nanoemulsions may also be used to decontaminate farm animals, animal pens, surrounding surfaces, and animal carcasess to eliminate, for example, nonenveloped virus of hoof and mouth disease.

In addition to their use in decontamination of land and equipment, the formulations also find use in household detergents for general disinfectant purposes. Moreover, some embodiments of the present invention can be used to prevent contamination of food with bacteria or fungi (e.g., non-toxic compositions). This can be done either in the food preparation process, or by addition to the food as an additive, disinfectant, or preservative.

The inventive emulsions are preferably used on hard surfaces in liquid form. Accordingly, the foregoing components are admixed with one or more aqueous carrier liquids. The choice of aqueous carrier is not critical. However, it should be safe and it should be chemically compatible with the inventive emulsions. In some embodiments, the aqueous carrier liquid comprises solvents commonly used in hard surface cleaning compositions. Such solvents should be compatible with the inventive emulsions and should be chemically stable at the pH of the emulsions. They should also have good filming/residue properties. Solvents for use in hard surface cleaners are described, for example, in U.S. Pat. No. 5,108, 660, herein incorporated by reference in its entirety.

In preferred embodiments, the aqueous carrier is water or a miscible mixture of alcohol and water. The alcohol can be used to adjust the viscosity of the compositions. In some embodiments, the alcohols are preferably C2-C4 alcohols. In particularly preferred embodiments, ethanol is employed. For example, in one preferred embodiment, the aqueous carrier liquid is water or a water-ethanol mixture containing from about 0 to about 50% ethanol. The present invention also embodies non-liquid compositions. These non-liquid compositions can be in granular, powder or gel forms, preferably in granular forms.

Optionally, some compositions contain auxiliary materials that augment cleaning and aesthetics so long as they do not interfere with the activity of the inventive emulsions. The compositions can optionally comprise a non-interfering auxiliary surfactant. A wide variety of organic, water-soluble surfactants can optionally be employed. The choice of auxiliary surfactant depends on the desires of the user with regard to the intended purpose of the compositions and the commercial availability of the surfactant. Other optional additives such as perfumes, brighteners, enzymes, colorants, and the like can be employed in the compositions to enhance aesthetics and/or cleaning performance. Detergent builders can also be employed in the compositions. Detergent builders sequester calcium and magnesium hardness ions that might otherwise bind with and render less effective the auxiliary surfactants or co-surfactants. Detergent builders are especially useful when auxiliary surfactants or co-surfactants are employed, and are even more useful when the compositions are diluted prior to use with exceptionally hard tap water e.g., above about 12 grains/gallon.

In other embodiments, the composition further comprise, suds suppressors. In these embodiments, the compositions preferably comprise a sufficient amount of a suds suppressor to prevent excessive sudsing when contacting the compositions to hard surfaces. Suds suppressors are especially useful in formulations for no-rinse application of the composition. The suds suppressor can be provided by known and conventional means. Selection of the suds suppressor depends on its ability to formulate in the compositions, and the residue and cleaning profile of the compositions. The suds suppressor must be chemically compatible with the components in the compositions, it must be functional at the pH range described herein, and it should not leave a visible residue on cleaned surfaces. Low-foaming co-surfactants can be used as suds suppressor to mediate the suds profile in the compositions. Co-surfactant concentrations between about 1 part and about 3% are normally sufficient.

Examples of suitable co-surfactants for use herein include block copolymers (e.g., PLURONIC and TETRONIC gels [poly(ethylene oxide)-b-poly(propylene oxide)-b-poly(ethylene oxide) polymer gels, BASF Company, Parispany, N.J.]) and alkylated (e.g., ethoxylated/propoxylated) primary and secondary alcohols (e.g., TERIGTOL [Union Carbide, Danbury, Conn.]; POLY-TERGENTO [Olin Corporation, Norwalk, Conn.]). The optional suds suppressor preferably comprises a silicone-based material. These materials are effective as suds suppressors at very low concentrations. At low concentrations, the silicone-based suds suppressor is less likely to interfere with the cleaning performance of the compositions. An example of suitable silicone-based suds suppressors for use in the compositions is Dow Corning DSE. These optional but preferred silicone-based suds suppressors can be incorporated into the composition by known and conventional means.

In still other embodiments, the compositions may be used by health care workers, or any persons contacting persons or areas with microbial infections, for their personal health-safety and decontamination needs. In addition, the inventive emulsions can be formulated into sprays for hospital and household uses such as cleaning and disinfecting medical devices and patient rooms, household appliances, kitchen and bath surfaces, etc. In similar embodiments, the compositions may be used by sanitation and environmental services workers, food processing and agricultural workers and laboratory personnel when these individuals are likely to contact infectious biological agents. Additionally, the compositions may be used by travelers and persons contacting ares likely to harbor infectious and pathological agents.

C. Food Preparation

The present invention also contemplates that certain compositions described herein may be employed in the food processing and preparation industries in preventing and treating food contaminated with food born bacteria, fungi and toxins. Thus, such compositions may be employed to reduce or inhibit microbial growth or otherwise abrogate the deleterious effects of microbial contamination of food. For these applications, the emulsion compositions are applied in food industry acceptable forms such as additives, preservatives or seasonings.

The phrase "acceptable in the food industry" refers to compositions that do not substantially produce adverse, or allergic reactions when taken orally by humans or animals. As used herein, "acceptable in food industry media" includes any and all solvents, dispersion substances, any and all spices and herbs and their extracts. Except insofar as any conventional additives, preservatives and seasonings are incompatible with the emulsions of the present invention, their use in preventing or treating food born microbes and their toxic products is contemplated. Supplementary active ingredients may also be incorporated into the compositions. For such applications, acceptable carriers may take the form of liquids, creams, foams, gels and may additionally comprise solvents, emulsifiers, gelling agents, moisturizers, stabilizers, wetting agents, preservatives, sequestering agents, dyes, perfumes and other components commonly employed in food processing industry.

In another embodiment of the present invention, the compositions may be specifically designed for applications such as disinfecting or sterilization food industry devices, equipment, and areas where food is processed, packaged and stored. For applications of this type, the compositions may be conveniently provided in the form of a liquid or foam, and may be provided with emulsifiers, surfactants, buffering agents, wetting agents, preservatives, and other components commonly found in compositions of this type. In some embodiments, the compositions are applied to produce or agricultural products prior to or during transportation of those goods. Compositions of the invention may be impregnated into absorptive materials commonly used in packaging material for the prevention of food contamination during transport and storage (e.g., cardboard or paper packaging). Other delivery systems of this type will be readily apparent to those skilled in the art.

Actual amounts of the emulsions and enhancing agents in the compositions of the invention may be varied so as to obtain appropriate concentrations of emulsion and enhancing agents to effectively prevent or inhibit food contamination caused by food born microbes and their toxic products. Accordingly, the selected concentrations will depend on the nature of the food product, packaging, storage procedure and other factors. Generally, the emulsion compositions of the invention will comprise at least 0.001% to about 90% of emulsion in liquid composition. It is envisioned that the formulations may comprise about 0.001%, about 0.0025%, about 0.005%, about 0.0075%, about 0.01%, about 0.025%, about 0.05%, about 0.075%, about 0.1%, about 0.25%, about 0.5%, about 1.0%, about 2.5%, about 5%, about 7.5%, about 10%, about 12.5%, about 15%, about 20%, about 25%, about 30%, about 35%, about 40%, about 50%, about 55%, about 60%, about 65%, about 70%, about 75%, about 80%, about 85%, about 90%, about 95% or about 100% of emulsion per ml of liquid composition. It should be understood that a range between any two figures listed above is specifically contemplated to be encompassed within the metes and bounds of the present invention.

In particular embodiments, emulsions can be used as disinfectants and detergents to decontaminate and prevent microbial infection of food, soil and water, machinery and other equipment, and animals.

The inventive emulsions can be used by the food industry to prevent contamination. For example, inclusion of the emulsion within the food product itself would be effective in killing bacteria that may have been accidentally contaminated meat or poultry. This could also allow the industry to use a potentially broader spectrum of food products and reduce costs.

Certain embodiments of the present invention can also be used in the beverage industry. For example, the inventive emulsions could be included in juice products to prevent growth of certain fungi, which cause contamination and lead to production of mycotoxins, which are dangerous to consumers. Through the addition of small amounts of the inventive emulsions, the most common fungal contaminants in fruit juice were prevented. This effect was achieved with as little as one part in 10,000 of the emulsion (an amount which did not alter the flavor or the composition of the juice product). For example, in some embodiments, contamination of productes such are GATORADE by organisms such as *Byssochlamys fulva* are presented with the use of the nanoemulsions of the present invention.

The inventive emulsions can be used to essentially remove infectious agents on machinery and other equipment. For example, the emulsions can be used to eliminate contaminations in meat processing plants, particularly of organisms such as *Listeria monocytogenes* and Salmonellae microorganisms, by cleaning slaughterhouses or food packaging facilities on a continual basis with the emulsion.

The person responsible for administration will, in any event, determine the appropriate dose for individual application. Moreover, said above application should meet general safety and purity standards as required by the FDA office.

D. Kits

In other embodiments of the present invention, the methods and compositions, or components of the methods and compositions may be formulated in a single formulation, or may be separated into separate formulations for later mixing during use, as may be desired for a particular application. Such components may advantageously be placed in kits for use against microbial infections, decontaminating instruments and the like. In some embodiments, such kits contain all the essential materials and reagents required for the delivery of the formulations of the present invention to the site of their intended action.

In some embodiments, intended for in vivo use, the methods and compositions of the present invention may be formulated into a single or separate pharmaceutically acceptable syringeable compositions. In this case, the container means may itself be an inhalant, syringe, pipette, eye dropper, or other like apparatus, from which the formulation may be applied to an infected area of the body, such as the lungs, injected into an animal, or even applied to and mixed with the other components of the kit.

The kits of the present invention also typically include a means for containing the vials in close confinement for commercial sale (e.g., injection or blow-molded plastic containers into which the desired vials are retained). Irrespective of the number or type of containers, the kits of the invention also may comprise, or be packaged with, an instrument for assisting with the injection/ad ministration or placement of the ultimate complex composition within the body of an animal. Such an instrument may be an inhalant, syringe and antiseptic wipe, pipette, forceps, measured spoon, eyedropper or any such medically approved delivery vehicle.

E. Modification, Preparation, and Delivery

The present invention further provides a variety of methods and systems for the modification of the nanoemulsions of the present invention, the incorporation of the nanoemulsions into other products, packaging and delivery of the compositions of the present invention, and methods for reducing the costs associated with the use or handling of materials or samples that might be contaminated with microorganisms. The following description is intended to simply provide some examples of the modification, preparation, and delivery of the compositions of the present invention. Those skilled in the art will appreciate variations of such methods.

In some embodiments, the present invention provides methods for improving or altering the nanoemulsions described herein. Such methods include, for example, taking a nanoemulsion described herein and changing one or more components of the nanoemulsion. Such changes include, but are not limited to, adding or removing one or more components. The altered nanoemulsion can then be tested to determine if it has desired or useful properties. In some embodiments of the present invention, nanoemulsions of the present invention, or those derived from the nanoemulsions of the present invention are diluted. The diluted samples can then be tested to determine if they maintain the desired functionality. In yet other embodiments of the present invention, the nanoemulsions of the present invention, or those derived from the nanoemulsions of the present invention are pass through a quality control (QC) and/or quality assurance (QA) procedure to confirm the suitability of the nanoemulsion for sale or delivery to a user or retailer.

In some embodiments of the present invention, the nanoemulsions of the present invention are added to another product to add or improve anti-microbial capabilities of the product or to test a suspected or provide a perceived improved anti-microbial capability to the product (i.e., it is contemplated that the addition of a nanoemulsion of the present invention into a product is within the scope of the present invention regardless of whether it has a detectable, or any, antimicrobial capabilities). For example, in some embodiments, the nanoemulsions of the present invention are added to cleaning or disinfectant materials (e.g., household cleaning agents). In other embodiments, the nanoemulsions are added to medical or first aid materials. For example, the nanoemulsions may be added to (or used directly as) sterilization agents and wound care products. In yet other embodiments, the nanoemulsions are added to industrial products. For example, in some embodiments, the nanoemulsions are added to motor oils to prevent or reduce, for example, fungal contamination. As described above, effective, stable emulsion can even be synthesized using motor oil as the oil component (e.g., $W_{20}5GC$ Mobil 1). In still other embodiments, the nanoemulsions are added to food products. For example, the nanoemulsions can be added to beverages to prevent the growth of unwanted organisms in the beverage.

The nanoemulsion of the present invention, whether alone, or in conjunction with other materials can be provided in many different types of containers and delivery systems. For example, in some embodiments of the present invention, the nanoemulsions are provided in a cream or other solid or semi-solid form. During the development of the present invention, it was determined that the emulsions of the present invention may be incorporated into hydrogel formulations while maintaining antimicrobial capabilities. The use of the emulsions in hydrogel provides a number of useful features. For example, hydrogels can be prepared in semi-solid structures of desired sizes and shapes. This allows, for example, the insertion of the hydrogel materials into tubes or other passageways to create antimicrobial filters (i.e., materials passed through the hydrogel are decontaminated by the emulsions of the present invention).

The nanoemulsions can be delivered (e.g., to user or customers) in any suitable container. Container can be used that provide one or more single use or multi-use dosages of the nanoemulsion for the desired application. In some embodiments of the present invention, the nanoemulsions are provided in a suspension or liquid form. Such nanoemulsions can be delivered in any suitable container including spray bottles (e.g., pressurized spray bottles). For industrial or other large-scale uses, large volumes (e.g., tens to thousands of liters) of nanoemulsion may be provided in a single container configured appropriately to allow distribution or use of the nanoemulsion. Such containers may be used in conjunction with large-scale manufacturing facilities.

Figure 34:
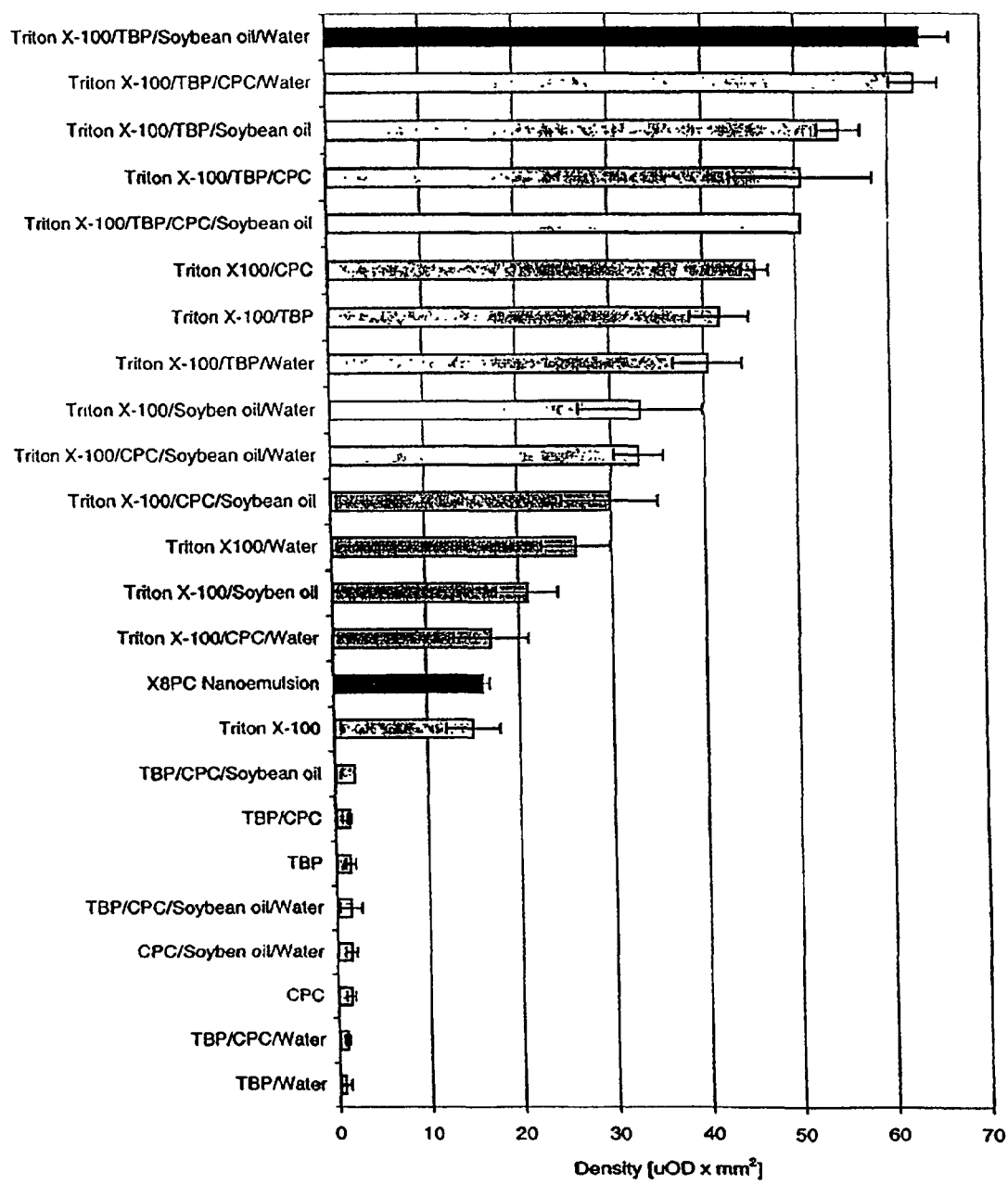

In some preferred embodiments of the present invention, nanoemulsions of the present invention are used in conjunction with an existing business practice to reduce the costs associated with or improve the safety of the operation of the business practice. For example, the use of the nanoemulsions of the present invention can reduce costs associated with the use or handling of materials or samples that might be contaminated with microorganisms. In some embodiments, the nanoemulsions of the present invention are used to improve safety or reduce the costs associated with the medical industries. For example, the nanoemulsions find use as cheap and efficient sterilization agents for use on medical materials (e.g., surface that come in contact with animals, people, or biological samples) or with patients (e.g., internally or externally). The nanoemulsions also find use as cheap and efficient sterilization agents for food processing and handling and industrial applications. In some such embodiments, the present invention provides non-toxic nanoemulsions. For example, nanoemulsions are provided herein that include ingredients that are currently approved by the appropriate regulatory agencies (e.g., FDA, USDA, etc.) for use in medical, agriculture, and food applications. Furthermore, methods are provided herein for the generation of additional nanoemulsions with the desired functionality that can be composed entirely of non-toxic and approved substances. As such, the nanoemulsions of the present invention can be used in applications without incurring having to undergo the time consuming and expensive process of gaining regulatory approval. Indeed, the emulsions can be less toxic than the sum of their individual components. For example, X8PC was tested to compare the lytic effect of the emulsion on sheep red blood cells tested on blood agar plates as compared to the lytic effect of mixtures of the non-emulsified ingredients. The data is present in FIG. 34. The two black bars in FIG. 34 show the lytic effect of the X8PC nanoemulsion compared to the lytic effect of a non-emulsified mixture of all the ingredients.

F. Additional Examples

The nanoemulsions of the present invention may be used alone, or in conjunction with other materials and products to perform specific desired functions. For example, the nanoemulsions may be added to or formulated with health care products, hygiene products, and household products to prevent contamination of the products and/or to add or improve anti-microbial properties of the products. In some embodiments, the functional components of the products are included in the aqueous phase or oil phase of the nanoemulsion (e.g., any of the nanoemulsion compositions described above). Components may be added prior to, during, or following emulsification.

Examples of formulations and uses include (ingredients and concentrations are illustrative; modifications may be made as appropriate or desired): acne treatment (e.g., 0.10% adapalene, 20% azelaic acid, 2.5-20% benzoyl peroxide, 1% clindamycin, 1.5-2% erythromycin, 0.05% isotetrinoin, 1% meclocycline, 4% nicotinamide, 1-3% resorcinol, 0.5-5% salicylic acid, 0.5-5% sulfur, 6% sulfurated lime [dilute 1:10], 2.2 mg/ml tetracycline hydrochloride, and 0.025-0.1% tretinoin); deep pore purifying astringent (Witch Hazel); antacids (e.g., <600 mg/5 ml alumina [aluminum hydroxide], aluminum carbonate, aluminium phosphate, <850 mg/5 ml calcium carbonate, 540 mg/5 ml magaldrate, <500 mg/5 ml magnesia (magnesium hydroxide), magnesium carbonate, magnesium oxide, magnesium trisilicate, sodium bicarbonate, <40 mg/5 ml simethicone); aphthous stomatitis treatment (e.g., corticosteroids, 0.12% chlorhexidine); corticosteroids (e.g., 0.05% alclometasone dipropionat, 0.10% amcinonide, 0.025% beclomethasone dipropionate, 0.01-0.1% betamethasone and derivatives, 0.05% clobetasol propionate and derivatives, 0.05% desonide, 0.25% desoximetasone, 0.10% dexamethasone and derivatives, 0.05% diforasone diacetate, 0.10% diflucortolone valerate, 0.03% flumethasone pivalate, 0.01-0.025% fluocinolone acetonide, 0.01-0-0.05% fluocinonide, 0.025-0.05% flurandrenolide, 0.005% fluticasone propionate, 0.10% halcinonide, 0.05% halobetasol propionate, 0.2-2.5% hydrocortisone derivatives, 0.10% mometasone furonate, 0.025-0.5% triamcinolone acetonide); insect bite treatment/cold sore/local anesthetics (e.g., 5-20% benzocaine, 1% butamben, 0.50% dibucaine, 0.5-5% lidocaine, 1% pramoxine, 1% tetracine, +/−0.50% menthol); burn wound infections (e.g., 85 mg/gm mafenide, 1% silver sulfadiazine, 0.5-1.5% framycetin, 0.01% gramicidin [mixed with framycetin], 2% fusidic acid); calluses treatment (e.g., 2-20% resorcinol, resorcinol+sulfur 2%+5-8%); candidiasis (e.g., 2% butoconazole, 1% ciclopirox, 1-10% clotrimazole, clotrimazole and betamethasone 1% and 0.05%, 150 mg/dose econazole, 2% ketoconozole, 500 mg and 100,000 Units metronidazole and nystatin, 2-5% miconazole, 100,000 Units/Gram nystatin, 100,000 Units and 1 mg/gram nystatin and triamcinolone, 1% sulconazole, 0.4-0.8% terconazole, 6.50% tioconazole); antifungus products (e.g., 3% clioquinol, 1% haloprogin, 1% naftifine, 1% tolnaftate, 1% terbinafine, 1% oxiconazole); Tinea versicolor (e.g., 1% haloprogin, 2% ketoconazole); ODOR GUARD Shoe Deodorizer (e.g., 5.0% Sodium chlorite); dandruff (e.g., 2% chloroxine, 1-25% coal tar, 2% ketoconazole, 1-2% pyrithione, 1-10% salicylic acid, 1-2.5% selenium sulfide); dermatitis/psoriasis (e.g., corticosteroids); folliculitis (e.g., 3% clioquinol); herpes (e.g., 5% acyclovir); impetigo (2% mupirocin); insect repellent (e.g., 7.5-100% diethyltoluamide); moisturizing lotion (e.g., dimethicone, allantoin, camphor, menthol, eucalyptus); mouth infection (e.g., 0.12% chlorhexidine); pediculosis capitis (e.g., 1% lindane [benzyl benzoate]); scabies (e.g., 0.50% malathion, 1-5% permethrin, 0.18-0.33% and 2.2-4% pyrethrins and piperonyl butoxide); scabies (e.g., 10% crotamiton, 0.5-10% sulfur, 6% sulfurated lime); psoriasis (e.g., 0.1-1% anthralin, 0.01% calcipotriene, 1-25%, cool tar, 1% methoxsalen, 1-3% resorcinol); rosacea (e.g., 0.75% metronidazole, 2-10% sulfur); skin infection (Bacterial)/Ulcers (e.g., 1.0% chloramphenicol, 3.0% chlorotetracycline, 1.0% clindamycin, 3.0% clioquinol, 1.5-2% erythromycin, 0.1% gentamycin, 2-7% iodine, 2.0% mupirocin, 0.5% neomycin, 10,000 units/gm polymyxin B, 500 units/gm bacitracin, 1.0% silver sulfadiazine, 3% tetracycline); spermicidal (e.g., nonoxynol 9, nanoxynol 9+/−condom); sunscreen agents (e.g., 5-15% aminobenzoic acid, 3% avobenzone, 3% dioxybenzone, 4-15% homosalate, 2-3% lisadimate, 3.5-5% menthyl anthranilate, 7-10% octocrylene, 2-7.5% octyl mehtoxycinnamate, 3-5% octyl salicylate, 2-6% oxybenzone, 1.4-8% padimate O, 1-4% phenylbenzimidazole sulfonic acid, 1-5% roxadimate, 5-10% sulisobenzone, 2-25% titanium dioxide, 5-12% trolamine salicylate, zinc oxide); toothpaste (e.g., sodium fluoride, sodium monofluorophosphate, amine fluoride, stannous fluoride); teeth whiteners (e.g., hydrogen peroxide, carbopol 956, sodium hydroxide, sodium acid phosphate, sodium stannate); tarter fighting (e.g., polypyrophosphate, tetrasodium pyrophosphate); toothache (e.g., 10-20% benzocaine); teeth sensitivity protection (e.g., baking soda, 5.0% potassium nitrate); mouthwash (e.g., 0.006% lysozyme, 0.006% lactoferrin, 4000 units/100 mL glucose oxidase, 4000 units/100 mL lactoperoxidase); vaginosis (e.g., 2% clindamycin, 0.75-10% metronidazole); warts, common (e.g., 2-20% resorcinol, 13% or 40% salicylic acid); warts, flat (e.g., 0.025-0.1% tretinoin); eye drops (e.g., 70.0% dextran, 0.3% hydroxypropyl methylcellulose 2910, 1.4% polyvinyl alcohol, 0.6% povidone); contact lens cleaners (e.g., 3.0% hydrogen peroxide, citrate, tetronic 1304, AMP-95); contact lens (e.g., sodium chloride, boric acid, sorbitol, edetate disodium); contact lens disinfectant (e.g., 0.0010% polyquad [polyquaternium-1], 0.0005% aldox [myristamidopropyl dimethylamine]); deodorant (e.g., 19.0% aluminum zirconium); anti-bacterial deodorant soap (e.g., triclocarban); diaper Rash (e.g., 40.0% zinc oxide, dimethicone); anti-bacterial wipes for pets (e.g., lidocaine HCl); cat litter (e.g., baking soda); dishwasher detergent (e.g., 2.7% phosphorous, 1.19 g phosphates); tub and shower cleaner (e.g., monocarbamide hydrochloride); glass and surface cleaner (e.g., 3.5% isopropanol, 0.3% propylene glycol); toilet bowl cleaner (e.g., 51.0% 1-Bromo-3-chloro-5,5-dimethylhydantonin, 23.3% 1,3-dichloro-5,5-dimethylhydantonin, 9.0% 1,3-dichloro-5-ethyl-5-methylhydantonin); laundry cleaner (e.g., 5.3% sodium nonanoxloxy benzene sulfonate, 5.3% perboric acid, sodium salt); and pet fresh-carpet cleaner (e.g., 0.3% geraniol, rosemary oil, cedar oil, geranium oil, citronella oil, lemongrass oil, cinnamon oil, mint oil).

Thus, in some embodiments, the present invention provides antimicrobial oil-in-water nanoemulsions having one or more of a first component comprising a solvent (e.g., ethanol, glycerol, polyethylene glycol, isopropanol), a second component comprising a halogen-containing compound (e.g., benzethonium chloride, methylbenzethonium chloride, N-alkyldimethyl benzylammonium chloride), alkyldimethyl-3,4-dichlorobenzyl ammonium chloride, cetypyridinium chloride), a third component comprising a surfactant (e.g., TWEEN-20, TRITON X-100, SDS, Poloxamer, sodium lauryl sulfate), and a fourth component (e.g., an addition surfactant, methanol, EDTA, tribuyl phosphate, tyloxapol, 2-phenylphenol, sodium chloride, trisodium citrate hyhydrate, citric acid, sodium fluoride, peppermint extract, NaOH, L-alanine, inosine, ammonium chloride, PBS, menthol, thymol, eucalyptol, methyl salicylate, triclosan, gycerin, natrosol, benzoyl peroxide, salicyclic acid, citrate buffer, sodium saccharin, tergitol, monoethanolamine, hypertonic saline solution, calcium chloride, hydrogen peroxide, polyamer 407).

V. Experimental Examples

The following examples serve to illustrate certain preferred embodiments and aspects of the present invention and are not to be construed as limiting the scope thereof.

In the experimental disclosure which follows, the following abbreviations apply: eq (equivalents); µ (micron); M (Molar); µM (micromolar); mM (millimolar); N (Normal); mol (moles); mmol (millimoles); µmol (micromoles); nmol (nanomoles); g (grams); mg (milligrams); µg (micrograms); ng (nanograms); L (liters); ml (milliliters); µl (microliters); cm (centimeters); mm (millimeters); µm (micrometers); nM (nanomolar); ° C. (degrees Centigrade); and PBS (phosphate buffered saline).

Example 1

Methods of Formulating Emulsions

The emulsion is produced as follows: an oil phase is made by blending organic solvent, oil, and surfactant and then heating the resulting mixture at 37-90° C. for up to one hour. The emulsion is formed either with a reciprocating syringe instrumentation or Silverson high sheer mixer. The water phase is added to the oil phase and mixed for 1-30 minutes, preferably for 5 minutes. For emulsions containing volatile ingredients, the volatile ingredients are added along with the aqueous phase.

In a particular embodiment, the emulsion was formed as follows: an oil phase was made by blending tri-butyl phosphate, soybean oil, and a surfactant (e.g., TRITON X-100) and then heating the resulting mixture at 86° C. for one hour. An emulsion was then produced by injecting water into the oil phase at a volume/volume ratio of one part oil phase to four parts water. The emulsion can be produced manually, with reciprocating syringe instrumentation, or with batch or continuous flow instrumentation. Methods of producing these emulsions are well known to those of skill in the art and are described in e.g., U.S. Pat. Nos. 5,103,497; and 4,895,452, (herein incorporated by reference in their entireties). Table 2 shows the proportions of each component, the pH, and the size of the emulsion as measured on a Coulter LS 130 laser sizing instrument equipped with a circulating water bath.

TABLE 2

| Chemical Components of Emulsion | Percentage of Each Component | pH | Mean Coulter Size (in Microns) | Mean Coulter Range (in Microns) |
|---|---|---|---|---|
| BCTP | | | | |
| TRITON X-100 | 2% | | | |
| Tributyl phosphate | 2% | 5.16 | 1.074 | 0.758-1.428 |
| Oil (ex. Soybean) | 16% | | | |
| Water | 80% | | | |
| BCTP 0.1* | | | | |
| TRITON X-100 | 0.20% | | | |
| Tributyl phosphate | 0.20% | 5.37 | 0.944 | 0.625-1.333 |
| Oil (ex. Soybean) | 1.60% | | | |
| Water | 98% | | | |

*This emulsion was obtained by diluting the BCTP emulsion with water in a ratio of 1:9

The emulsions of the present invention are highly stable. Indeed, emulsions were produced as described above and allowed to stand overnight at room temperature in sealed 50 to 1000 mL polypropylene tubes. The emulsions were then monitored for signs of separation. Emulsions that showed no signs of separation were considered "stable." Stable emulsions were then monitored over 1 year and were found to maintain stability.

Emulsions were again produced as described above and allowed to stand overnight at −20° C. in sealed 50 mL polypropylene tubes. The emulsions were then monitored for signs of separation. Emulsions that showed no signs of separation were considered "stable." The BCTP and BCTP 0.1, emulsions have been found to be substantially unchanged after storage at room temperature for at least 24 months.

Example 2

Characterization of an Exemplary Bacteria-inactivating Emulsion of the Present Invention as an Emulsified Liposome Formed in Lipid Droplets A bacteria inactivating emulsion of the present invention, designated $X_8W_{60}PC$, was formed by mixing a lipid-containing oil-in-water emulsion with BCTP. In particular, a lipid-containing oil-in-water emulsion having glycerol monooleate (GMO) as the primary lipid and cetylpyridinium chloride (CPC) as a positive charge producing agent (referred to herein as GMO/CPC lipid emulsion or "$W_{80}8P$") and BCTP were mixed in a 1:1 (volume to volume) ratio. U.S. Pat. No. 5,547, 677 (herein incorporated by reference in its entirety), describes the GMO/CPC lipid emulsion and other related lipid emulsions that may be combined with BCTP to provide the bacteria-inactivating oil-in-water emulsions of the present invention.

Example 3

In Vitro Bactericidal Efficacy Study I

Gram Positive Bacteria

In order to study the bactericidal efficacy of the emulsions of the present invention, the emulsions were mixed with various bacteria for 10 minutes and then plated on standard microbiological media at varying dilutions. Colony counts were then compared to untreated cultures to determine the percent of bacteria killed by the treatment. Table 3 summarizes the results of the experiment.

TABLE 3

| Organism | Inoculum (CFU) | % Killing | Emulsion Tested |
|---|---|---|---|
| Vibrio cholerae classical | $1.3 \times 10^8$ | 100 | BCTP |
| Vibrio cholerae Eltor | $5.1 \times 10^8$ | 100 | BCTP |
| Vibtio parahemolytica | $4.0 \times 10^7$ | 98-100 | BCTP |

In order to study the bactericidal effect of the emulsions of the present invention on various vegetative forms of Bacillus species, an emulsion at three dilutions was mixed with four Bacillus species for 10 minutes and then plated on microbiological medium. Colony counts were then compared with untreated cultures to determine the percent of bacteria killed by the treatment. Table 4 contains a summary of the bactericidal results from several experiments with the mean percentage kill in parenthesis.

TABLE 4

| BCTP/ Dilution | B. cerous | B. circulans | B. megaterium | B. subtilus |
|---|---|---|---|---|
| 1:10 | 99% (99%) | 95-99% (97%) | 99% (99%) | 99% (99%) |
| 1:100 | 97-99% (98%) | 74-93% (84%) | 96-97% (96%) | 99% (99%) |
| 1:1000 | 0% (0%) | 45-60% (52%) | 0-32% (16%) | 0-39% (20%) |

Example 4

In Vitro Bactericidal Efficacy Study II

Gram Negative Bacteria

To increase the uptake of the bacteria inactivating emulsions by the cell walls of Gram negative bacteria, thereby enhancing the microbicidal effect of the emulsions on the resistant Gram negative bacteria, EDTA (ethylenediaminetetraacetic acid) was premixed with the emulsions. The EDTA was used in low concentration (50-25 μM) and the mix was incubated with the various Gram negative bacteria for 15 minutes. The microbicidal effect of the mix was then measured on trypticase soy broth. The results are set forth in Table 5 below. There was over 99% reduction of the bacterial count using BCTP in 1/100 dilutions. This reduction of count was not due to the killing effect of EDTA alone as shown from the control group in which 250 μM of EDTA alone could not reduce the bacterial count in 15 minutes.

TABLE 5

| Bacterium | Bacteria alone (CFU) | Bacteria + BCTP (CFU) | Bacteria + BCTP + EDTA (CFU) | Bacteria + EDTA (CFU) |
|---|---|---|---|---|
| S. typhimunium | 1,830,000 | 1,370,000 | 40 | 790,000 |
| S. dysenteriae | 910,000 | 690,000 | 0 | 320,000 |

Example 5

In Vitro Bactericidal Efficacy Study III

Vegetative and Spore Forms

Bacillus cereus (B. cereus, ATCC #14579) was utilized as a model system for Bacillus anthracis. Experiments with BCTP diluted preparations to study the bactericidal effect of the compounds of the present invention on the vegetative form (actively growing) of B. cereus were performed. Treatment in medium for 10 minutes at 37° C. was evaluated. As summarized in Table 6, the BCTP emulsion is efficacious against the vegetative form of B. cereus. A 10 minute exposure with this preparation is sufficient for virtually complete killing of vegetative forms of B. cereus at all concentrations tested including dilutions as high as 1:100.

TABLE 6

| Emulsion | Undiluted | 1:10 | 1:100 |
|---|---|---|---|
| BCTP | >99%<br>Avg = >99% | >99%<br>Avg = >99% | 59->99%<br>Avg = 82% |

Number of experiments = 4

The spore form of B. anthracis is one of the most likely organisms to be used as a biological weapon. Spores are well known to be highly resistant to most disinfectants. As describe above, effective killing of spores usually requires the use of toxic and irritating chemicals such as formaldehyde or sodium hypochlorite (i.e., bleach). The same experiment was therefore performed with the spore form of B. cereus. As shown in Table 7, treatment in both medium for 10 minutes at 37° C. was not sufficient to kill B. cereus spores.

TABLE 7

| Emulsion | Undiluted | 1:10 | 1:100 |
|---|---|---|---|
| BCTP | 0%-12%<br>Avg = 6% | 0%<br>Avg = 0% | 0%<br>Avg = 0% |

Number of experiments = 2

To evaluate the efficacy of the compounds of the present invention on the spore form of B. cereus over a period of time, BCTP was incorporated into solid agar medium at 1:100 dilution and the spores spread uniformly on the surface and incubated for 96 hours at 37° C. No growth occurred on solid agar medium wherein BCTP had been incorporated, out to 96 hours (i.e., >99% killing, average >99% killing, 3 experiments).

Figure 2A:
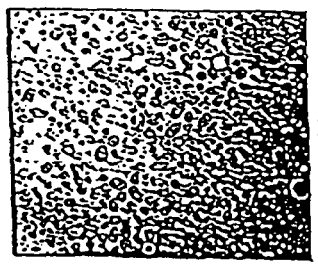
FIG. 2A-FIG. 2C illustrate bacterial smears showing the bactericidal efficacy of an emulsion of the present invention on *B. cereus* spores.
Figure 2B:
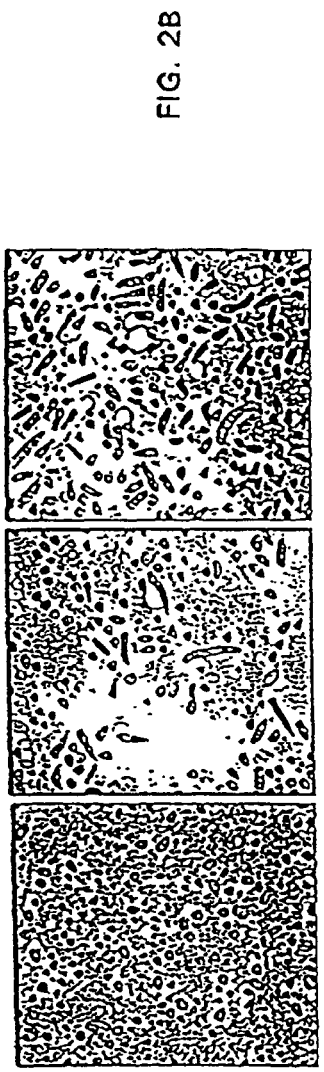
Figure 2C:
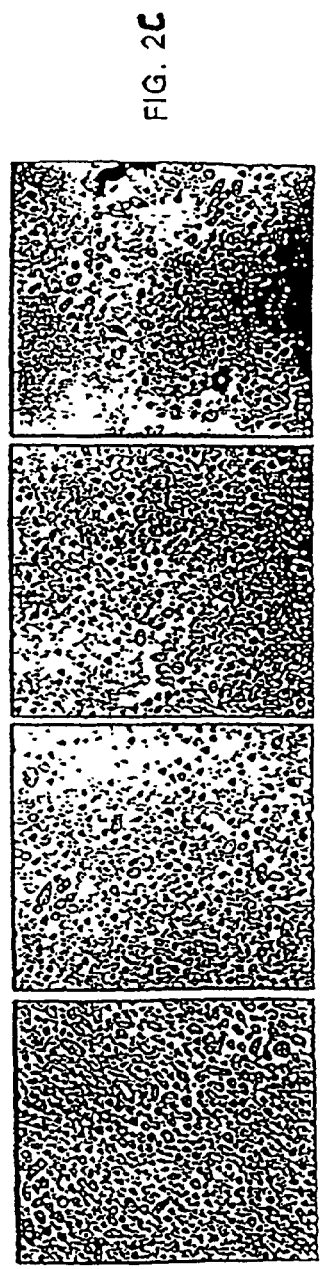

In an attempt to more closely define the time at which killing of spores by BCTP occurred, the following experiment was performed. Briefly, a spore preparation was treated with BCTP at a dilution of 1:100 and compared to an untreated control. The number of colony forming units per milliliter (CFU/ml) was quantitated after 0.5, 1, 2, 4, 6, and 8 hours. As shown in FIG. 1, CFU/ml in the untreated control increased over the first 4 hours of incubation and then reached a plateau. Bacterial smears prepared at time zero, 1, 2, 4 and 6 hours, and stained for spore structures, revealed that by 2 hours no spore structures remained (FIGS. 2A-2C). Thus, 100% germination of spores occurred in the untreated control by the 2 hour time point. In the spore preparation treated with BCTP, CFU/ml showed no increase over the first 2 hours and then declined rapidly over the time period from 2-4 hours. The decline from baseline CFU/ml over 2-4 hours was approximately 1000-fold. Bacterial smears prepared at the same time points and stained for spore structures revealed that spore structures remained to the end of the experiment at 8 hours. Hence, germination of spores did not occur in the BCTP treated culture due to either inhibition of the germination process or because the spores were damaged and unable to germinate. In order to determine whether the emulsions were effective in killing other Bacillus species in addition to B. cereus, a similar experiment was performed as described above, wherein spore preparations were treated with emulsions and compared to an untreated control after four hours of incubation. The following Table 8 shows the results wherein the numbers represent the mean sporicidal activity from several experiments.

TABLE 8

| BCTP/Dilution | B. cereus | B. circulans | B. megaterium | B. subtlius |
|---|---|---|---|---|
| 1:10 | 82% | 61% | 93% | 31% |
| 1:100 | 91% | 80% | 92% | 39% |
| 1:1000 | 47% | 73% | 94% | 22% |

Example 6

In Vivo Bactericidal Efficacy Study

Animal studies were preformed to demonstrate the protective and therapeutic effect of the inventive emulsions in vivo. Bacillus cereus infection in experimental animals has been used previously as a model system for the study of anthrax (Burdon and Wende, 1960; Burdon et al., 1967; Lamanna and Jones, 1963). The disease syndrome induced in animals experimentally infected with B. cereusis in some respects similar to anthrax (Drobniewski, 1993; Fritz et al., 1995). The inventive emulsions were mixed with B. cereus spores before injecting into mice.

Irrigation of Skin Wounds

A 1 cm skin wound was infected with $2.5 \times 10^7$ B. cereus spores then closed without any further treatment. The other groups were infected with the same number of spores. One hour later, the wounds were irrigated with either inventive emulsion or saline to simulate post-exposure decontamination. By 48 hours, there were large necrotic areas surrounding the wounds with an average area of 4.86 cm². In addition, 60% of the animals in this group died as a result of the infection. Histology of these lesions indicated total necrosis of the dermis and subdermis and large numbers of vegetative *Bacillus* organisms. Irrigation of experimentally infected wounds with saline did not result in any apparent benefit.

Irrigation of wounds infected with *B. cereus* spores with inventive emulsion showed substantial benefit, resulting in a consistent 98% reduction in the lesion size from 4.86 cm² to 0.06 cm². This reduction in lesion size was accompanied by a three-fold reduction in mortality (60% to 20%) when compared to experimental animals receiving either no treatment or saline irrigation. Histology of these lesions showed no evidence of vegetative *Bacillus* organisms and minimal disruption of the epidermis (Hamouda et al., 1999).

Subcutaneous Injection

CD-1 mice were injected with inventive emulsion diluted 1:10 in saline as a control and did not exhibit signs of distress or inflammatory reaction, either in gross or histological analysis. To test the pathogenic effect of *B. cereus* spores in vivo and the sporicidal effect of inventive emulsion, a suspension of 4×10⁷ *B. cereus* spores was mixed with saline or with inventive emulsion at a final dilution of 1:10 and then immediately injected subcutaneously into the back of CD-1 mice.

Mice that were infected subcutaneously with *B. cereus* spores without inventive emulsion developed severe edema at 6-8 hours. This was followed by a gray, necrotic area surrounding the injection site at 18-24 hours, with severe sloughing of the skin present by 48 hours, leaving a dry, red-colored lesion.

Simultaneous injection of spores and inventive emulsion resulted in a greater than 98% reduction in the size of the necrotic lesion from 1.68 cm² to 0.02 cm² when the spores were premixed with inventive emulsion. This was associated with minimal edema or inflammation (Hamouda et al., 1999).

Rabbit Cornea

The cornea of rabbits were irrigated with various concentrations of the inventive emulsions and monitored at 24 and 48 hours. No irritations or abnormalities were observed when compositions were used in therapeutic amounts.

Mucous Membrane

Intranasal toxicity was preformed in mice by installation of 25 μL of 4% of the nanoemulsion per nare. No clinical or histopathological changes were observed in these mice.

Oral toxicity testing in rats was performed by gavaging up to 8 mL per kg of 25% nanoemulsion. The rats did not lose weight or show signs of toxicity either clinically or histopathologically. There were no observed changes in the gut bacterial flora as a result of oral administration of the emulsions.

In a particular embodiment, *Bacillus cereus* was passed three times on blood agar (TSA with 5% sheep blood, REMEL). *B. cereus* was scraped from the third passage plate and resuspended in trypticase soy broth (TSB) (available from BBL). The *B. cereus* suspension was divided into two tubes. An equal volume of sterile saline was added to one tube and mixed 0.1 cc of the *B. cereus* suspension/saline was injected subcutaneously into 5 CD-1 mice. An equal volume of BCTP (diluted 1:5 in sterile saline) was added to one tube and mixed, giving a final dilution of BCTP at 1:10. The *B. cereus* suspension/BCTP was incubated at 37° C. for 10 minutes while being mixed 0.1 cc of the *B. cereus* suspension/BCTP was injected subcutaneously into 5 CD-1 mice. Equal volumes of BCTP (diluted 1:5 in sterile saline) and TSB were mixed, giving a final dilution of BCTP at 1:10. 0.1 cc of the BCTP/TSB was injected subcutaneously into 5 CD-1 mice.

The number of colony forming units (cfu) of *B. cereus* in the inocula were quantitated as follows: 10-fold serial dilutions of the *B. cereus* and *B. cereus*/BCTP suspensions were made in distilled H₂0. Duplicate plates of TSA were inoculated from each dilution (10 μl per plate). The TSA plates were incubated overnight at 37° C. Colony counts were made and the number of cfu/cc was calculated. Necrotic lesions appears to be smaller in mice which were inoculated with *B. cereus* which was pretreated with BCTP. The following Table 9 shows the results of the experiment.

TABLE 9

| Inoculum | ID# | Observation (24 hours) |
|---|---|---|
| *B. cereus* 3.1 × 10⁷ cfu/mouse | 1528 | necrosis at injection site |
| | 1529 | necrosis at injection site |
| | 1530 | dead |
| | 1531 | dead |
| | 1532 | necrosis at injection site |
| *B. cereus* 8.0 × 10⁵ cfu/mouse (BCTP treated) | 1348 | necrosis at injection site |
| | 1349 | no reaction |
| | 1360 | no reaction |
| | 1526 | necrosis at injection site |
| | 1527 | necrosis at injection site |
| BCTP/TSB | 1326 | no reaction |
| | 1400 | no reaction |
| | 1375 | no reaction |
| | 1346 | no reaction |
| | 1347 | no reaction |

*Bacillus cereus* was grown on Nutrient Agar (Difco) with 0.1% Yeast Extract (Difco) and 50 μg/ml MnSO₄ for induction of spore formation. The plate was scraped and suspended in sterile 50% ethanol and incubated at room temperature for 2 hours with agitation in order to lyse remaining vegetative bacteria. The suspension was centrifuged at 2,500×g for 20 minutes and the supernatant discarded. The pellet was resuspended in diH₂O, centrifuged at 2,500×g for 20 minutes, and the supernatant discarded. The spore suspension was divided. The pellet was resuspended in TSB. 0.1 cc of the *B. cereus* spore suspension diluted 1:2 with saline was injected subcutaneously into 3 CD-1 mice. Equal volumes of BCTP (diluted 1:5 in sterile saline) and *B. cereus* spore suspension were mixed, giving a final dilution of BCTP at 1:10 (preincubation time). 0.1 cc of the BCTP/*B. cereus* spore suspension was injected subcutaneously into 3 CD-1 mice. The number of colony forming units (cfu) of *B. cereus* in the inoculum was quantitated as follows. 10-fold serial dilutions of the *B. cereus* and *B. cereus*/BCTP suspensions were made in distilled H₂O. Duplicate plates of TSA were inoculated from each dilution (10 μl per plate). The TSA plates were incubated overnight at 37° C. Colony counts were made and the number of cfu/cc was calculated. Necrotic lesions appeared to be smaller in mice which were inoculated with *B. cereus* spores which were pretreated with BCTP. The observations from these studies are shown in Table 10.

TABLE 10

| Inoculum | Observation (24 hours) |
|---|---|
| *B. cereus* 6.4 × 10⁶ spores/mouse | 2/3 (66%) mice exhibited necrosis at injection site |

TABLE 10-continued

| Inoculum | Observation (24 hours) |
|---|---|
| B. cereus 4.8 × 10$^6$ spores/mouse (BCTP treated) | 1/3 (33%) mice exhibited necrosis at injection site |
| B. cereus 4.8 × 10$^6$ vegetative forms/mouse | 3/3 (100%) mice exhibited necrosis at injection site |
| Lysed B. cereus 4.8 × 10$^6$ cfu/mouse | 3/3 (100%) mice did not exhibit symptoms |
| BCTP/TSB | 1/3 (33%) mice appeared to have some skin necrosis |

*Bacillus cereus* was grown on Nutrient Agar (Difco) with 0.1% Yeast Extract (Difco) and 50 (g/ml MnSO$_4$ for induction of spore formation). The plate was scraped and suspended in sterile 50% ethanol and incubated at room temperature for 2 hours with agitation in order to lyse remaining vegetative bacteria. The suspension was centrifuged at 2,500×g for 20 minutes and the supernatant discarded. The pellet was resuspended in distilled H$_2$O, centrifuged at 2,500×g for 20 minutes, and the supernatant discarded. The pellet was resuspended in TSB. The *B. cereus* spore suspension was divided into three tubes. An equal volume of sterile saline was added to one tube and mixed. 0.1 cc of the *B. cereus* suspension/saline was injected subcutaneously into 10 CD-1 mice. An equal volume of BCTP (diluted 1:5 in sterile saline) was added to the second tube and mixed, giving a final dilution of BCTP at 1:10. The *B. cereus* spore suspension/BCTP (1:10) was incubated at 37° C. for 4 hours while being mixed. 0.1 cc of the *B. cereus* spore suspension/BCTP (1:10) was injected subcutaneously into 10 CD-1 mice. An equal volume of BCTP (diluted 1:50 in sterile saline) was added to the third tube and mixed, giving a final dilution of BCTP at 1:100. The *B. cereus* spore suspension/BCTP (1:100) was incubated at 37° C. for 4 hours while being mixed. 0.1 cc of the *B. cereus* spore suspension/BCTP (1:100) was injected subcutaneously into 10 CD-1 mice. Equal volumes of BCTP (diluted 1:5 in sterile saline) and TSB were mixed, giving a final dilution of BCTP at 1:10. 0.1 cc of the BCTPFTSB was injected subcutaneously into 10 CD-1 mice. Equal volumes of BCTP (diluted 1:50 in sterile saline) and TSB were mixed, giving a final dilution of BCTP at 1:100. 0.1 cc of the BCTP/TSB was injected subcutaneously into 10 CD-1 mice. The observations form these studies are shown in Table 11 and Table 12.

TABLE 11

| Inoculum sc | ID# | Observation at 24 hours |
|---|---|---|
| *B. cereus* $5.5 \times 10^7$ Spores/mouse No treatment group | 1 | 2.4 $cm^2$ skin lesion with 0.08 $cm^2$ necrotic area |
| | 2 | no abnormalities observed |
| | 3 | Moribund with 8 $cm^2$ skin lesion and hind |
| | 4 | limb paralysis |
| | 5 | 3.52 $cm^2$ skin lesion |
| | 6 | 1.44 $cm^2$ skin lesion |
| | 7 | 3.4 $cm^2$ skin lesion |
| | 8 | 5.5 $cm^2$ skin lesion |
| | 9 | 5.5 $cm^2$ skin lesion |
| | 10 | 3.3 $cm^2$ skin lesion with 0.72 $cm^2$ necrotic area |
| | | 2.64 $cm^2$ skin lesion with two necrotic areas (0.33 $cm^2$ and 0.1 $cm^2$) |
| | | Mean lesion size in Spore group alone 3.97 $cm^2$ (1/10 (10%) with no abnormalities observed) |

Note:
Skin lesions grey in color with edema, necrotic areas red/dry.

TABLE 12

| Inoculum sc | ID # | Observation at 24 hours |
|---|---|---|
| *B. cereus* $2.8 \times 10^7$ spores/mouse in the BCTP 1:10 treated group | 41 | no abnormalities observed |
| | 42 | no abnormalities observed |
| | 43 | 1.2 $cm^2$ white skin lesion with grey center, slight edema |
| | 44 | 0.78 $cm^2$ white skin lesion |
| | 45 | 0.13 $cm^2$ white skin lesion |
| | 46 | 2.2 $cm^2$ white skin lesion |
| | 47 | 1.8 $cm^2$ white skin lesion with 0.1 $cm^2$ brown area in center |
| | 48 | 1 $cm^2$ white skin lesion with grey center |
| | 49 | 0.78 $cm^2$ white skin lesion |
| | 50 | no abnormalities observed |
| | | Mean lesion size in BCTP 1:10 treatment group = 1.13 $cm^2$ (3/10 (30%) with no abnormalities observed) |
| *B. cereus* $1.8 \times 10^7$ spores/mouse in the BCTP 1:100 treated group | 51 | 2.1 $cm^2$ grey skin lesion |
| | 52 | 0.72 $cm^2$ grey skin lesion |
| | 53 | 1.5 $cm^2$ grey skin lesion |
| | 54 | 1.2 $cm^2$ grey skin lesion |
| | 55 | 3.15 $cm^2$ grey skin lesion |
| | 56 | 0.6 $cm^2$ grey skin lesion |
| | 57 | 0.5 $cm^2$ grey skin lesion |
| | 58 | 2.25 $cm^2$ grey skin lesion |
| | 59 | 4.8 $cm^2$ grey skin lesion with necrotic area 1 cm diameter |
| | 60 | 2.7 $cm^2$ grey skin lesion |
| | | Mean lesion size In BCTP 1:100 treatment group = 1.9 $cm^2$ (0/10 (0%) with no abnormalities observed) |
| BCTP 1:10 alone | 11 | 2.6 $cm^2$ white area |
| | 12 | 0.15 $cm^2$ white area |
| | 13 | no abnormalities observed |
| | 14 | 0.15 $cm^2$ white area |
| | 15 | 0.35 $cm^2$ white area |
| | 16 | no abnormalities observed |
| | 17 | 0.12 $cm^2$ white area |
| | 18 | no abnormalities observed |
| | 19 | 0.56 $cm^2$ white area |
| | 20 | 0.3 $cm^2$ white area |
| | | Mean lesion size In BCTP 1:10 alone group = 0.60 $cm^2$ (3/10 (30%) with no abnormalities observed) |
| BCTP 1:100 alone | 21-30 | no abnormalities observed |
| | | Mean lesion size in BCTP 1:100 alone group = 0 $cm^2$ (10/10 (100%) with no abnormalities observed) |
| TSB alone | 31-40 | no abnormalities observed |
| | | Mean lesion size In the TSB alone group = 0 $cm^2$ (10/10 (100%) with no abnormalities observed) |

Re-isolation of *B. cereus* was attempted from skin lesions, blood, liver, and spleen (Table 13). Skin lesions were cleansed with betadine followed by 70% sterile isopropyl alcohol. An incision was made at the margin of the lesion and swabbed. The chest was cleansed with betadine followed by 70% sterile isopropyl alcohol. Blood was drawn by cardiac puncture. The abdomen was cleansed with betadine followed by 70% sterile isopropyl alcohol. The skin and abdominal muscles were opened with separate sterile instruments. Samples of liver and spleen were removed using separate sterile instruments. Liver and spleen samples were passed briefly through a flame and cut using sterile instruments. The freshly exposed surface was used for culture. BHI agar (Difco) was inoculated and incubated aerobically at 37° C. overnight.

TABLE 13

| Inoculum sc | ID# | Necrospy | B. cereus Re-isolation from site of skin lesion |
|---|---|---|---|
| B. cereus | 3 | 24 hours | skin lesion >300 cfu |
| $5.5 \times 10^7$ | 6 | 48 hours | skin lesion >300 cfu |
| spores/mouse | 7 | 48 hours | skin lesion >300 cfu |
| in the | 8 | 72 hours | skin lesion 100 cfu |
| Untreated group | 9 | 72 hours | skin lesion 25 cfu |
| | 10 | 72 hours | skin lesion 100 |
| | 1 | 96 hours | skin lesion >300 cfu |
| | 4 | 96 hours | skin lesion >300 cfu |
| | 5 | 96 hours | skin lesion >300 cfu |
| | | | Mean CFU In Untreated Spore group = 214* *(6/9 (67%)>300 CFU) |
| B. cereus | 48 | 48 hours | skin lesion 17 cfu |
| $2.8 \times 10^7$ | 50 | 48 hours | skin lesion >300 cfu |
| spores/mouse | 46 | 72 hours | skin lesion >200 cfu |
| in the | 47 | 72 hours | skin lesion 100 cfu |
| BCTP 1:10 | 49 | 72 hours | skin lesion >300 cfu |
| treated group | 41 | 96 hours | skin lesion >300 cfu |
| | 42* | 96 hours | skin lesion 20 cfu |
| | 43 | | cultures not done |
| | 44 | 96 hours | skin lesion >300 cfu |
| | 45 | | cultures not done |
| | 46 | | cultures not done |
| | | | Mean CFU in BCTP 1:10 group = 192* *(3l8 (38%)>300 CFU) |
| B. cereus | 48 | 48 hours | skin lesion 18 cfu |
| $1.8 \times 10^7$ | 50* | 48 hours | skin lesion >300 cfu |
| spores/mouse | 52 | 72 hours | skin lesion l cfu |
| in the | 54 | 72 hours | re-isolation negative |
| BCTP 1:100 | 56 | 72 hours | skin lesion >300 cfu |
| treated group | 58 | 96 hours | skin lesion 173 cfu |
| | 59 | 96 hours | skin lesion 4 cfu |
| | 60 | 96 hours | skin lesion 6 cfu |
| | | | Mean CFU in BCTP 1:100 group = 100 *(2/8 (25%)>00 CFU) |

*Although no lesions were present in these mice, organisms were removed from the injection site.

Pretreatment of both vegetative *B. cereus* and *B. cereus* spores reduce their ability to cause disease symptoms when introduced into experimental animals. This is reflected in the smaller size of skin lesions and the generally lower numbers of *B. cereus* recovered from the lesions. In addition, less frequent re-isolation of *B. cereus* from blood, liver, and spleen occurs suggesting that septicemia may be preventable.

Example 7

In Vivo Toxicity Study I

CD-1 mice were injected subcutaneously with 0.1 cc of the compounds of the present invention and observed for 4 days for signs of inflammation and/or necrosis. Dilutions of the compounds were made in sterile saline. Tissue samples from mice were preserved in 10% neutral buffered formalin for histopathologic examination. Samples of skin and muscle (from mice which were injected with undiluted compounds) sent for histological review were reported to show indications of tissue necrosis. Tissue samples from mice which were injected with diluted compounds were not histologically examined. Tables 14 and 15 show the results of two individual experiments.

TABLE 14

| Compound | Mouse ID # | Dilution | Observation |
|---|---|---|---|
| BCTP | 1326 | undiluted | necrosis |
| | 1327 | undiluted | no reaction |
| | 1328 | 1:10 | no reaction |
| | 1329 | 1:10 | no reaction |
| | 1324 | 1:100 | no reaction |
| | 1331 | 1:100 | no reaction |
| Saline | 1344 | | no reaction |
| | 1345 | | no reaction |

TABLE 15

| Compound | Mouse ID # | Dilution | Observation |
|---|---|---|---|
| BCTP | 1376 | undiluted | necrosis |
| | 1377 | undiluted | minimal necrosis |
| | 1378 | 1:10 | no reaction |
| | 1379 | 1:10 | no reaction |
| | 1380 | 1:100 | no reaction |
| | 1381 | 1:100 | no reaction |
| Saline | 1394 | | no reaction |
| | 1395 | | no reaction |

Guinea pigs were injected intramuscularly (in both hind legs) with 1.0 cc of compounds of the present invention per site and observed for 4 days for signs of inflammation and/or necrosis. Dilutions of the compounds were made in sterile saline. Tissue samples from guinea pigs were preserved in 10% neutral buffered formalin for histological examination. Tissue samples were not histologically examined.

TABLE 16

| Compound | Guinea Pig | Dilution | Observation |
|---|---|---|---|
| BCTP | 1023-1 | undiluted | no reaction |
| | 1023-2 | 1:10 | no reaction |
| | 1023-3 | 1:100 | no reaction |
| Saline | 1023-10 | | no reaction |

The results of In Vivo Toxicity Study I show that subcutaneous and intramuscular injection of the compounds tested did not result in grossly observable tissue damage and did not appear to cause distress in the experimental animals (Table 16).

Example 8

In Vivo Toxicity Study II

One group of Sprague-Dawley rats each consisting of five males and five females were placed in individual cages and acclimated for five days before dosing. Rats were dosed daily for 14 days. On day 0-13, for 14 consecutive days each rat in Group 1 received by gavage three milliliters of BCTP, 1:100 concentration, respectively. The three-milliliter volume was determined to be the maximum allowable oral dose for rats. Prior to dosing on Day 0 and Day 7, each rat was weighed. Thereafter rats were weighed weekly for the duration of the study. Animals were observed daily for sickness or mortality. Animals were allowed to rest for 14 days. On Day 28 the rats were weighed and euthanized. The mean weight results of the oral toxicity study are shown in Table 17. Mean weights for males and females on Days 0, 7, and 14, 21 and 28 and the mean weight gains from Day 0-Day 28, are also shown in Table 17. One rat died due to mechanical trauma from manipulation of the gavage tubing during dosing on Day 14.

All surviving rats gained weight over the 28 day course of the study and there was no illness reported. Thus, although tributyl phosphate alone is known to be toxic and irritating to mucous membranes, when incorporated into the emulsions of the present invention, these characteristics are not in evidence. The BCTP emulsion, 1:100 concentration, was also tested for dermal toxicity in rabbits according to the protocols provided in 16 CFR §1500.3. The emulsion was not irritating to skin in the animals tested.

TABLE 17

| Rat Number | Sex | Dose Volume mL | Body Weight (g) Day 0 | Body Weight (g) Day 7 | Body Weight (g) Day 14 | Body Weight (g) Day 21 | Body Weight (g) Day 28 | Weight Gain (g) Day 0 Day 28 |
|---|---|---|---|---|---|---|---|---|
| 9028 | m | 3 | 332.01 | 356.52 | 388.66 | 429.9 | 394.07 | 62.06 |
| 9029 | m | 3 | 278.62 | 294.65 | 296.23 | 310.7 | 392.6 | 113.98 |
| 9030 | m | 3 | 329.02 | 360.67 | 325.26 | 403.43 | 443.16 | 114.14 |
| 9031 | m | 3 | 334.64 | 297.04 | 338.82 | 357.5 | 416.89 | 82.25 |
| 9032 | m | 3 | 339.03 | 394.39 | 347.9 | 331.38 | 357.53 | 18.5 |
| MEAN WTS | | | 266.26 | 340.65 | 339.37 | 400.85 | 78.18 | |
| 9063 | F | 3 | 302 | 298.08 | 388.66 | 338.41 | 347.98 | 45.98 |
| 9064 | F | 3 | 254.54 | 247.97 | 256.78 | 278.17 | 279.2 | 24.66 |
| 9065 | F | 3 | 225.99 | 253.81 | 273.38 | 290.54 | 308.68 | 82.69 |
| 9066 | F | 3 | 246.56 | 260.38 | 266.21 | 235.12 | 272.6 | 26.04 |
| 9067 | F | 3 | 279.39 | 250.97 | deceased | | | |
| MEAN WTS | | | 261.69 | 262.24 | 296.25 | 285.56 | 302.11 | 53 |

General techniques for toxicity testing include dermal irritation testing, eye irritation testing, subcutaneous test, intramuscular tests, open wound irrigation, intranasal tests, and oral tests. Dermal tests can be conducted on rabbits wherein 0.5 ml of 10% emulsion is applied to the skin or rabbits for four hours. The skin reaction is recorded for up to 72 hours. A Draize scale is used to score the irritation. For eye irritation testing, 0.1 ml of 10% emulsion is applied to the eye of rabbits and the eye reaction is recorded for up to 72 hours. A Draize scale is used to score the irritation. Subcutaneous and intramuscular tests inject 0.1 ml of 10% emulsion in mice. Two ml of 10% emulsion is applied in an open wound irrigation test using mice. For intranasal testing, 0.25 m/naris of 2-4% emulsion are applied to mice. For oral testing, 4 ml/kg/day of 10% emulsion are given orally for 1 week or 8 ml/kg of 100% emulsion is given in a single dose.

Example 9

In Vitro Study with *Bacillus Anthracis*

Figure 3:
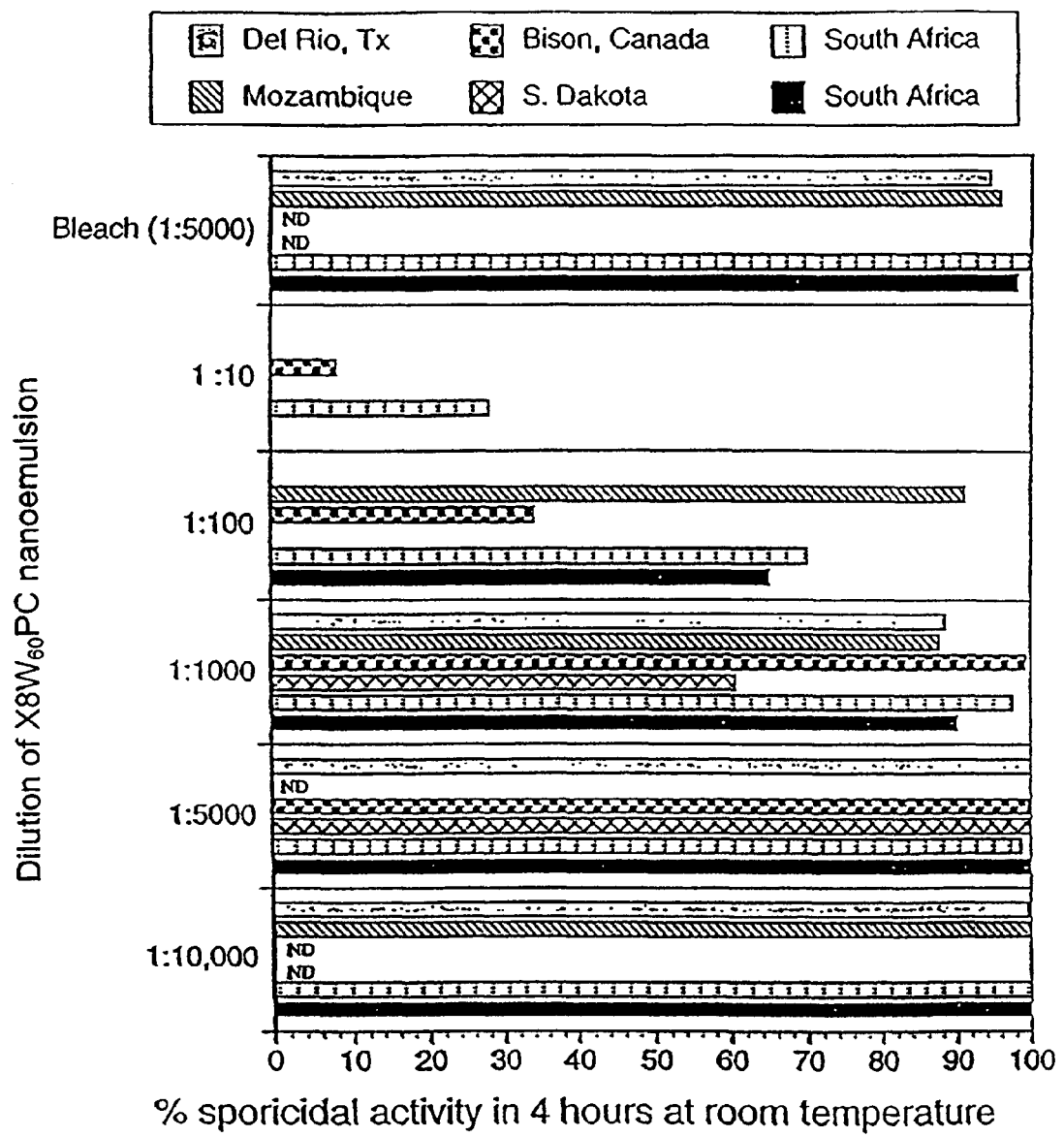
FIG. 3 illustrates the sporicidal activity of different dilutions of an emulsion of the present invention on different *B. anthracis* spores.
Figure 4:
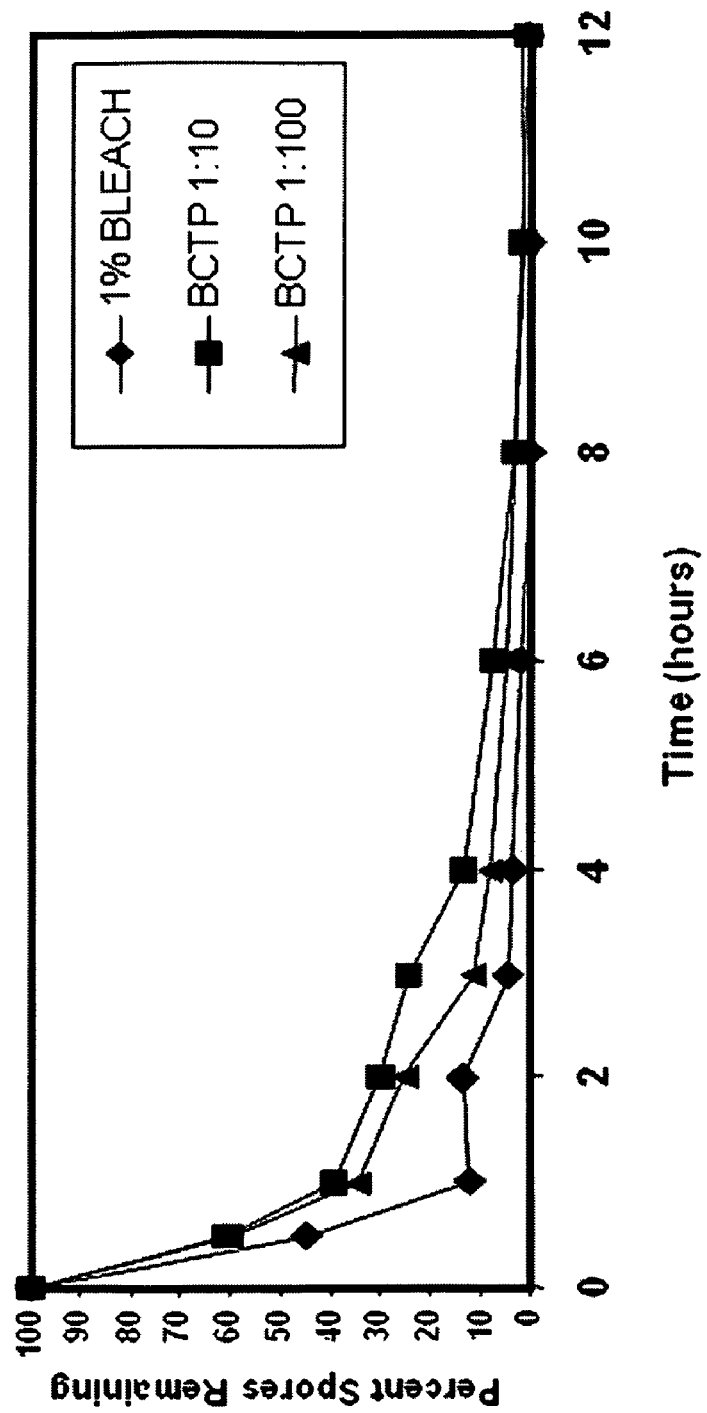
FIG. 4 illustrates a comparison of the sporicidal activity of an emulsion of the present invention and bleach over time.
Figure 5:
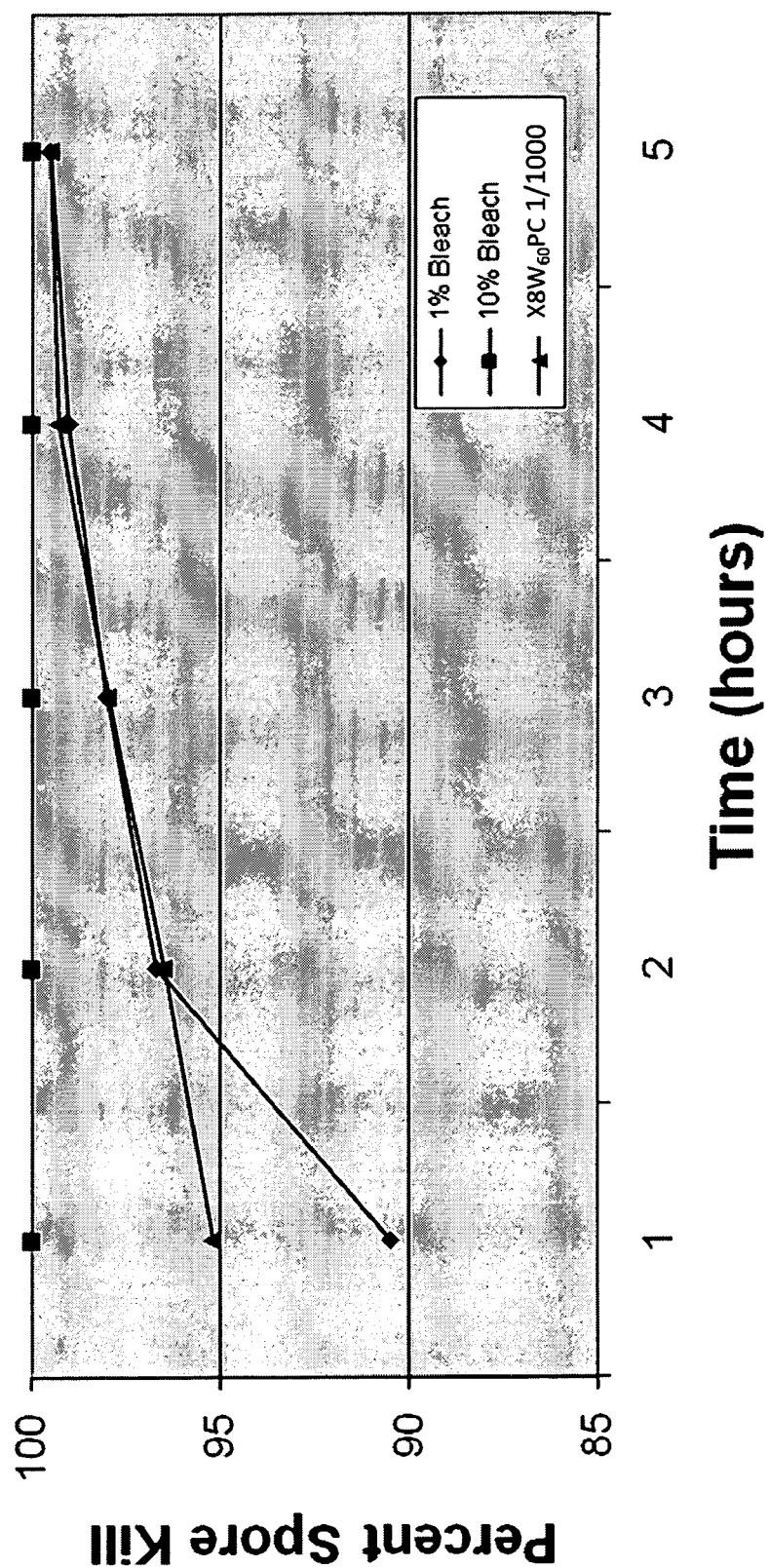
FIG. 5 illustrates a comparison of the sporicidal activity of an emulsion of the present invention and bleach over time.
Figure 6:
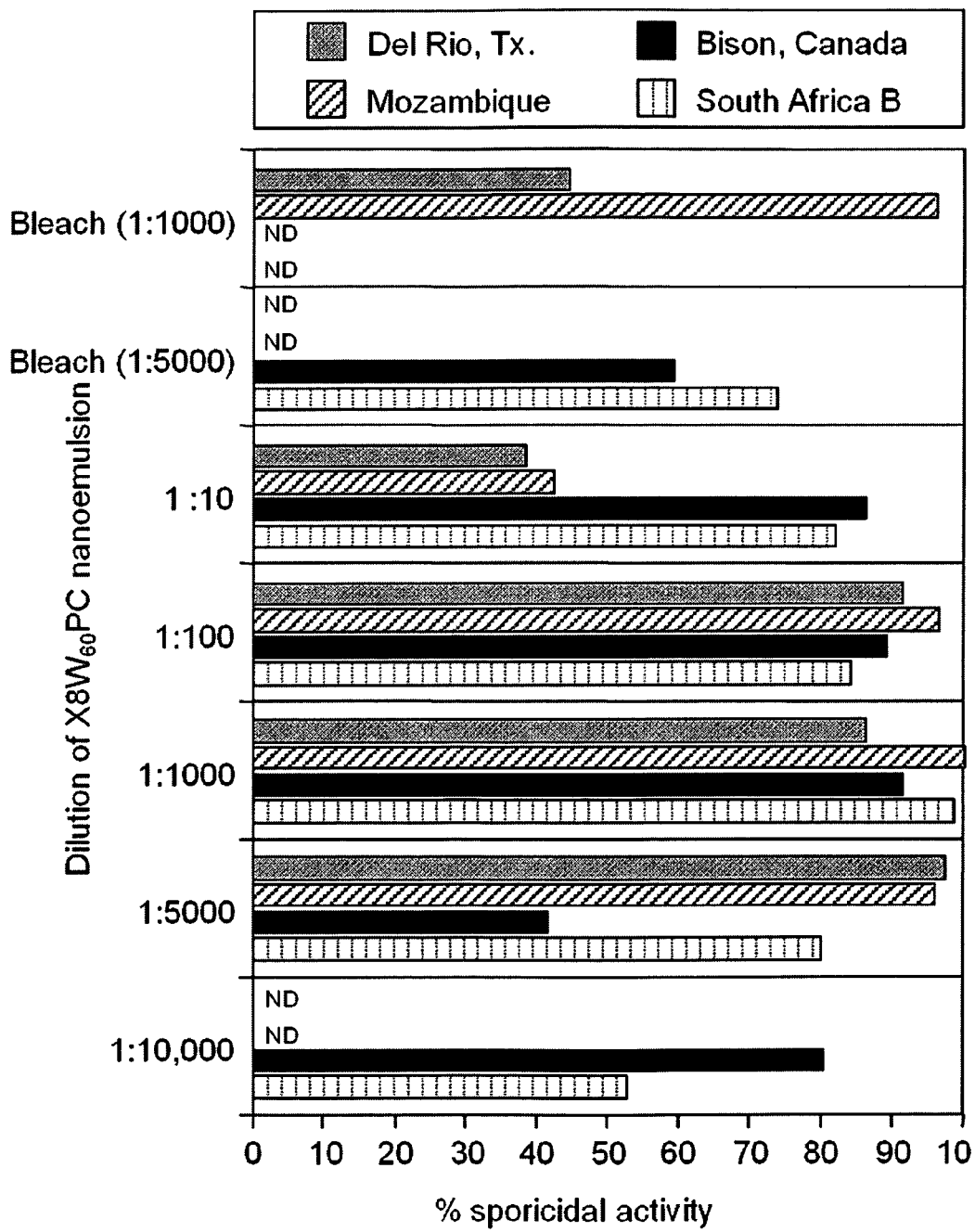
FIG. 6 illustrates the sporicidal activity of different dilutions of an emulsion of the present invention in media on different *B. anthracis* spores.
Figure 7:
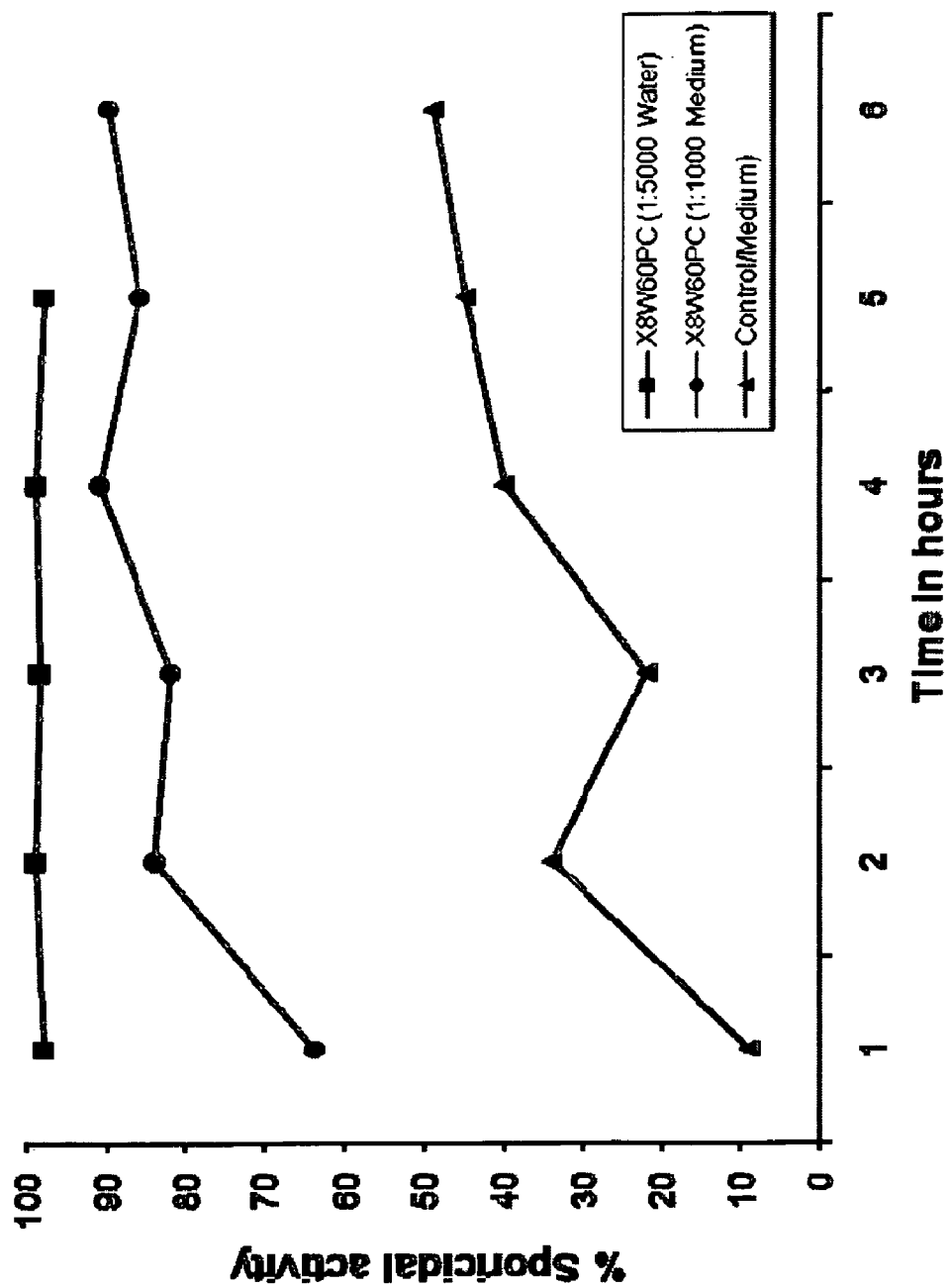
FIG. 7 illustrates the time course for the sporicidal activity of an emulsion of the present invention against *B. anthracis* from Del Rio, Tex.

Experiments with $X_8W_{60}PC$ preparations to study the bactericidal effect of the compounds of the present invention on the spore form of *B. anthracis* were performed. The sporicidal activity of different dilutions of $X_8W_{60}PC$ (in water) on six different strains of *B. anthracis* is shown in FIG. 3. As shown in FIGS. 4 and 5, $X_8W_{60}PC$ killed over 98% of seven different strains of anthrax (those of FIG. 3 and Ames, USAMRID) within 4 hours and is as efficient as 1-10% bleach. Similar sporicidal activity is found with different dilutions of $X_8W_{60}PC$ in media (FIG. 6). FIG. 7 shows the time course for the sporicidal activity of $X_8W_{60}PC$ against the Del Rio, Tex. strain of *B. anthracis* compared with zero time at room temperature. As shown, $X_8W_{60}PC$ can kill anthrax spores in as little as 30 minutes.

Example 10

Mechanisms of Action

Figure 8:
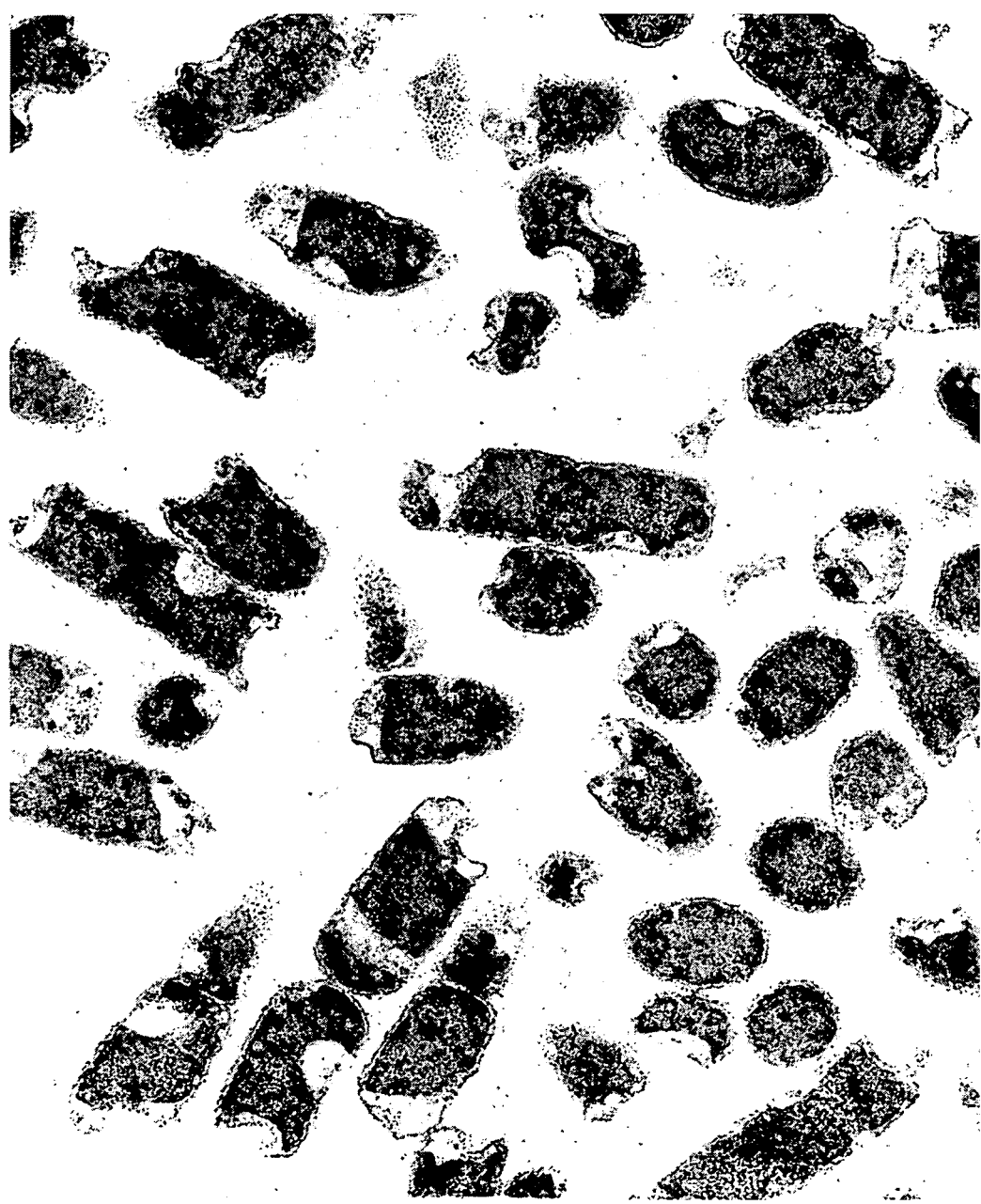
FIG. 8 depicts an electron micrograph of *E. coli* (10,000×).
Figure 9:
FIG. 9 depicts an electron micrograph of *E. coli* treated with BCTP (10,000×).
Figure 10:
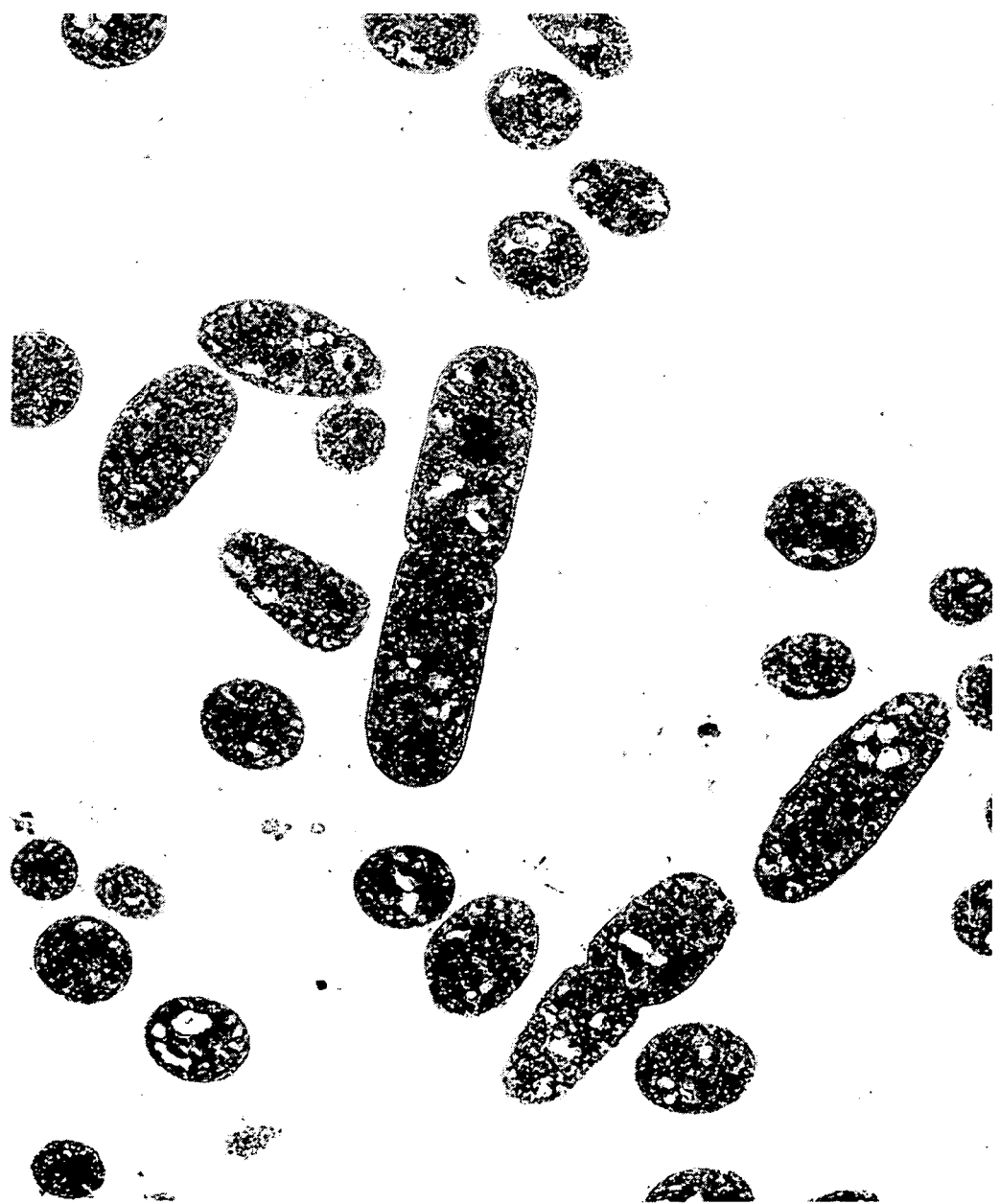
FIG. 10 depicts an electron micrograph of *E. coli* treated with $W_{80}8P$ (10,000×).
Figure 11:
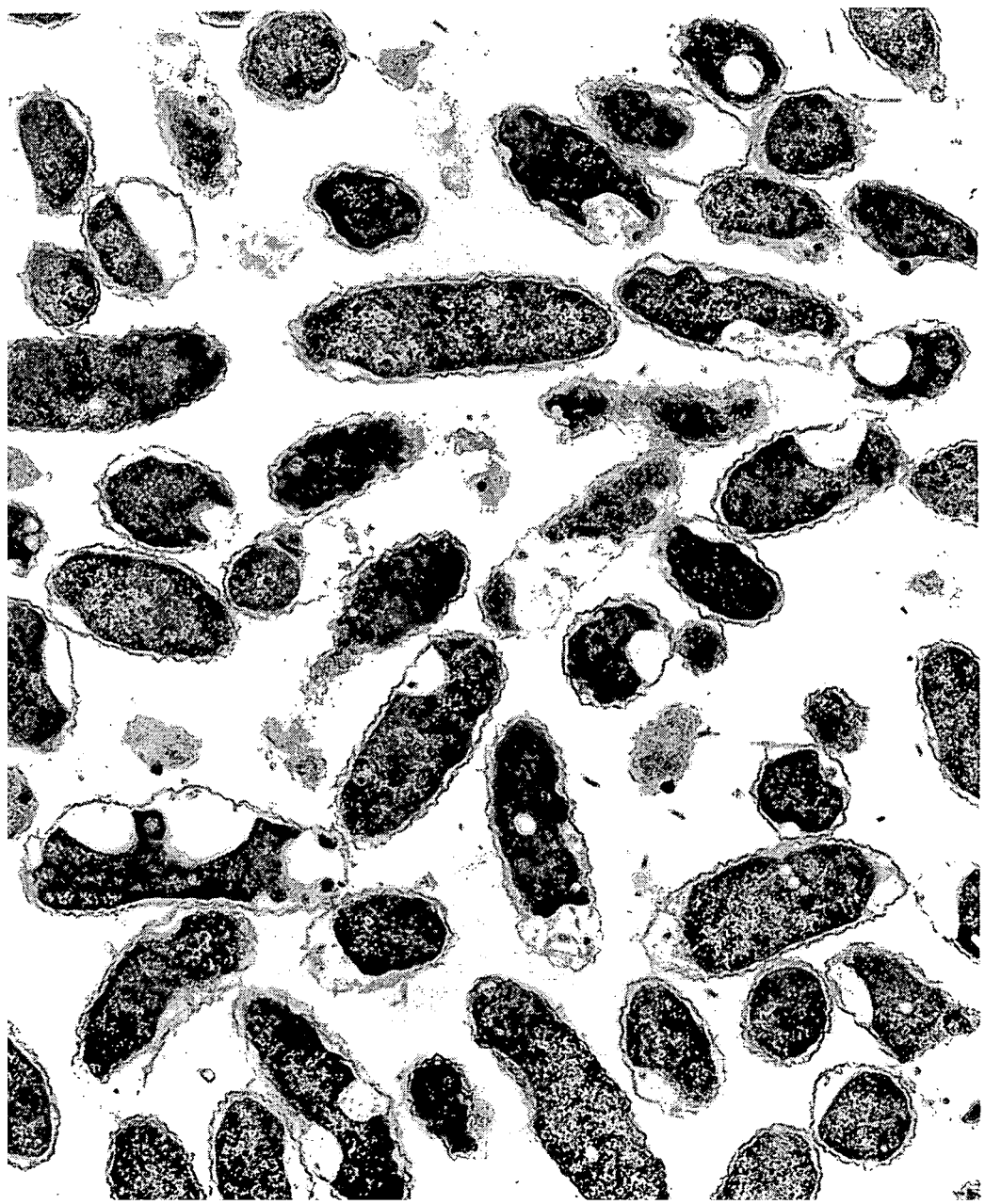
FIG. 11 depicts an electron micrograph of *Vibrio cholerae* (25,000×).
Figure 12:
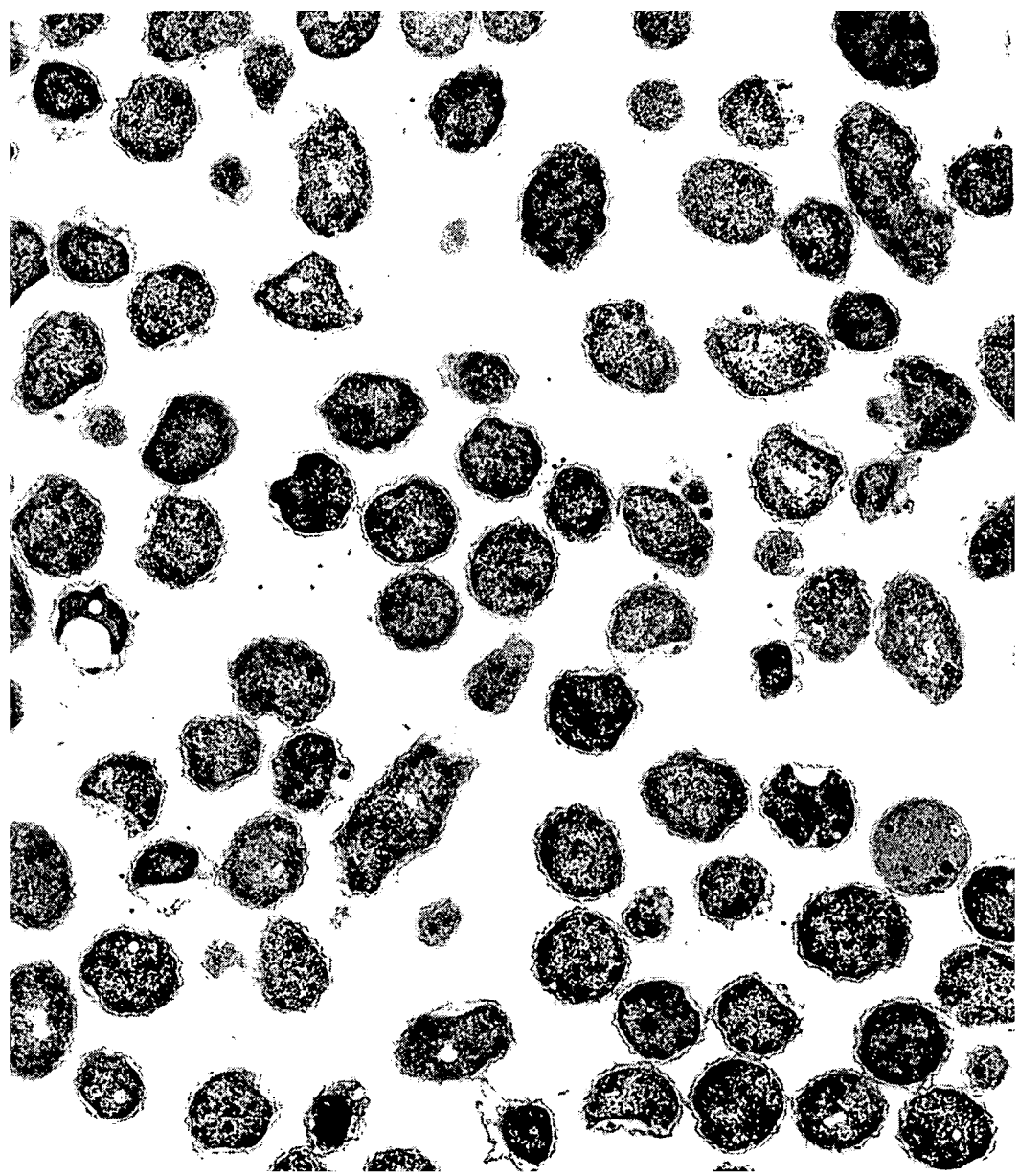
FIG. 12 depicts an electron micrograph of *Vibrio cholerae* treated with $W_{80}8P$ (25,000×).
Figure 13:
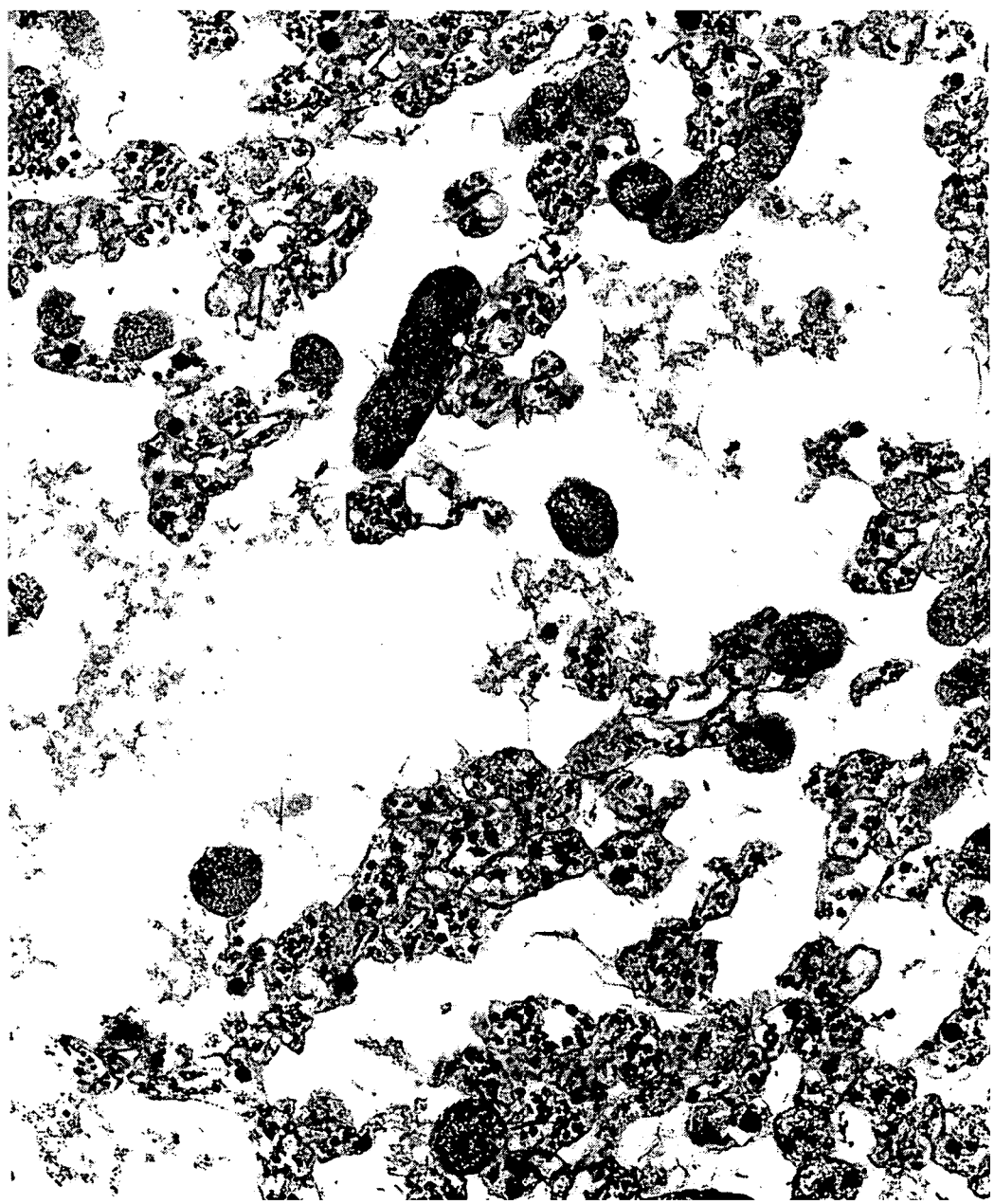
FIG. 13 depicts an electron micrograph of *Vibrio cholerae* treated with BCTP (25,000×).
Figure 14:
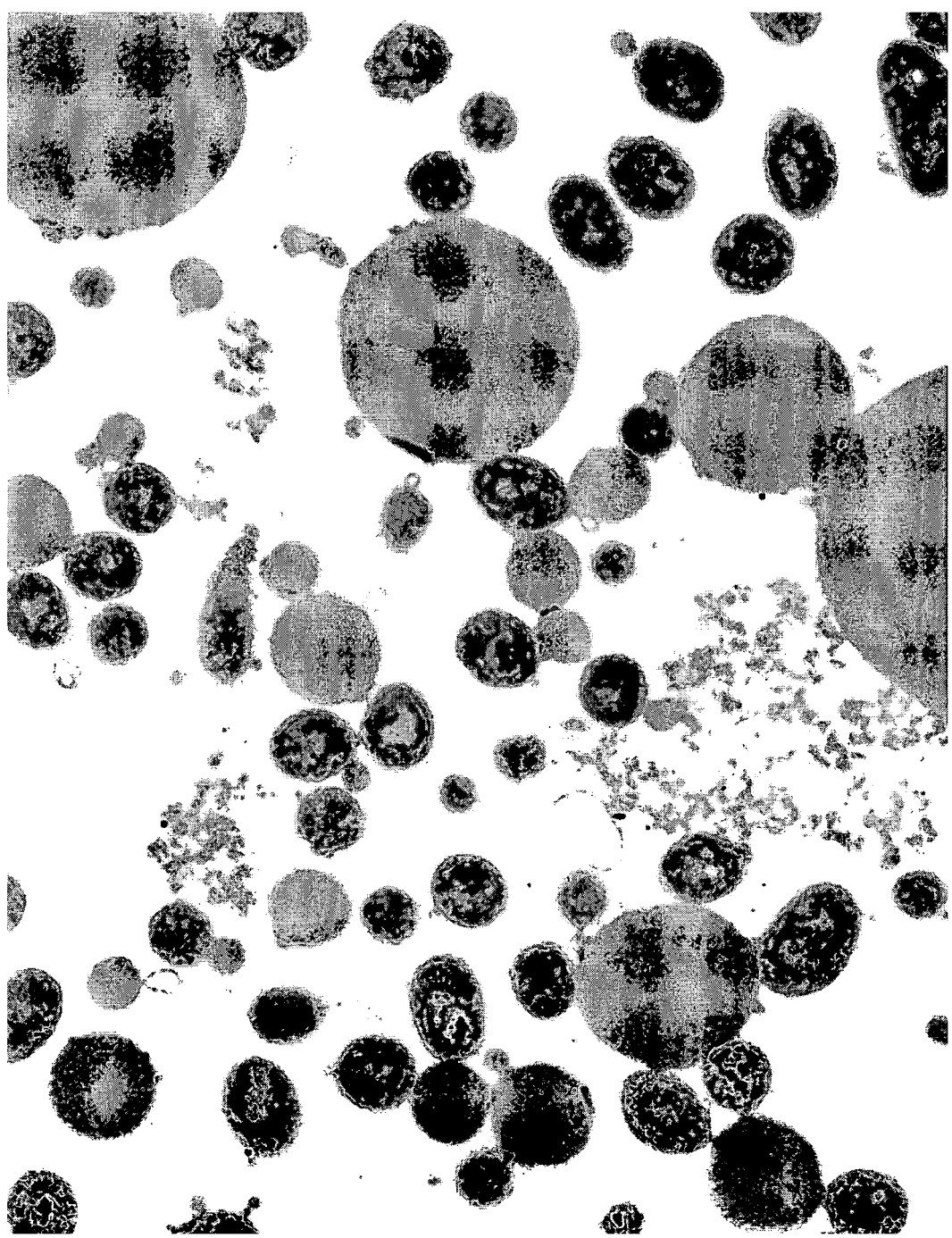
FIG. 14 depicts an electron micrograph of *Vibrio cholerae* treated with $X_8W_{60}PC$ (25,000×).

The following Example provides an insight into a proposed the mechanisms of action of the emulsions of the present invention and to show their sporicidal activity. This mechanism is not intended to limit the scope of the invention an understanding of the mechanism is not necessary to practice the present invention, and the present invention is not limited to any particular mechanism. The effect of a GMO/CPC lipid emulsion ("$W_{80}8P$") and BCTP on *E. coli* was examined. $W_{80}8P$ killed the *E. coli* (in deionized $H_2O$) but BCTP was ineffective against this organism. FIG. 8 shows the control and FIG. 9 shows the *E. coli* treated with BCTP. As shown in FIG. 9, the BCTP treated *E. coli* look normal, with defined structure and intact lipid membranes. FIG. 10 shows the P10 treated *E. coli*, wherein the bacteria have vacuoles inside and the contents have swollen so that the defined structure of the organism is lost. Without being bound to a particular theory (an understanding of the mechanism is not necessary to practice the present invention, and the present invention is not limited to any particular mechanism), this observation suggests that $W_{80}8P$ kills the bacteria without lysing them and instead causes a change in the internal structure, evident by the vacuolization and swelling. A second study was performed with *Vibrio cholerae*. Despite *Vibrio cholerae* being closely related to *E. coli*, both the BCTP, $W_{80}8P$ and $X_8W_{60}PC$ killed this organism. Compared to the control electromicrograph (FIG. 11), the $W_{80}8P$ treated *Vibrio cholerae* (FIG. 12) again shows swelling and changes in the interior of the organism, but the cells remain intact. In contrast, the BCTP treated *Vibrio cholerae* (FIG. 13) are completely lysed with only cellular debris remaining. $X_8W_{60}PC$ (FIG. 14) showed a combination of effects, where some of the organisms are swelled but intact and some are lysed. This clearly suggests that BCTP, $W_{80}8P$ and $X_8W_{60}PC$ work by different mechanisms.

Figure 15:
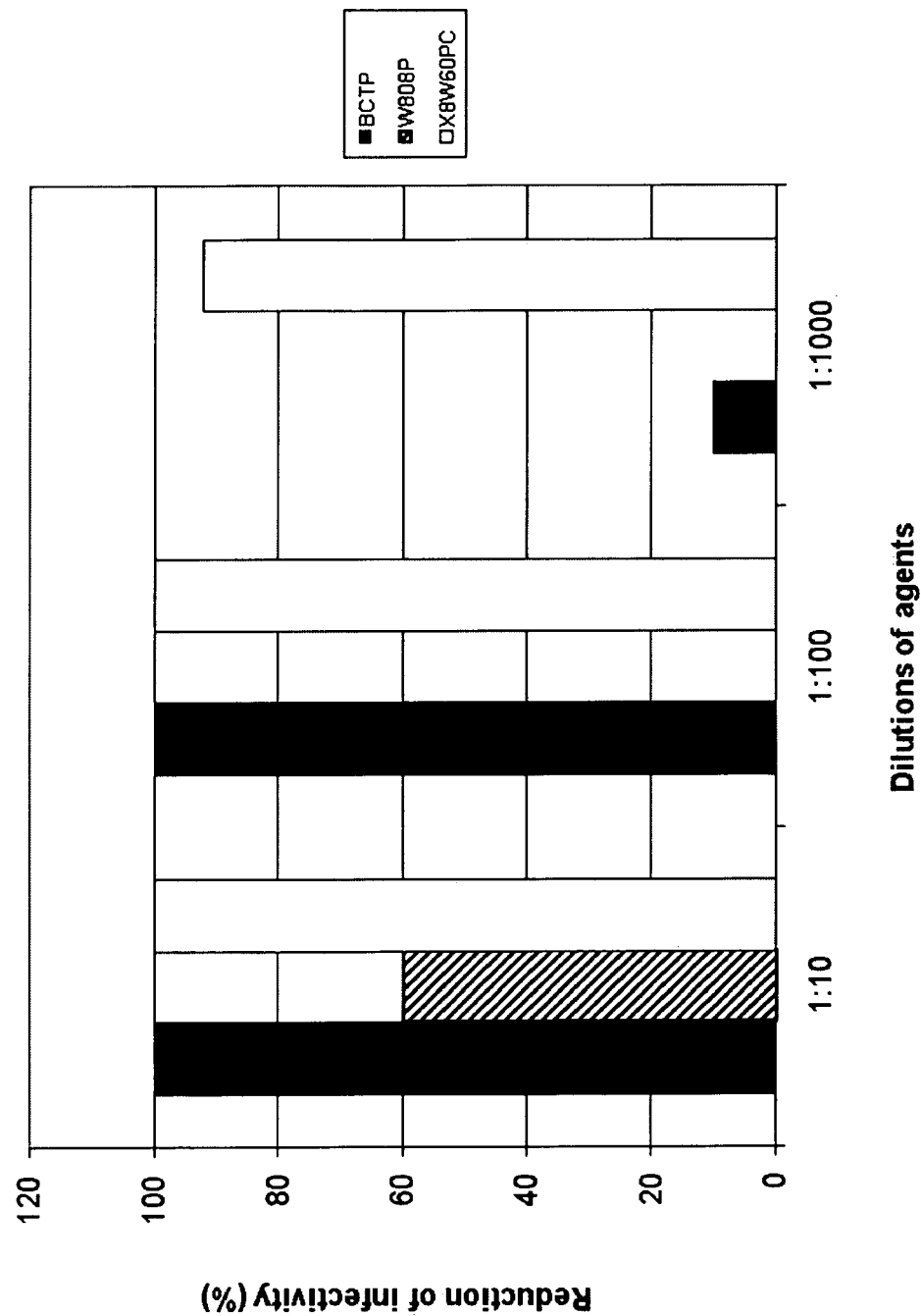
FIG. 15 illustrates the effect of BCTP, $W_{80}8P$ and $X_8W_{60}PC$ on influenza A activity.

A third comparative study was performed to evaluate efficacy of the emulsions at various concentrations. As shown in Table 18, $X_8W_{60}PC$ is more effective as a biocide at lower concentrations (higher dilutions) in bacteria sensitive to either $W_{80}8P$ or BCTP. In addition, six other bacteria that are resistant to $W_{80}8P$ and BCTP are all susceptible to $X_8W_{60}PC$. This difference in activity is also seen when comparing $W_{80}8P$ and BCTP and $X_8W_{60}PC$ in influenza infectivity assays. As shown in FIG. 15, both BCTP and $X_8W_{60}PC$ are effective at a 1:10 and 1:100 dilutions and additionally, $X_8W_{60}PC$ is effective at the lowest concentration, 1:1,000 dilution. In contrast, $W_{80}8P$ has little activity even at 1:10 dilution, suggesting that it is not an effective treatment for this enveloped organism. In addition, $X_8W_{60}PC$ kills yeast species that are not killed by either $W_{80}8P$ or BCTP.

TABLE 18

Lowest Nanoemulsion Concentration Required to Achieve Over 90% Killing of Selected Microorganisms

|  | $W_{80}8P$ | BCTP | $X_8W_{60}PC$ |
|---|---|---|---|
| Bacteria | | | |
| *Streptococcus pyogenes* | No killing | 10% | 0.1% |
| *Streptococcus aglactiae* | 1%* | 1% | ND |
| *Streptococcus pneumonia* | 10%* | 1% | 0.1% |
| *Staphylococcus aureus* | No killing | No killing | 0.1% |
| *Neissetia gonorhoeae* | ND | 1% | 0.1% |
| *Haemophilus influenzae* | 10% | 1% | 0.1% |
| *Vibrio cholerae* | 1% | 0.1% | 0.1% |
| *E. coli* | No killing# | No killing | 0.1% |
| *Salmonella typhimurium* | No killing# | No killing | 10% |
| *Shigella dysenteriae* | No killing# | No killing | 0.1% |
| *Proteus mirabilis* | No killing# | No killing | 1% |
| *Pseudomonas aeruginosa* | No killing | No killing | 10% |
| *Bacillus anthracis* spores | No killing @ 4 H | 0.1% @ 4 H | 0.1%-0.02% @ 4 H |
| *Bacillus cereus* spores | 10% @ 4 H | 1% @ 4 H | 0.1% @ 4 H |
| *Bacillus subtilus* spores | No killing @ 24 H | No killing @ 24 H | 0.1% @ 4 H |
| *Yersinia enterocolitica* | ND | ND | 0.1% |
| *Yersinia pseudotuberculosis* | ND | ND | 0.1% |
| Fungi | | | |
| *Candida albicans* (ATCC 90028) | No Killing | No Killing | 1% |
| *Candida tropicalis* | No Killing | No Killing | 1% |
| Viruses | | | |
| Influenza A H2N2 | No Killing | 1% | 0.1% |
| Influenza B/Hong Kong/5/72 | ND | 1% | ND |
| Vaccinia | ND | 1% | % |
| Herpes simplex type I | ND | 1% | 0.1% |
| Sendai | ND | 1% | ND |
| Sindbis | ND | 1% | ND |
| Adenovirus | ND | No Killing | ND |

*Data for lower concentrations not available.
No killing except in deionized water.
10 ND = Not determined.

Example 11

Further Evidence of the Sporicidal Activity of the Nanoemulsion Against *Bacillus* Species The present Example provides the results of additional investigations of the ability of particular embodiments of the emulsions of the present invention to inactivate different *Bacillus* spores. The methods and results from these studies are outlined below.

Surfactant lipid preparations: BCTP, a water-in-oil nanoemulsion, in which the oil phase was made from soybean oil, tri-n-butyl phosphate, and TRITON X-100 in 80% water. $X_8W_{60}PC$ was prepared by mixing equal volumes of BCTP with $W_{80}8P$ which is a liposome-like compound made of glycerol monostearate, refined Soya sterols, TWEEN 60, soybean oil, a cationic ion halogen-containing CPC and peppermint oil.

Spore preparation: For induction of spore formation, *Bacillus cereus* (ATTC 14579), *B. circulans* (ATC 4513), *B. megaterium* (ATCC 14581), and *B. subtilis* (ATCC 11774) were grown for a week at 37° C. on NAYEMn agar (Nutrient Agar with 0.1% Yeast Extract and 5 mg/l $MnSO_4$). The plates were scraped and the bacteria/spores suspended in sterile 50% ethanol and incubated at room temperature (27° C.) for 2 hours with agitation in order to lyse the remaining vegetative bacteria. The suspension was centrifuged at 2,500×g for 20 minutes and the pellet washed twice in cold $diH_2O$. The spore pellet was resuspended in trypticase soy broth (TSB) and used immediately for experiments. *B. anthracis* spores, Ames and Vollum 1 B strains, were kindly supplied by Dr. Bruce Ivins (USAMRIID, Fort Detrick, Frederick, Md.), and prepared as previously described (Ivins et al., 1995). Four other strains of anthrax were kindly provided by Dr. Martin Hugh-Jones (LSU, Baton Rouge, La.). These strains represent isolates with high allelic dissimilarity from South Africa; Mozambique; Bison, Canada; and Del Rio, Tex.

In vitro sporicidal assays: For assessment of sporicidal activity of solid medium, trypticase Soy Agar (TSA) was autoclaved and cooled to 55° C. The BCTP was added to the TSA at a 1:100 final dilution and continuously stirred while the plates were poured. The spore preparations were serially diluted (ten-fold) and 10 μl aliquots were plated in duplicate (highest inoculum was $10^5$ spores per plate). Plates were incubated for 48 hours aerobically at 37° C. and evaluated for growth.

For assessment of sporicidal activity in liquid medium, spores were resuspended in TSB. 1 ml of spore suspension containing $2×10^6$ spores (final concentration $10^6$ spores/ml) was mixed with 1 ml of BCTP or $X_8W_{60}PC$ (at 2× final concentration in diH$_2$O) in a test tube. The tubes were incubated in a tube rotator at 37° C. for four hours. After treatment, the suspensions were diluted 10-fold in diH$_2$O. Duplicate aliquots (25 µl) from each dilution were streaked on TSA, incubated overnight at 37° C., and then colonies were counted. Sporicidal activity expressed as a percentage killing was calculated:

$$\frac{cfu[\text{initial}] - cfu[\text{post-treatment}]}{cfu[\text{initial}]} \times 100.$$

The experiments were repeated at least 3 times and the mean of the percentage killing was calculated.

Electron microscopy: B. cereus spores were treated with BCTP at a 1:100 final dilution in TSB using Erlenmeyer flasks in a 37° C. shaker incubator. Fifty ml samples were taken at intervals and centrifuged at 2,500×g for 20 minutes and the supernatant discarded. The pellet was fixed in 4% glutaraldehyde in 0.1 M cacodylate (pH 7.3). Spore pellets were processed for transmission electron microscopy and thin sections examined after staining with uranyl acetate and lead citrate.

Germination inhibitors/simulators: B. cereus spores (at a final concentration 10$^6$ spores/ml) were suspended in TSB with either the germination inhibitor D-alanine (at final concentration of 1 µM) or with the germination stimulator L-alanine+inosine (at final concentration of 50 µM each) (Titball and Manchee, 1987; Foster and Johnston., 1990; Shibata et al., 1976) and then immediately mixed with BCTP (at a final dilution of 1:100) and incubated for variable interval. Then the mixtures were serially diluted, plated and incubated overnight. The next day the plates were counted and percentage sporicidal activity was calculated.

In vivo sporicidal activity: Two animal models were developed; in the first B. cereus spores (suspended in sterile saline) were mixed with an equal volume of BCTP at a final dilution of 1:10. As a control, the same B. cereus spore suspension was mixed with an equal volume of sterile saline. 100 µl of the suspensions containing 4×10$^7$ spores was then immediately injected subcutaneously into CD-1 mice.

In the second model, a simulated wound was created by making an incision in the skin of the back of the mice. The skin was separated from the underlying muscle by blunt dissection. The "pocket" was inoculated with 200 µl containing 2.5×10$^7$ spores (in saline) and closed using wound clips. One hour later, the clips were removed and the wound irrigated with either 2 ml of sterile saline or with 2 ml of BCTP (1:10 in sterile saline). The wounds were then closed using wound clips. The animals were observed for clinical signs. Gross and histopathology were performed when the animals were euthanized 5 days later. The wound size was calculated by the following formula: ½a×½b×π where a and b are two perpendicular diameters of the wound.

Figure 16:
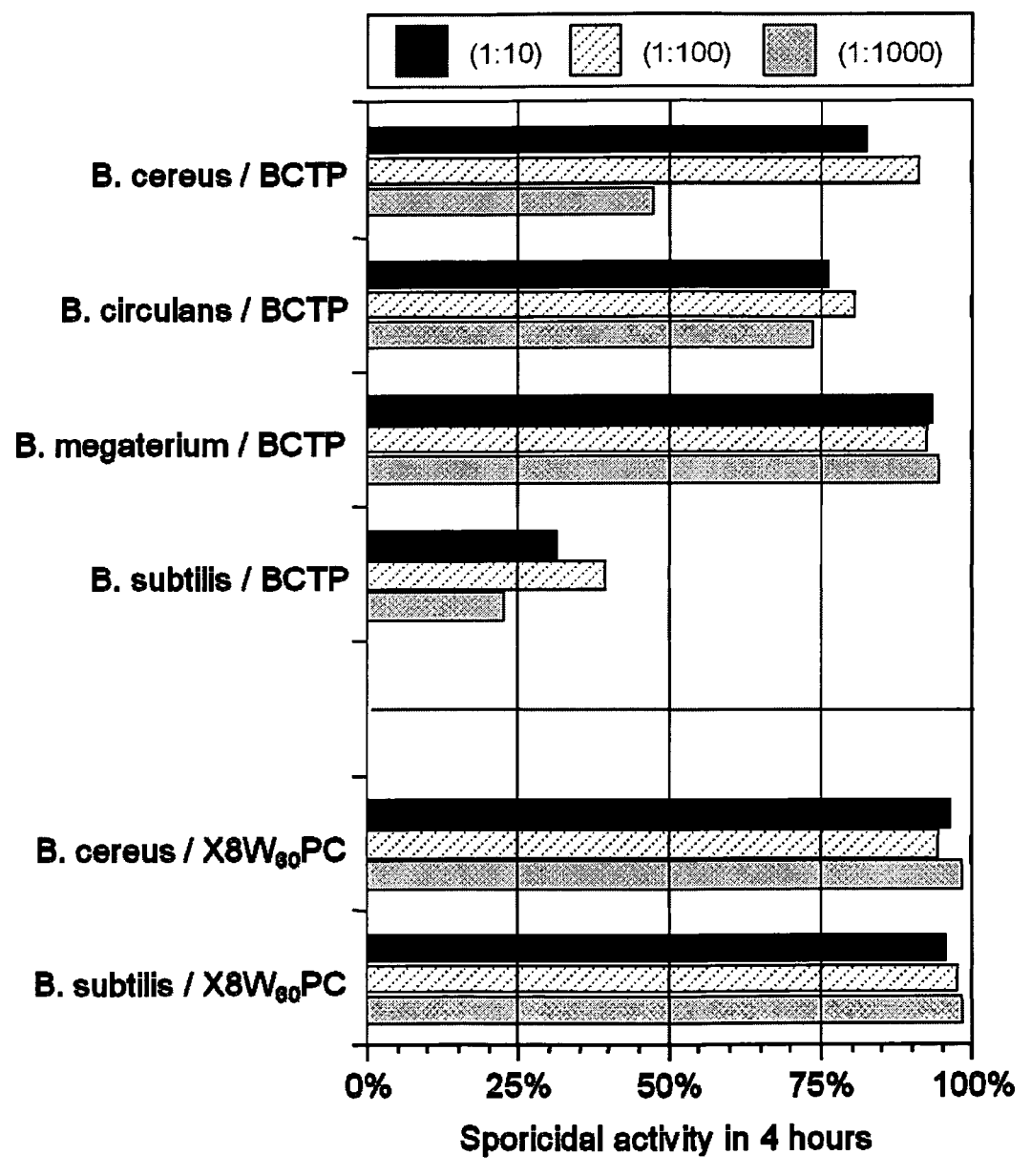

In vitro sporicidal activity: To assess the sporicidal activity of BCTP, spores from four species of Bacillus genus, B. cereus, B. circulans, B. megatetium, and B. subtilis were tested. BCTP at 1:100 dilution showed over 91% sporicidal activity against B. cereus and B. megaterium in 4 hours (FIG. 16). B. circulans was less sensitive to BCTP showing 80% reduction in spore count, while B. subtilis appeared resistant to BCTP in 4 hours. A comparison of the sporicidal effect of BCTP (at dilutions of 1:10 and 1:100) on B. cereus spores was made with a 1:100 dilution of bleach (i.e., 0.0525% sodium hypochlorite), and no significant difference was apparent in either the rate or extent of sporicidal effect. The other nanoemulsion, $X_8W_{60}PC$, was more efficient in killing the Bacillus spores. At 1:1000 dilution, it showed 98% killing of B. cereus spores in 4 hours (compared to 47% with 1:1000 dilution of BCTP). $X_8W_{60}PC$ at 1:1000 dilution resulted in 97.6% killing of B. subtilis spores in 4 hours, in contrast to its resistance to BCTP.

Figure 17:
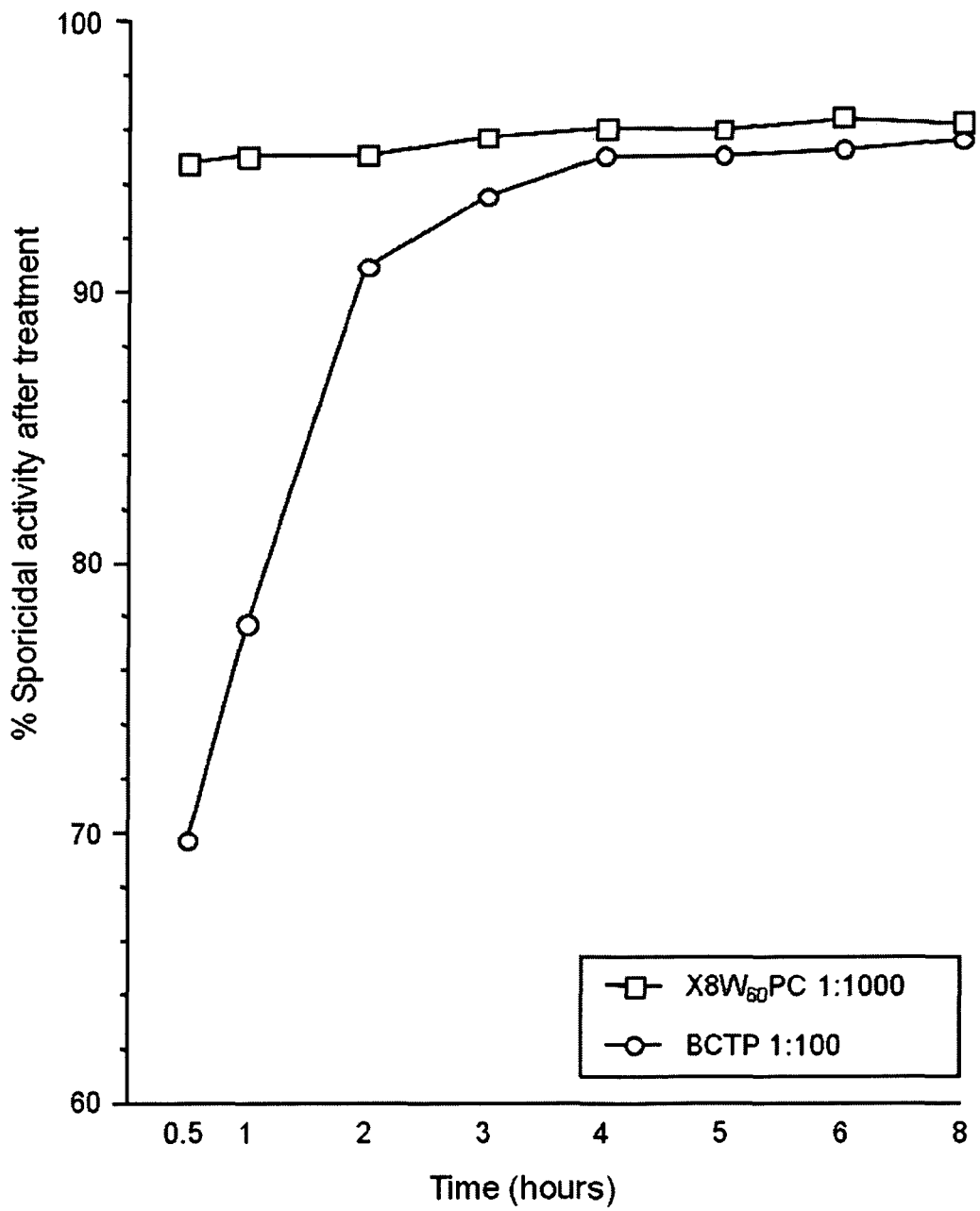
FIG. 17 illustrates the time course of the nanoemulsion sporicidal activity against *Bacillus cereus*. Incubation with BCTP diluted 1:100 resulted in 95% killing in 4 hours. Incubation with $X_8W_{60}PC$ diluted 1:1000 resulted in 95% killing in only 30 minutes.

B. cereus sporicidal time course: A time course was performed to analyze the sporicidal activity of BCTP diluted 1:100 and $X_8W_{60}PC$ diluted 1:1000 against B. cereus over an eight hour period. Incubation of BCTP diluted 1:100 with B. cereus spores resulted in a 77% reduction in the number of viable spores in one hour and a 95% reduction after 4 hours. Again, $X_8W_{60}PC$ diluted 1:1000 was more effective than BCTP 1:100 and resulted in about 95% reduction in count after 30 minutes (FIG. 17).

BCTP B. anthracis sporicidal activity: Following initial in vitro experiments, BCTP sporicidal activity was tested against two virulent strains of B. anthracis (Ames and Vollum 1B). It was found that BCTP at a 1:100 final dilution incorporated into growth medium completely inhibited the growth of 1×10$^5$ B. anthracis spores. Also, 4 hours incubation with BCTP at dilutions up to 1:1000 with either the Ames or the Vollum 1 B spores resulted in over 91% sporicidal activity when the mixtures were incubated at RT, and over 96% sporicidal activity when the mixtures were incubated at 37° C. (Table 19).

TABLE 19

BCTP sporicidal activity against 2 different strains of Bacillus anthracis spores as determined by colony reduction assay (% killing). BCTP at dilutions up to 1:1000 effectively killed >91% of both spore strains in 4 hours at either 27 or 37° C.; conditions that differed markedly in the extent of spores germination. Sporicidal activity was consistent at spore concentrations up to 1 × 10$^6$/ml.

| B. anthracis | Ames Room Temp. | Ames (cont) 37° C. | Vollum 1 B Room Temp. | Vollum 1 B 37° C. |
|---|---|---|---|---|
| BCTP 1:10 | 91% | 96% | 97% | 99% |
| BCTP 1:100 | 93% | 97% | 97% | 98% |
| BCTP 1:1000 | 93% | 97% | 98% | 99% |

$X_8W_{60}PC$ B. anthracis sporicidal activity: Since $X_8W_{60}PC$ was effective at higher dilutions and against more species of Bacillus spores than BCTP, it was tested against 4 different strains of B. anthracis at dilutions up to 1:10,000 at RT to prevent germination. $X_8W_{60}PC$ showed peak killing between 86% and 99.9% at 1:1000 dilution (Table 20).

TABLE 20

$X_8W_{60}PC$ sporicidal activity against 4 different strains of B. anthracis representing different clinical isolates. The spores were treated with $X_8W_{60}PC$ at different dilutions in RT to reduce germination. There as no significant killing at low dilutions. The maximum sporicidal effect was observed at 1:1000 dilution.

| B. Anthracis | South Africa | Bison, Canada | Mozambigue | Del Rio, Texas |
|---|---|---|---|---|
| $X_8W_{60}PC$ 1:10 | 81.8 | 85.9 | 41.9 | 38 |
| $X_8W_{60}PC$ 1:100 | 84 | 88.9 | 96.5 | 91.3 |
| $X_8W_{60}PC$ 1:1000 | 98.4 | 91.1 | 99.9 | 86 |
| $X_8W_{60}PC$ 1:5,000 | 79.7 | 41.3 | 95.7 | 97.1 |
| $X_8W_{60}PC$ 1:10,000 | 52.4 | 80 | ND | ND |

Electron microscopy examination of the spores: Investigations were carried out using B. cereus because it is the most closely related to B. anthracis. Transmission electron microscopy examination of the *B. cereus* spores treated with BCTP diluted 1:100 in TSB for four hours revealed physical damage to the *B. cereus* spores, including extensive disruption of the spore coat and cortex with distortion and loss of density in the core (FIG. 18).

Figure 19:
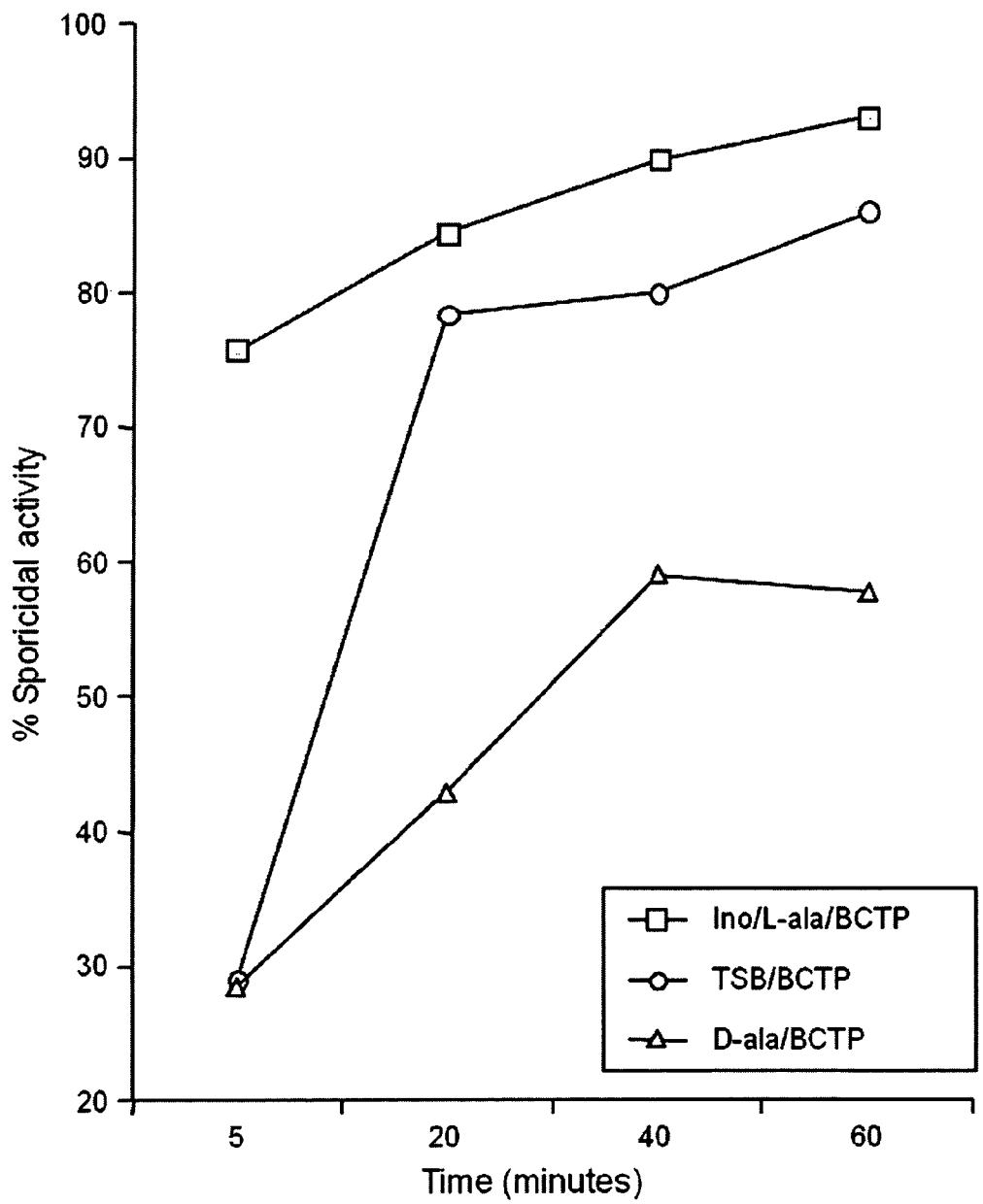
FIG. 19 illustrates the effects of germination inhibition and stimulation on the sporicidal activity of BCTP diluted 1:100. BCTP sporicidal activity was delayed in the presence of 10 mM D-alanine (germination inhibition), and accelerated in the presence of 50 μM L-alanine and 50 μM Inosine (germination stimulation).

Germination stimulation and inhibition: To investigate the effect of initiation of germination on the sporicidal effect of BCTP on *Bacillus* spores, the germination inhibitors D-alanine (Titball and Manchee, 1987; Foster and Johnston, 1990), and germination simulators L-alanine and inosine (Shibata et al., 1976) were incubated with the spores and BCTP for 1 hour. The sporicidal effect of BCTP was delayed in the presence of 10 mM D-alanine and accelerated in the presence of 50 µM L-alanine and 50 µM inosine (FIG. 19).

In vivo sporicidal activity: *Bacillus cereus* infection in experimental animals had been previously used as a model system for the study of anthrax and causes an illness similar to experimental anthrax infection (Welkos et al., 1986; Drobniewski, 1993; Burdon and Wende, 1960; Burdon et al., 1967; Fritz et al. 1995 et al., 1995; Welkos and Friedlander, 1988). Two animal models of cutaneous *B. cereus* disease were developed to assess the in vivo efficacy of BCTP. Because these models involve subcutaneous administration of the nanoemulsion, in vivo toxicity testing of BCTP was performed prior to this application. CD-1 mice injected with BCTP diluted 1:10 in saline as a control did not exhibit signs of distress or inflammatory reaction, either in gross or histological analysis (FIG. 20A, FIG. 20B). To test the pathogenic effect of *B. cereus* spores in vivo and the sporicidal effect of BCTP, a suspension of $4 \times 10^7$ *B. cereus* spores was mixed with saline or with BCTP at a final dilution of 1:10 and then immediately injected subcutaneously into the back of CD-1 mice. Mice which were infected subcutaneously with *B. cereus* spores without BCTP developed severe edema at 6-8 hours. This was followed by a gray, necrotic area surrounding the injection site at 18-24 hours, with severe sloughing of the skin present by 48 hours, leaving a dry, red-colored lesion (FIG. 20C, FIG. 20D). Simultaneous injection of spores and BCTP resulted in a greater than 98% reduction in the size of the necrotic lesion from 1.68 cm$^2$ to 0.02 cm$^2$ when the spores were premixed with BCTP. This was associated with minimal edema or inflammation (FIG. 20E, FIG. 20F).

In additional studies, a 1 cm skin wound was infected with $2.5 \times 10^7$ *B. cereus* spores then closed without any further treatment (FIG. 21A, FIG. 21B). The other groups were infected with the same number of spores, then 1 hour later the wounds were irrigated with either BCTP or saline to simulate post-exposure decontamination. Irrigation of experimentally infected wounds with saline did not result in any apparent benefit (FIG. 21C, FIG. 21D). BCTP irrigation of wounds infected with *B. cereus* spores showed substantial benefit, resulting in a consistent 98% reduction in the lesion size from 4.86 cm$^2$ to 0.06 cm$^2$ (FIG. 21E, FIG. 21F). This reduction in lesion size was accompanied by a four-fold reduction in mortality (80% to 20%) when compared to experimental animals receiving either no treatment or saline irrigation.

Example 12

Effect of Surfactant Lipid Preparations (SLPS) on Influenza a Virus Infectivity In Vitro Enveloped viruses are of great concern as pathogens. They spread rapidly and are capable of surviving out of a host for extended periods. Influenza A virus was chosen because it is a well accepted model to test anti-viral agents (Karaivanova and Spiro, 1998; Mammen et al, 1995; Huang et al, 1991). Influenza is a clinically important respiratory pathogen that is highly contagious and responsible for severe pandemic disease (Mulder and Hers, 1972).

The envelope glycoproteins, hemagglutinin (HA) and neuraminidase (NA) not only determine the antigenic specificity of influenza subtypes (Schulze, 1997), but they mutate readily and, as a result, may allow the virus to evade host defense systems. This may result in the initiation of disease in individuals that are immune to closely related strains. The following is a description of the methods and composition used for determining the efficacy of SLPs in preventing influenza A infectivity.

Surfactant lipid preparations (SLPs): The SLPs were made in a two-step procedure. An oil phase was prepared by blending soybean oil with reagents listed in Table 1 and heating at 86° C. for one hour (Florence, 1993). The SLPs were then formed by injecting water or 1% bismuth in water (SS) into the oil phase at a volume/volume ratio using a reciprocating syringe pump.

Viruses: Influenza virus A/AA/6/60 (Hedocher et al., 1996) was kindly provided by Dr. Hunein F. Maassab (School of Public Health, University of Michigan). Influenza A virus was propagated in the allantoic cavities of fertilized pathogen-free hen eggs (SPAFAS, Norwich, Conn.) using standard methods (Barrett and Inglis, 1985). Virus stock was kept in aliquots ($10^8$ pfu/ml) of infectious allantoic fluids at −80° C. Adenoviral vector (AD.RSV ntlacZ) was provided by Vector Core Facility (University of Michigan Medical Center, Ann Arbor, Mich.) and was kept in aliquots ($10^{12}$ pfu/ml at −80° C.). The vector is based on a human adenoviral (serotype 5) genomic backbone deleted of the nucleotide sequence spanning E1A and E1B and a portion of E3 region. This impairs the ability of the virus to replicate or transform nonpermissive cells. It carries the *Eschetichia coli* LacZ gene, encoding, β-galactosidase, under control of the promoter from the Rouse sarcoma virus long terminal repeat (RSV-LTR). It contains a nuclear targeting (designated as nt) epitope linked to the 5' end of the LacZ gene to facilitate the detection of protein expression (Baragi et al., 1995).

Cells: Madin Darby Canine Kidney (MDCK) cells were purchased from the American Type Culture Collection (ATCC; Rockville, Md.) and 293 cells (CRL 1573; transformed primary embryonic human kidney) were obtained from the Vector Core Facility (University of Michigan Medical Center, Ann Arbor, Mich.). The 293 cells express the transforming gene of adenovirus 5 and therefore restore the ability of Ad.RSV ntlacZ vector to replicate in the host cell (Graham et al., 1977).

Cell maintenance media: MDCK cells were maintained in Eagle's minimal essential medium with Earle's salts, 2 mM L-glutamine, and 1.5 g/l sodium bicarbonate (Mediatech, Inc., Herndon, Va.) containing 10% fetal bovine serum (FBS; Hyclone Laboratories, Logan, Utah). The medium was supplemented with 0.1 mM non-essential amino acids, 1.0 mM sodium pyruvate, 100 U penicillin/ml and streptomycin 100 µg/ml (Life Technologies, Gaithersburg, Md.). The 293 cells were maintained in Dulbecco's modified Eagle medium (Mediatech, Inc., Herndon, Va.), containing 2 mM L-glutamine, 0.1 mM non-essential amino acids, and 1.0 mM sodium pyruvate. It also contained 100 U penicillin/ml and streptomycin 100 µg/ml (Life Technologies, Gaithersburg, Md.) and was supplemented with 10% FBS (Hyclone Laboratories, Logan, Utah).

Virus infection media: Influenza A infection medium was the MDCK cell maintenance medium (without FBS) supplemented with 3.0 µg/ml of tolylsulfonyl phenylalanyl chloromethyl ketone (TPCK)-treated trypsin (Worthington Biochemical Corporation, Lakewood, N.J.). Adenovirus infection medium was 293) cell maintenance medium with a reduced concentration of serum (2% FBS).

Influenza A overlay medium: Overlay medium consisted of equal amounts of 2× infection medium and 1.6% SEAKEM ME agarose (FMC BioProducts, Rockland, Md.). Staining agarose overlay medium consisted of agarose overlay medium plus 0.01% neutral red solution (Life Technologies, Gaithersburg, Md.) without TPCK-treated trypsin.

Plaque reduction assays (PRA): The plaque reduction assay was performed with a modification of the method described elsewhere (Hayden et al., 1980). MDCK cells were seeded at $1\times10^5$ cells/well in 12-well FALCON plates and incubated at 37° C./5% $CO_2$ for 3 days. Approximately $1\times10^8$ pfu of influenza A virus was incubated with surfactant lipid preparations as described below. The influenza A virus-SLP treatments and controls were diluted in infection medium to contain 30-100 pfu/250 µl. Confluent cell monolayers were inoculated in triplicate on 3 plates and incubated at 37° C./5% $CO_2$ for 1 h. The inoculum/medium was aspirated and 1 ml of agarose overlay medium/well was added and plates were incubated at 37° C./5% $CO_2$ until plaques appeared. Monolayers were stained with the agarose overlay medium and incubation was continued at 37° C./5% $CO_2$. Plaques were counted 6-12 h after staining. The average plaque count from 9 wells with lipid preparation concentration was compared with the average plaque count of untreated virus wells.

In situ cellular enzyme-linked immunosorbent assay (ELISA): To detect and quantitate viral proteins in MDCK cells infected with influenza A virus, the in situ cellular ELISA was optimized. Briefly, $2\times10^4$ MDCK cells in 100 µl complete medium were added to flat-bottom 96-well microtitre plates and incubated overnight. On the next day, the culture medium was removed and cells were washed with serum free maintenance medium. One hundred µl of viral inoculum was added to the wells and incubated for 1 hour. The viral inoculum was removed and replaced with 100 µl of MDCK cell maintained medium plus 2% FBS. The infected MDCK cells were incubated for an additional 24 h. Then the cells were washed once with PBS and fixed with ice cold ethanol: acetone mixture (1:1) and stored at −20° C. On the day of the assay, the wells of fixed cells were washed with PBS and blocked with 1% dry milk in PBS for 30 min. at 37° C. One hundred µl of ferret anti-influenza A virus polyclonal antibody at 1:1000 dilution (kindly provided by Dr. Hunein F. Maassab, School of Public Health, University of Michigan) was added to the wells for 1 hr at 37° C. The cells were washed 4 times with washing buffer (PBS and 0.05% TWEEN-20), and incubated with 100 µl at 1:1000 dilution of goat anti-ferret peroxidase conjugated antibody (Kirkegaard & Perry Laboratories, Gaithersburg, Mass.) for 30 min. at 37° C. Cells were washed 4 times and incubated with 100 µl of 1-STEP TURBO TMB-ELISA substrate (Pierce, Rockford, Ill.) until color had developed. The reaction was stopped with 1 N sulfuric acid and plates were read at a wavelength of 450 nm in an ELISA microtiter reader.

β-galactosidase assay: β-galactosidase assay was performed on cell extracts as described elsewhere (Lim, 1989). Briefly, 293 cells were seeded on 96-well "U"-bottom tissue culture plates at approximately $4\times10^4$ cells/well and incubated overnight at 37° C./5% $CO_2$ in maintenance medium. The next day, the medium was removed and the cells were washed with 100 µl Dulbecco's phosphate buffered saline (DPBS). Adenovirus stock was diluted in infection medium to a concentration of $5\times10^7$ pfu/ml and mixed with different concentrations of BCTP as described below. After treatment with BCTP, virus was diluted with infection medium to a concentration of $1\times10^4$ pfu/ml and overlaid on 293 cells. Cells were incubated at 37° C./5% $CO_2$ for 5 days, after which the plates were centrifuged, the medium was removed and the cells were washed three times with PBS without Ca++ and Mg++. After the third wash, the PBS was aspirated and 100 µl of 1× Reporter Lysis Buffer (Promega, Madison, Wis.) was placed in each well. To enhance cell lysis, plates were frozen and thawed three times and the β-galactosidase assay was performed following the instruction provided by the vendor of β-galactosidase (Promega, Madison, Wis.) with some modifications. Five microliters of cell extract was transferred to a 96-well flat bottom plate and mixed with 45 µl of 1× Reporter Lysis Buffer (1:10). Subsequently 50 µl of 2× assay buffer (120 mM $Na_2HPO_4$, 80 mM $NaH_2PO_4$, 2 mM $MgCl_2$, 100 mM β-mercaptoethanol, 1.33 mg/ml ONPG (Sigma, St. Louis, Mo.) were added and mixed with the cell extract. The plates were incubated at RT until a faint yellow color developed. At that time the reaction was stopped by adding 100 (1 of 1 M sodium bicarbonate. Plates were read at a wavelength of 420 nm in an ELISA microplate reader. A standard, consisting of (u/µl β-galactosidase (Sigma, St. Louis, Mo.) supplemented in 50 mM bicine buffer (Sigma, St. Louis, Mo.), pH 7.5 and 100 (g/ml BSA) diluted in the 1× Reporter Lysis Buffer, was run with all assays. The units of β-galactosidase in each cell extract was calculated by regression analysis by reference to the levels in the standard and divided by milligrams of protein in the cell extract sample.

Cellular toxicity and virus treatment with lipid preparations: Prior to viral susceptibility testing, cytotoxicity of SLPs on MDCK and 293 cells was assessed by microscope inspection and MTT assay. The dilutions of the mixture of virus and SLPs applied in susceptibility testing were made to be at least one order of magnitude higher than the safe concentration of SLP assessed. Approximately $1\times10^8$ pfu of either influenza A or adenovirus were incubated with lipid preparation at final concentrations of 1:10, 1:100, and 1:1000 for different time periods as indicated in results on a shaker. After incubation, serial dilutions of the SLP/virus mixture were made in proper infection media and overlaid on MDCK (influenza A) or 293 (adenovirus) cells to perform PRA, cellular ELISA or β-galactosidase assays as described above.

Electron microscopy: Influenza A virus was semi-purified from allantoic fluid by passing through a 30% sucrose cushion prepared with GTNE (glycine 200 mM, Tris-HCl 10 mM (pH 8.8), NaCl 100 mM, and EDTA 1 mM) using ultra centrifugation (Beckman rotor SW 28 Ti, at 20,000 rpm for 16 hours). Pelleted virus was reconstituted in GTNE. Ten microliters of respective samples (adenovirus, influenza virus, adenovirus+BCTP, influenza virus+BCTP) were incubated for 15 and 60 min, then placed on parlodian coated 200 mesh copper grids for 2 min. Then 5 µl of 2% cacodylated-buffered glutaraldehyde was added. The fluid was removed with filter paper after 3 min. Ten microliters of 7% uranyl acetate was added to the grid and drawn off with filter paper after 30 sec. The grids were allowed to dry 10 min and examined on a Philips EM400T transmission electron microscope. Micrographs were recorded in Fuji FG film at magnifications of 200,000×.

Figure 22A:
Figure 22B:
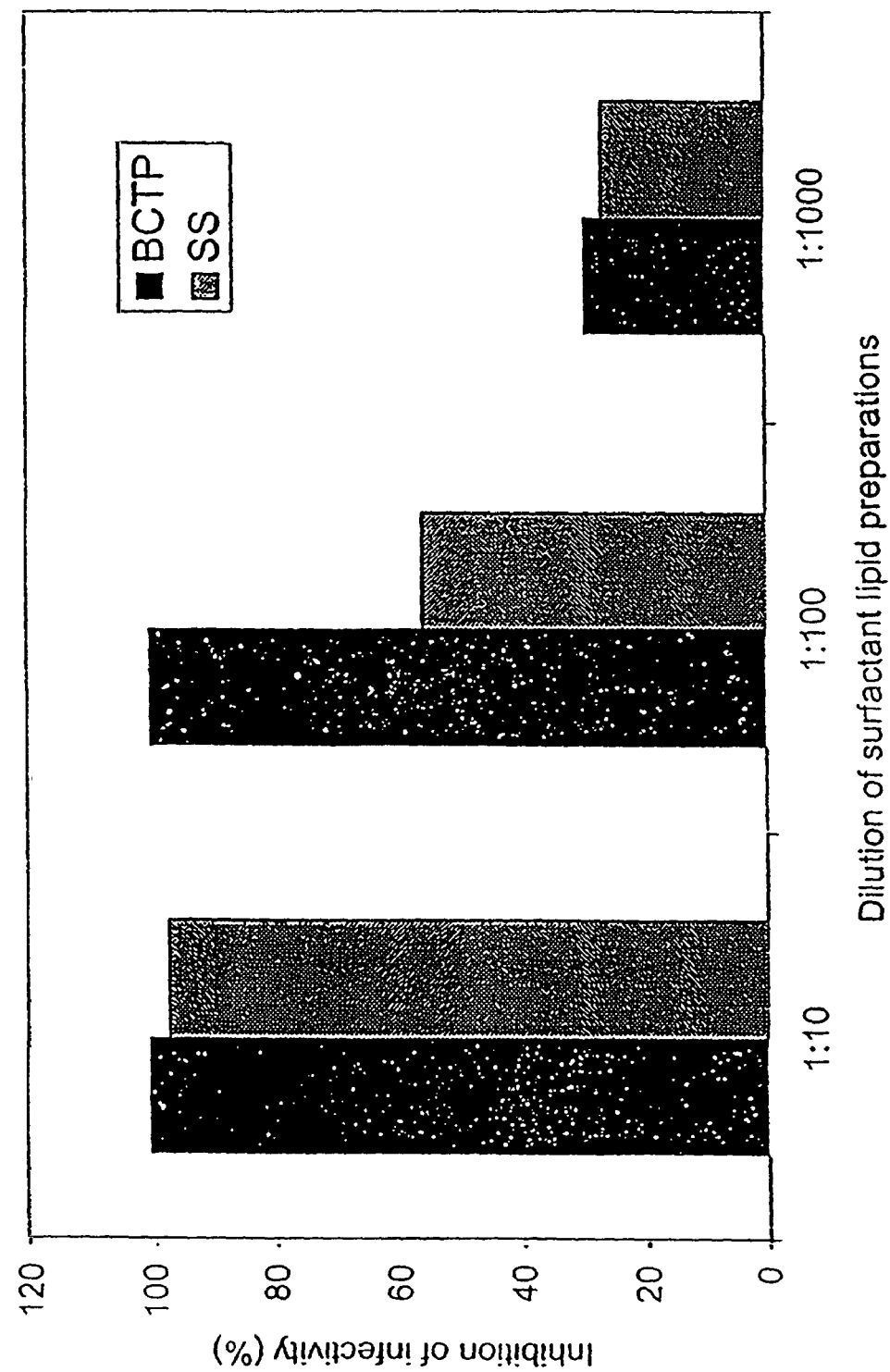

Susceptibility testing of influenza A to SLPS: the effect of four surfactant lipid preparations (BCTP, NN, $W_{80}8P$, and SS) on influenza A infection of MDCK cells was investigated. All tested preparations inhibited influenza A virus infection to varying degrees as shown in FIG. 22. BCTP and SS exhibited over 95% inhibition of influenza A infection at a 1:10 dilution. NN and $W_{80}8P$ showed only an intermediate effect on influenza A virus, reducing infection by approximately 40%. BCTP's virucidal effect was undiminished even at a 1:100 dilution. SS showed less effect at a 1:100 dilution inhibiting influenza A infection by 55%. These two lipid preparations at 1:1000 dilution displayed only weak inhibitory effect on virus infectivity at the range of 22-29% (FIG. 23B).

Since BCTP and SS both showed strong inhibitory effect on virus infectivity, PRA was used to verify data obtained from cellular ELISA. PRA confirmed the efficacy of BCTP and SS. BCTP reduced the number of plaques from an average of 50.88 to 0 at a 1:10 dilution (Table 21). At dilution 1:100, BCTP maintained virucidal effectiveness. At dilution 1:100 SS reduced the number of plaques only approximately 7% as compared with untreated virus.

TABLE 21

| Treatment Dilution of the agent: | Plaque forming units BCTP | Plaque forming units SS |
|---|---|---|
| 1:10$^a$ | 0.00$^b$ (+/−0.00)$^c$ | 0.00 (+/−0.00) |
| 1:100 | 0.00 (+/−0.00) | 1.55 (+1-0.12) |
| Untreated virus | 50.88 (+/−1-0.25) | 23.52 (+/−0.18) |

$^a$Virus was incubate with SLPs for 30 minutes.
$^b$Number of plaques.

Kinetics of BCTP action on influenza A virus: To investigate the time requirement for BCTP to act on influenza A infectivity, virus was incubated with BCTP at two dilutions (1:10, 1:100) and four different time intervals (5, 10, 15, 30 min). Subsequently, plaque reduction assay was performed. As shown in Table 22, after five min of incubation with BCTP at either dilution, influenza A virus infectivity of MDCK cells was completely abolished. There was no significant difference between the interaction of BCTP with influenza A virus regardless of concentration or time.

TABLE 22

| | BCTP treatment/dilution | | |
|---|---|---|---|
| Time (min) | 1:10 | 1:100 | untreated |
| 5 | 0.00$^a$ | 0.00 | 35.25 |
| | (+/−0.00)$^b$ | (+/−0.00) | (+/−0.94) |
| 10 | 0.00 | 0.25 | 39.25 |
| | (+/−0.00) | (+/−0.12) | (+/−1.95) |
| 15 | 0.00 | 0.25 | 31.50 |
| | (+/−0.00) | (+/−0.12) | (+/−1.05) |
| 30 | 0.00 | 0.00 | 26.50 |
| | (+/−0.00) | (+/−0.00) | (+/−0.08) |

Figure 23:
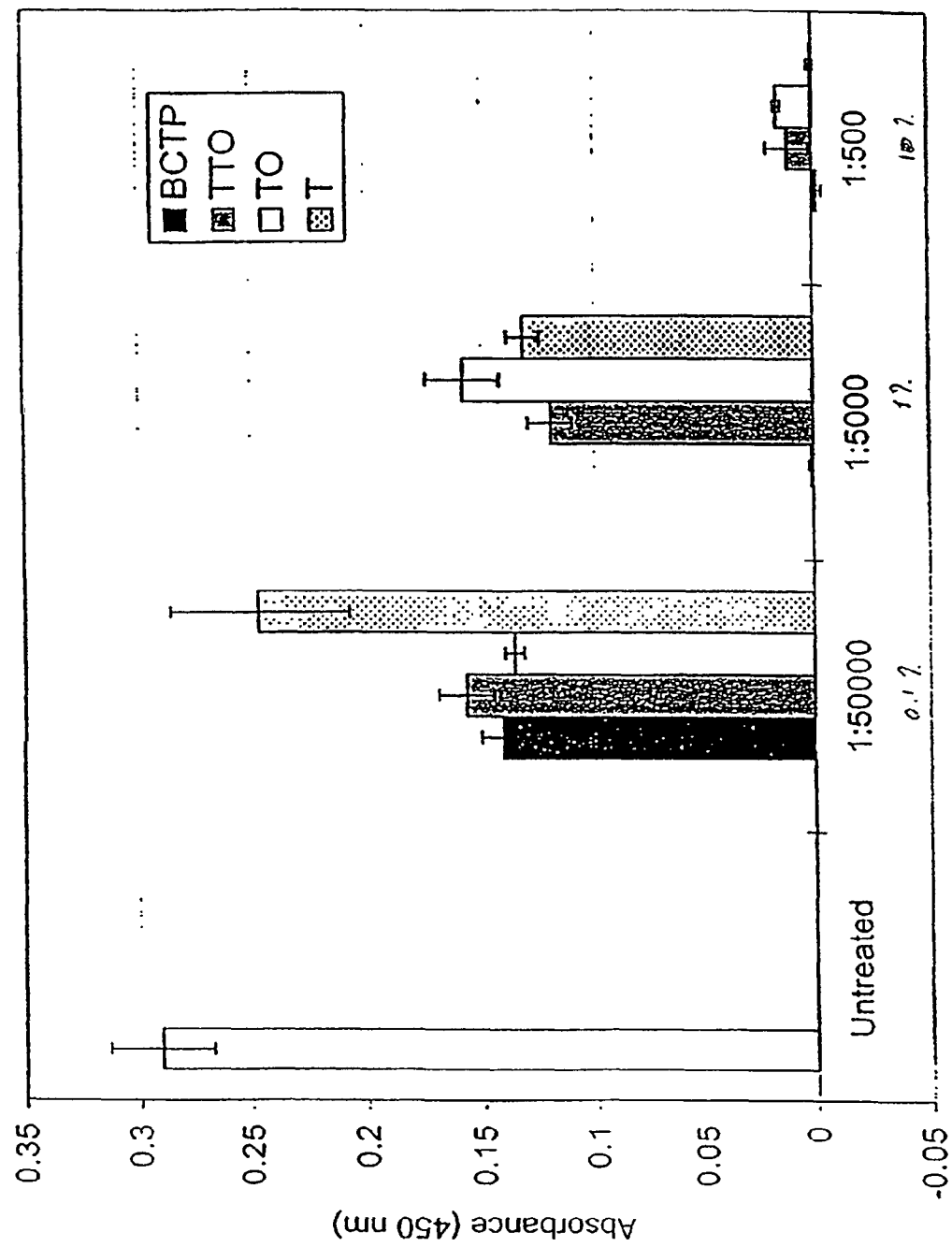

Anti-influenza A efficacy of BCTP: Since TRITON X-100 detergent has anti-viral activity (Maha and Igarashi, 1997; Portocala et al., 1976), it was investigated whether TRITON X-100 alone or combined with individual BCTP components inhibits influenza A infectivity to the same extent as BCTP. Influenza A virus was treated with: 1) BCTP, 2) the combination of tri(n-butyl)phosphate, TRITON X-100, and soybean oil (TTO), 3) TRITON X-100 and soybean oil (TO), or 4) TRITON X-100 (T) alone. BCTP was significantly more effective against influenza A virus at 1:10 and 1:100 dilutions (TRITON X-100 dilution of 1:500, and 1:5000) than TRITON X-100 alone or mixed with the other components tested (FIG. 23). At the dilution 1:1000, BCTP (TRITON X-100 dilution of 1:50,000) was able to reduce influenza A infection of MDCK cells by approximately 50% while TRITON X-100 alone at the same concentration was completely ineffective.

Figure 24:
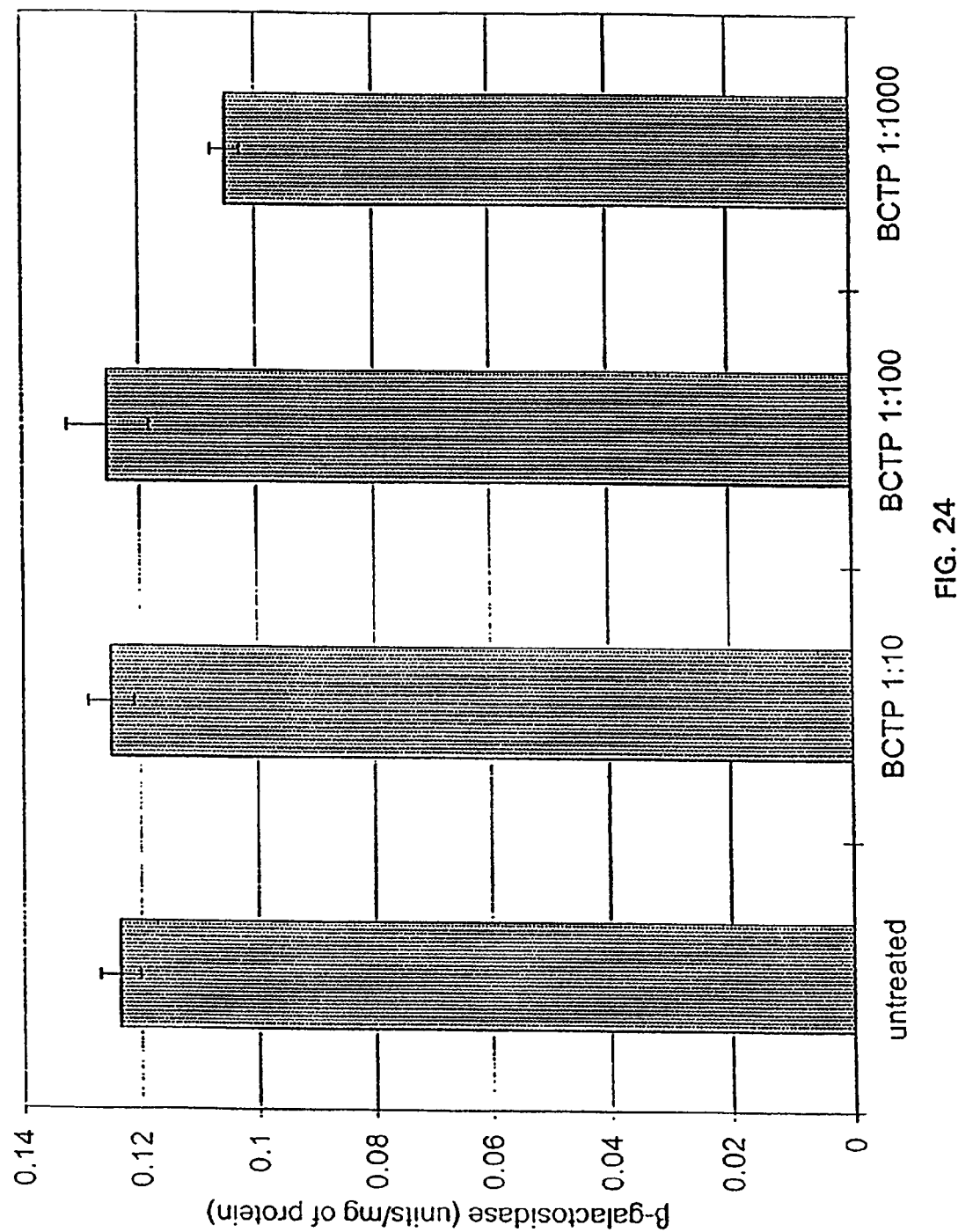

BCTP does not affect infectivity of non-enveloped virus: To investigate whether BCTP may affect the infectivity of non-enveloped virus, genetically engineered adenovirus containing LacZ gene was used, encoding β-galactosidase. This adenovirus construct was deficient in the transforming gene and therefore can replicate and transform only permissive cells containing the transforming gene of adenovirus 5. The 293 cells, which constitutively express transforming gene, were employed to promote adenovirus replication and production of β-galactosidase enzyme. As shown in FIG. 24, BCTP treatment did not affect the ability of adenovirus to replicate and express β-galactosidase activity in 293 cells. Both BCTP treated and untreated adenovirus produced approximately 0.11 units of β-galactosidase enzyme.

Figure 25:
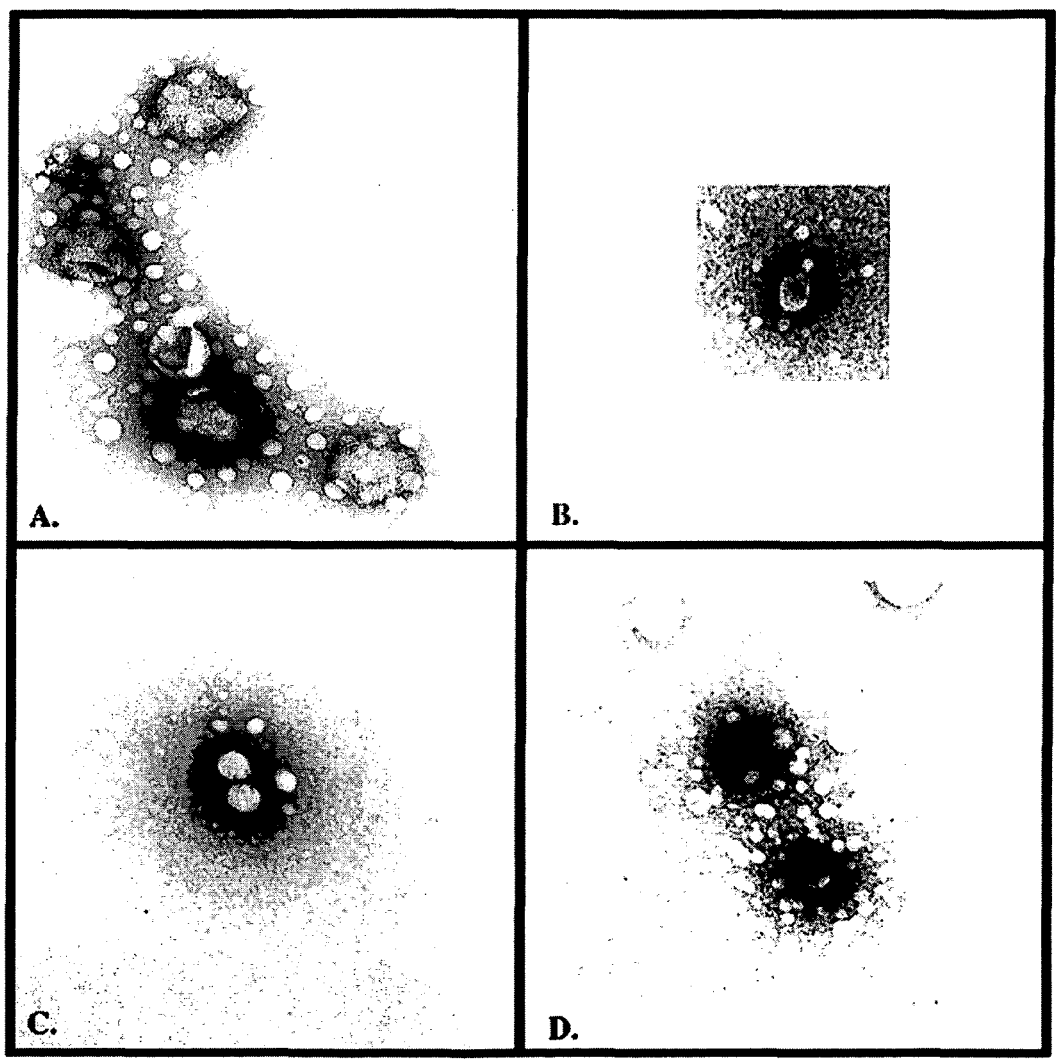

Action of BCTP on enveloped virus: Since BCTP only altered the infectivity of enveloped viruses, the action of this nanoemulsion on enveloped virus integrity was further investigated using electron microscopy. As shown in FIG. 25D, after a 60 min incubation with 1:100 dilution of BCTP, the structure of adenovirus is unchanged. A few recognizable influenza A virions were located after 15 min incubation with BCTP (FIG. 25B), however, no recognizable influenza A virions were found after 1 h incubation. BCTP's efficacy against influenza A virus and its minimal toxicity to mucous membranes demonstrates its potential as an effective disinfectant and agent for prevention of diseases resulting from infection with enveloped viruses.

Example 13

Temperature and EDTA Effects on W205EC Treatment of S. typhimurium

Figure 32:
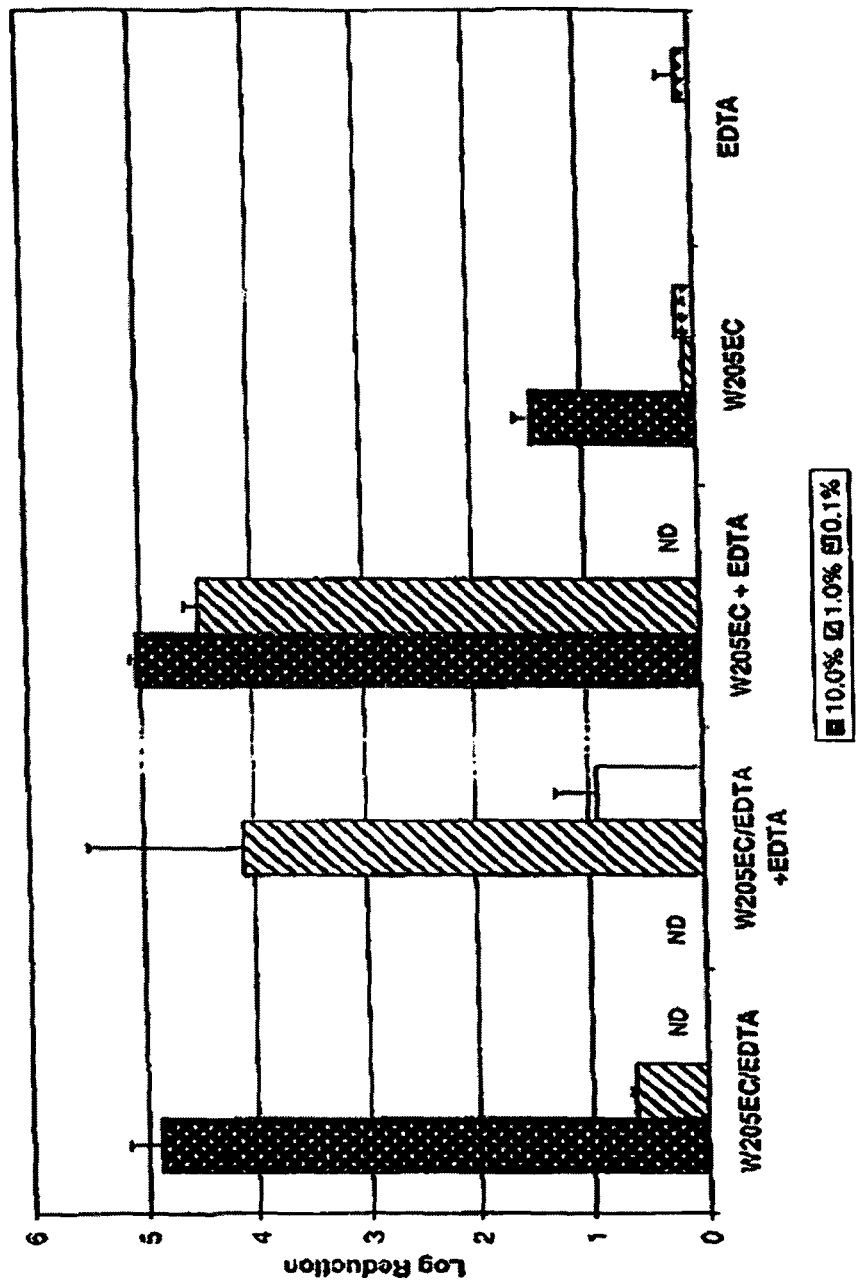
Figure 33:
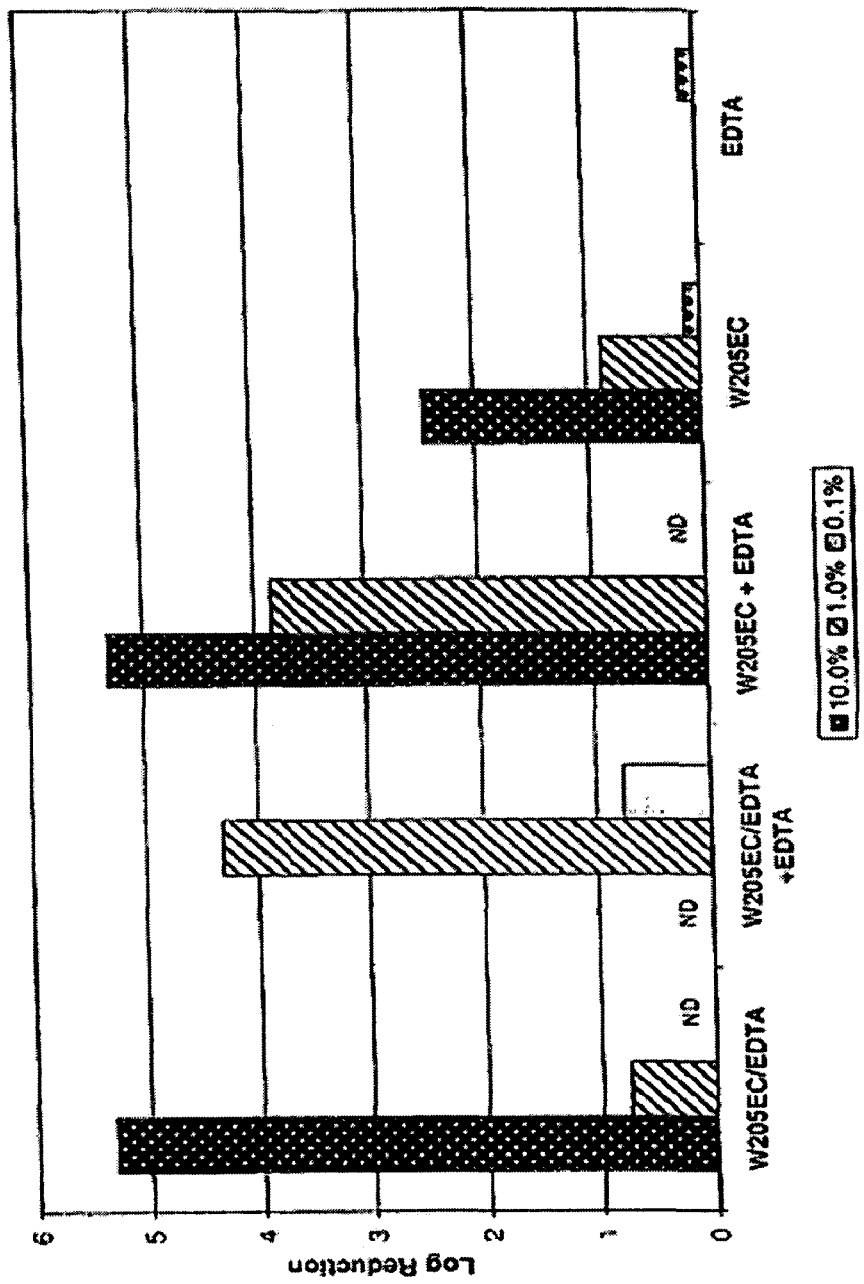

FIGS. 31 and 32 show the treatment of Salmonellae with different emulsions of the present invention with the addition of 0.1% EDTA. The EDTA improved the bactericidal activity of the emulsion at both 40° C. (FIG. 32) and 50° C. (FIG. 33). The emulsions were tested at 10.0%, 1.0%, and 0.1% dilutions.

Example 14

Antimicrobial Properties of X8PC and $W_{20}5EC$

Figure 35:
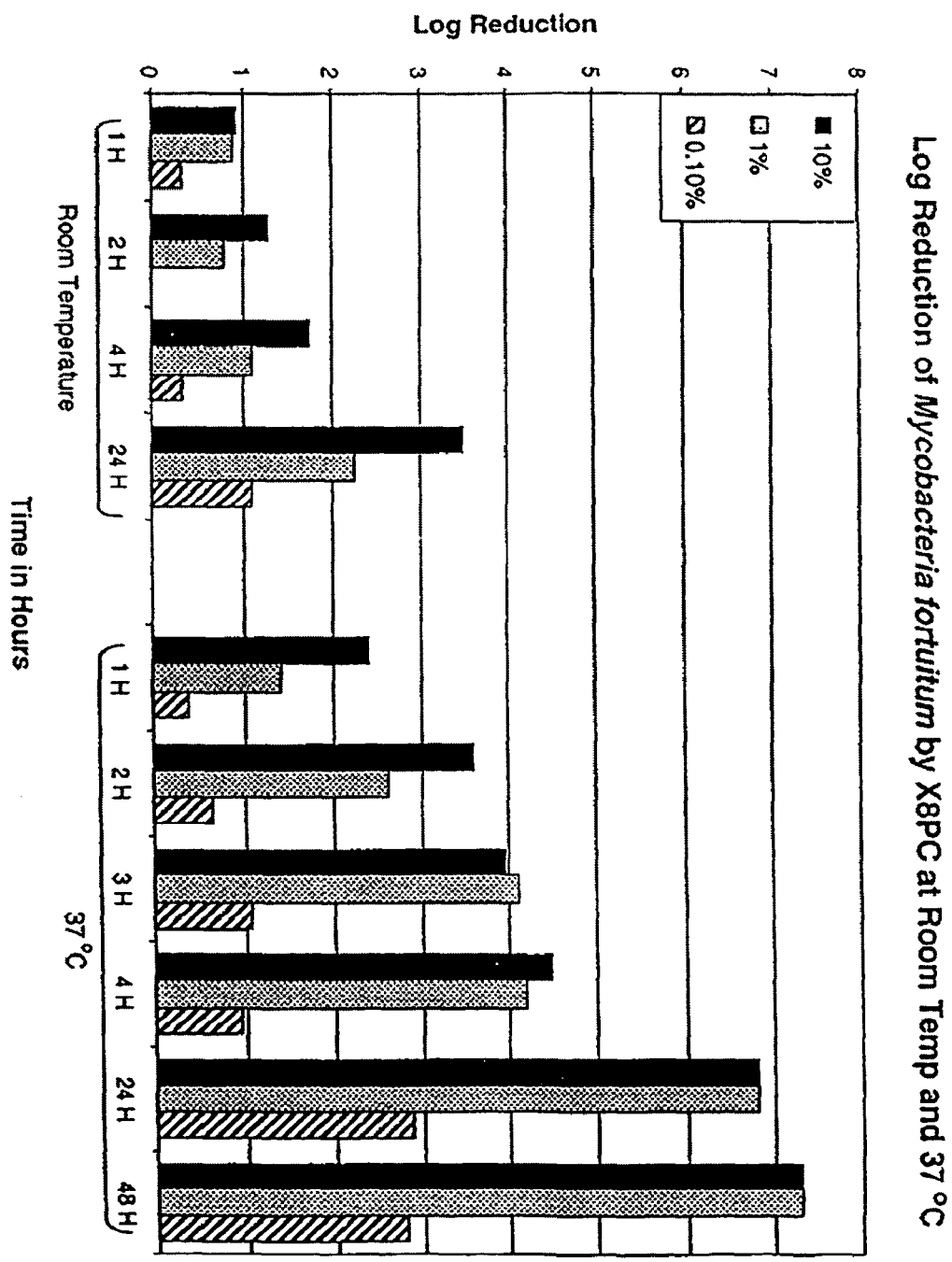

As described above, the emulsion X8PC is composed of about 8 vol. % of TRITON X-100, about 8 vol. % of TBP, about 1% of CPC, about 64 vol. % of soybean oil, and about 19 vol. % of $DiH_2O$ and the emulsion $W_{20}5EC$ is composed of from about 5 vol. % of TWEEN 20, from about 8 vol. % of ethanol, from about 1 vol. % of CPC, about 64 vol. % of oil (e.g., soybean oil), and about 22 vol. % of $DiH_2O$. X8PC and $W_{20}5EC$ were tested for their ability to reduce the growth of a number of microorganisms under various conditions. FIG. 35 shows the log reduction of Mycobacteria fortuitum by X8PC at 10%, 1% and 0.1% dilutions at room temperature and 37° C.

A 2% emulsion of $W_{20}5EC$ (with and without 1%, 2%, and 3% Natrosol) each showed an approximately 2 log reduction in E. coli for both dry and wet bacteria after a 15 minute incubation at room temperature. A 2% emulsion of $W_{20}5EC$ (with and without 1%, 2%, and 3% Natrosol) each showed an approximately 4 log reduction in S. aureus for both dry and wet bacteria after a 15 minute incubation at room temperature. A 2% emulsion of $W_{20}5EC$ (with and without 1%, 2%, and 3% Natrosol) each showed an approximately 3 log reduction in N. gonorrhoeae for wet bacteria after a 15 minute incubation at room temperature.

A rubber surface experiment was conducted to test the bactericidal activity of 1% $W_{20}5EC$ at multiple temperatures and diluted in different types of water. A one foot surface was smeared with 20 g of belt scrapings. *S. typhimurium* was manually sprayed onto the surface and allowed to dry for 20 minutes. The treatment was applied in three one minute intervals with a one minute time pause between each interval. A ten minute incubation period at room temperature was allowed. The results are shown in FIG. 36. The data demonstrate that $W_{20}5EC$ is effective using $diH_2O$, distilled water, and tap water at each temperature tested.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in relevant fields are intended to be within the scope of the following claims.

We claim:

1. A method for treating a subject with a microbial infection comprising administering a nanoemulsion, or a dilution thereof, to said subject, wherein said administering is via a route selected from the group consisting of intradermal injection, subcutaneous injection, intramuscular injection, intraperitoneal injection, orally, nasally, buccally, rectally, vaginally, topically, and by inhalation, wherein said nanoemulsion comprises:
   1. 30-90%, 60-80%, or 60-70% by volume oil;
   2. 3-15% by volume solvent; wherein said solvent is selected from the group consisting of ethanol and glycerol;
   3. 3-15% by volume surfactant; wherein said surfactant is selected from the group consisting of polyoxyethylenesorbitan monolaurate and polyoxyethylenesorbitan monooleate; and
   4. water;

and wherein said microbial infection is selected from the group consisting of microbial infection with a bacteria, microbial infection with a virus, and microbial infection with a fungus.

2. The method of claim 1, wherein said bacteria is *Streptococcus pyogenes, Streptococcus aglactiae, Streptococcus pneumonia, Staphylococcus aureus, Neisseria gonorhoeae, Haemophilus influenza, Vibrio cholera, E. coli, Salmonella typhimurium, Shigella dysenteriae, Shigella dysenteriae, Proteus mirabilis, Pseudomonas aeruginosa, Bacillus anthracis, Bacillus anthracis* spores, *Bacillus cereus, Bacillus cereus* spores, *Bacillus subtilus, Bacillus subtilus* spores, *Yersinia enterocolitica*, or *Yersinia pseudotuberculosis*.

3. The method of claim 1, wherein said fungus is *Candida albicans* or *Candida tropicalis*.

4. The method of claim 1, wherein said virus is influenza A H2N2, influenza B-Hong Kong, vaccinia virus, herpes simplex virus, Sendai virus, Sindbis virus, or adenovirus.

5. The method of claim 1, wherein said nanoemulsion is administered in the form of a lotion, cream, ointment, salve, spray, injectable composition, or ingestible solution.

6. The method of claim 1, wherein said nanoemulsion further comprises 0.5-2.0% cetylpyridinium chloride (CPC).

7. The method of claim 1, wherein said nanoemulsion further comprises 0.5-2.0% benzalkonium chloride.

8. The method of claim 1, wherein said nanoemulsion comprises:
   a) about 5% by volume surfactant, wherein said surfactant is selected from the group consisting of polyoxyethylenesorbitan monolaurate and polyoxyethylenesorbitan monooleate;
   b) about 8% by volume solvent, wherein said solvent is selected from the group consisting of ethanol and glycerol;
   c) about 0.5-2% by volume CPC;
   d) about 64% by volume oil; and
   e) distilled water.

9. The method of claim 1, wherein said nanoemulsion comprises:
   a) about 5% by volume polyoxyethylenesorbitan monolaurate;
   b) about 8% by volume ethanol;
   c) about 1% by volume CPC;
   d) about 64% by volume oil; and
   e) distilled water.

10. The method of claim 1, wherein said nanoemulsion comprises:
    a) about 5% by volume polyoxyethylene (20) sorbitan monooleate (TWEEN 80);
    b) about 8% by volume ethanol;
    c) about 1% by volume CPC;
    d) about 64% by volume oil;
    e) distilled water.

11. A method of treating a surface of an inanimate object comprising exposing said surface to a composition comprising a nanoemulsion or a dilution thereof, wherein said nanoemulsion comprises:
    1. 30-90%, 60-80%, or 60-70% by volume oil;
    2. 3-15% by volume solvent; wherein said solvent is selected from the group consisting of ethanol and glycerol;
    3. 3-15% by volume surfactant; wherein said surfactant is selected from the group consisting of polyoxyethylenesorbitan monolaurate and polyoxyethylenesorbitan monooleate; and
    4. water;

wherein said composition optionally comprises a halogen and/or interaction enhancer and/or a quaternary ammonium containing compound and/or other component
and wherein said other component is a flavoring compound, sweetener, bulking agent, or food additive.

12. The method of claim 11, wherein said exposing decontaminates said surface.

13. The method of claim 12, wherein decontaminating said surface comprises killing and/or inactivating a bacteria, fungus, virus, or bacterial spore.

14. The method of claim 13, wherein said virus is influenza A virus, avian influenza virus, H5N1 influenza virus, West Nile virus, SARS virus, Marburg virus, Arenaviruses, Nipah virus, alphavirus, filovirus, herpes simplex virus I, herpes simplex virus II, sendai virus, sindbis virus, vaccinia virus, parvovirus, human immunodeficiency virus, hepatitis B virus, hepatitis C virus, hepatitis A virus, cytomegalovirus, human papilloma virus, picornavirus, hantavirus, junin virus, ebola virus, or pathogen product derived from a virus.

15. The method of claim 13, wherein said bacteria is *Bacillus cereus, Bacillus circulans* and *Bacillus megaterium, Bacillus anthracis*, bacterial of the genus *Brucella, Vibrio* cholera, *Coxiella burnetii, Francisella tularensis, Chlamydia psittaci, Ricinus communis, Rickettsia prowazekii*, bacteria of the genus *Salmonella, Cryptosporidium parvum, Burkholderia pseudomallei, Clostridium perfringens, Clostridium botulinum, Vibrio cholerae, Streptococcus pyogenes, Streptococcus agalactiae, Streptococcus pneumonia, Staphylococcus aureus, Neisseria gonorrhea, Haemophilus influenzae, Escherichia coli, Salmonella typhimurium, Shigella dysenteriae, Proteus mirabilis, Pseudomonas aeruginosa, Yersinia pestis, Yersinia enterocolitica, Yersinia pseudotuberculosis*, or pathogen product derivded from bacteria.

16. The method of claim 13, wherein said fungus is *Candida, Aspergillus, Fusarium, Trychophyton*, or pathogen product derived from fungus.

17. The method of claim 11, wherein said nanoemulsion comprises:
 a) about 5% by volume surfactant, wherein said surfactant is selected from the group consisting of polyoxyethylenesorbitan monolaurate and polyoxyethylenesorbitan monooleate;
 b) about 8% by volume solvent, wherein said solvent is selected from the group consisting of ethanol and glycerol;
 c) about 0.5-2% by volume CPC;
 d) about 64% by volume oil; and
 e) distilled water.

* * * * *